(12) United States Patent
Tawfik et al.

(10) Patent No.: US 10,688,330 B2
(45) Date of Patent: Jun. 23, 2020

(54) ISOLATED PHOSPHOTRIESTERASE POLYPEPTIDES, POLYNUCLEOTIDES ENCODING SAME AND USES THEREOF IN TREATING OR PREVENTING ORGANOPHOSPHATE EXPOSURE ASSOCIATED DAMAGE

(71) Applicants: Yeda Research and Development Co. Ltd., Rehovot (IL); University of Washington, Seattle, WA (US)

(72) Inventors: Dan S. Tawfik, Jerusalem (IL); Haim Leader, Rehovot (IL); Yaacov Ashani, Rehovot (IL); Izhack Cherny, Rehovot (IL); Moshe Goldsmith, Rehovot (IL); Per Jr. Greisen, Seattle, WA (US); Sagar D. Khare, Seattle, WA (US); Gustav Oberdorfer, Seattle, WA (US); David Baker, Seattle, WA (US); Sarel Fleishman, Rehovot (IL); Adi Goldenzweig, Rehovot (IL); Nidhi Aggarwal, Rehovot (IL)

(73) Assignees: Yeda Research and Development Co. Ltd., Rehovot (IL); University of Washington, Seattle, WA (US)

( * ) Notice: Subject to any disclaimer, the term of this patent is extended or adjusted under 35 U.S.C. 154(b) by 208 days.

(21) Appl. No.: 15/535,050

(22) PCT Filed: Dec. 10, 2015

(86) PCT No.: PCT/IL2015/051203
§ 371 (c)(1),
(2) Date: Jun. 11, 2017

(87) PCT Pub. No.: WO2016/092555
PCT Pub. Date: Jun. 16, 2016

(65) Prior Publication Data
US 2019/0083836 A1    Mar. 21, 2019

Related U.S. Application Data

(60) Provisional application No. 62/090,411, filed on Dec. 11, 2014.

(51) Int. Cl.
*C12N 9/16* (2006.01)
*A61P 25/00* (2006.01)
(Continued)

(52) U.S. Cl.
CPC ................ *A62D 3/02* (2013.01); *A61P 25/00* (2018.01); *C12N 9/16* (2013.01); *A62D 2101/02* (2013.01);
(Continued)

(58) Field of Classification Search
None
See application file for complete search history.

(56) References Cited

U.S. PATENT DOCUMENTS 8,735,124 B2     5/2014  Tawfik et al.
2006/0286006 A1  12/2006 McDaniel et al.

FOREIGN PATENT DOCUMENTS

WO    WO 2013/136335    9/2013
WO    WO 2016/092555    6/2016
WO    WO 2018/087759    5/2018

OTHER PUBLICATIONS

UniProt Accession No. OPD_BREDI, published Mar. 15, 2005 (Year: 2005).*
(Continued)

*Primary Examiner* — Richard C Ekstrom

(57) ABSTRACT

A genetically modified polypeptide is disclosed which comprises an amino acid sequence of phosphotriesterase (PTE)
(Continued)

having at least twice the catalytic efficiency for a V-type nerve agent as a polypeptide which consists of the sequence as set forth in SEQ ID NO: 1, when assayed under identical conditions.

30 Claims, 12 Drawing Sheets
(12 of 12 Drawing Sheet(s) Filed in Color)

Specification includes a Sequence Listing.

(51) Int. Cl.
*A62D 3/02* (2007.01)
*A62D 101/02* (2007.01)
*A62D 101/26* (2007.01)

(52) U.S. Cl.
CPC .. *A62D 2101/26* (2013.01); *C12Y 301/08001* (2013.01)

(56) References Cited

OTHER PUBLICATIONS

Communication Relating to the Results of the Partial International Search dated May 9, 2016 From the International Searching Authority Re. Application No. PCT/IL2015/051203.
International Preliminary Report on Patentability dated Jun. 22, 2017 From the International Bureau of WIPO Re. Application No. PCT/IL2015/051203. (14 Pages).
International Search Report and the Written Opinion dated Jul. 21, 2016 From the International Searching Authority Re. Application No. PCT/IL2015/051203.
Bigley et al. "Enzymatic Neutralization of the Chemical Warfare Agent VX: Evolution of Phosphotriesterase for Phosphorothiolate Hydrolysis", Journal of the American Chemical Society, XP055265034, 135(28): 10426-10432, Jun. 21, 2013.
Cherny et al. "Engineering V-Type Nerve Agents Detoxifying Enzymes Using Computationally Focused Libraries", ACS Chemical Biology, XP055264549, 8(11): 2394-2403, Nov. 15, 2013. Table 2, p. 2394, r-h Col., Para 1—p. 2395, 1-h Col., Para 2, p. 2401, 1-h Col., Para 5—r-h Col., Para 2.
Roodveldt et al. "Directed Evolution of Phosphotriesterase From Pseudomonas Diminuta for Heterologous Expression in Escherichia Coli Results in Stabilization of the Metal-Free State", Protein Engineering Design & Selection, 18(1): 51-58, Published Online March 15, 2005.
Worek et al. "Post-Exposure Treatment of VX Poisoned Guinea Pigs With the Engineered Phopshotriesterase Mutant C23: A Proof-of-Concept Study", Toxicology Letters, XP029089901, 231(1): 45-54, Available Online Sep. 6, 2014.
International Search Report and the Written Opinion dated Jan. 16, 2018 From the International Searching Authority Re. Application No. PCT/IL2017/051220. (17 Pages).
Goldsmith et al. "Catalytic Efficiencies of Directly Evolved Phosphotriesterase Variants With Structurally Different Organophosphorus Compounds In Vitro", Archives of Toxicology, XP036076949, 90(11): 2711-2724, Published Online Nov. 26, 2015. Abstract, p. 2715, r-h Col., Last Para—p. 2716, r-h Col., Para 1, p. 2720, 1-h Col., Para 2—r-h Col., Para 1, p. 2721, r-h Col., Para 2—p. 2722, 1-h Col., Para 1, Tables 7, 8.
Jacquet et al. "Current and Emerging Strategies for Organophosphate Decontamination: Special Focus on Hyperstable Enzymes", Environmental Science and Pollution Research International, XP035938405, 23(9): 8200-8218, Published Online Feb. 2, 2016. Abstract, p. 8205, r-h Col., Para 3—p. 8207, 1-h Col., Para 3.
International Preliminary Report on Patentability dated May 23, 2019 From the International Bureau of WIPO Re. Application No. PCT/IL2017/051220. (9 Pages).

* cited by examiner

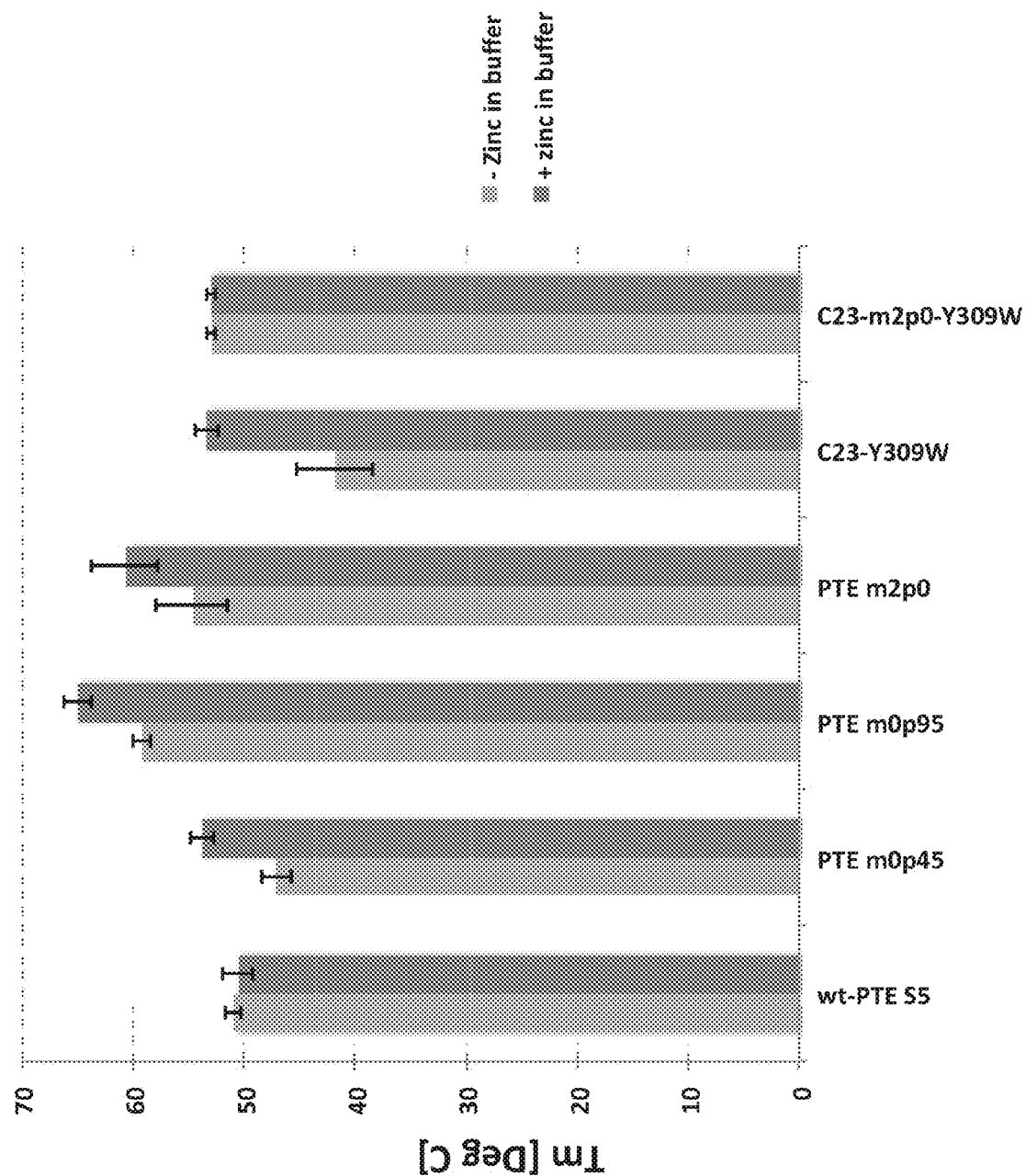

SEQUENCE LISTING

<160> NUMBER OF SEQ ID NOS: 36

<210> SEQ ID NO 1
<211> LENGTH: 727
<212> TYPE: PRT
<213> ORGANISM: Artificial Sequence
<220> FEATURE:
<223> OTHER INFORMATION: amino acid sequence of C23 with MBP binding
      protein and signal sequence - no mutations

<400> SEQUENCE: 1

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

-continued

```
Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
        260                 265                 270

Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Ile Thr Asn Ser Gly Asp Arg Ile Asn
385                 390                 395                 400

Thr Val Arg Gly Pro Ile Thr Ile Ser Glu Ala Gly Phe Thr Leu Thr
                405                 410                 415

His Glu His Ile Cys Gly Ser Ser Ala Gly Phe Leu Arg Ala Trp Pro
            420                 425                 430

Glu Phe Phe Gly Ser Arg Ala Ala Leu Val Glu Lys Ala Val Arg Gly
        435                 440                 445

Leu Arg Arg Ala Arg Ala Ala Gly Val Arg Thr Ile Val Asp Val Ser
450                 455                 460

Thr Phe Asp Ile Gly Arg Asp Val Ser Leu Leu Ala Glu Val Ser Arg
465                 470                 475                 480

Ala Ala Asp Val His Ile Val Ala Ala Thr Gly Leu Trp Glu Asp Pro
                485                 490                 495

Pro Leu Ser Met Arg Leu Arg Ser Val Glu Glu Leu Thr Gln Phe Phe
            500                 505                 510

Leu Arg Glu Ile Gln Tyr Gly Ile Glu Asp Thr Gly Ile Arg Ala Gly
        515                 520                 525

Ile Ile Lys Val Ala Thr Asn Gly Lys Ala Thr Pro Phe Gln Glu Leu
    530                 535                 540

Val Leu Arg Ala Ala Arg Ala Ser Leu Ala Thr Gly Val Pro Val
545                 550                 555                 560

Thr Thr His Thr Ala Ala Ser Gln Arg Asp Gly Glu Gln Gln Ala Ala
                565                 570                 575

Ile Phe Glu Ser Glu Gly Leu Ser Pro Ser Arg Val Cys Ile Gly His
            580                 585                 590

Ser Asp Asp Thr Asp Asp Leu Ser Tyr Leu Thr Ala Leu Ala Ala Arg
        595                 600                 605

Gly Tyr Leu Ile Gly Leu Asp Gly Ile Pro His Ser Ala Ile Gly Leu
    610                 615                 620

Glu Asp Asn Ala Ser Ala Ser Ala Leu Leu Gly Asn Arg Ser Trp Gln
625                 630                 635                 640
```

```
Thr Arg Ala Leu Leu Ile Lys Ala Leu Ile Asp Gln Gly Tyr Met Lys
                645                 650                 655

Gln Ile Leu Val Ser Asn Asp Trp Leu Phe Gly Phe Ser Ser Tyr Val
            660                 665                 670

Thr Asn Ile Met Asp Val Met Asp Ser Val Asn Pro Asp Gly Met Ala
            675                 680                 685

Phe Ile Pro Leu Arg Val Ile Pro Phe Leu Arg Glu Lys Gly Val Ser
            690                 695                 700

Gln Glu Thr Leu Ala Gly Ile Thr Val Thr Asn Pro Ala Arg Phe Leu
705                 710                 715                 720

Ser Pro Thr Leu Arg Ala Ser
                725
```

<210> SEQ ID NO 2
<211> LENGTH: 336
<212> TYPE: PRT
<213> ORGANISM: Artificial Sequence
<220> FEATURE:
<223> OTHER INFORMATION: amino acid sequence of C23A203L for bacterial
      expression

<400> SEQUENCE: 2

```
Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Ala
        35                  40                  45

Ala Leu Val Glu Lys Ala Val Arg Gly Leu Arg Arg Ala Arg Ala Ala
    50                  55                  60

Gly Val Arg Thr Ile Val Asp Val Ser Thr Phe Asp Ile Gly Arg Asp
65                  70                  75                  80

Val Ser Leu Leu Ala Glu Val Ser Arg Ala Ala Asp Val His Ile Val
                85                  90                  95

Ala Ala Thr Gly Leu Trp Glu Asp Pro Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Asn
    130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Leu Ala Ser
                165                 170                 175

Gln Arg Asp Gly Glu Gln Gln Ala Ala Ile Phe Glu Ser Glu Gly Leu
            180                 185                 190

Ser Pro Ser Arg Val Cys Ile Gly His Ser Asp Asp Thr Asp Asp Leu
        195                 200                 205

Ser Tyr Leu Thr Ala Leu Ala Ala Arg Gly Tyr Leu Ile Gly Leu Asp
    210                 215                 220

Gly Ile Pro His Ser Ala Ile Gly Leu Glu Asp Asn Ala Ser Ala Ser
225                 230                 235                 240

Ala Leu Leu Gly Asn Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
            260                 265                 270
```

```
Trp Leu Phe Gly Phe Ser Ser Tyr Val Thr Asn Ile Met Asp Val Met
            275                 280                 285

Asp Ser Val Asn Pro Asp Gly Met Ala Phe Ile Pro Leu Arg Val Ile
290                 295                 300

Pro Phe Leu Arg Glu Lys Gly Val Ser Gln Glu Thr Leu Ala Gly Ile
305                 310                 315                 320

Thr Val Thr Asn Pro Ala Arg Phe Leu Ser Pro Thr Leu Arg Ala Ser
            325                 330                 335

<210> SEQ ID NO 3
<211> LENGTH: 727
<212> TYPE: PRT
<213> ORGANISM: Artificial Sequence
<220> FEATURE:
<223> OTHER INFORMATION: amino acid sequence of C23A203L for bacterial
      expression with MBP and signal sequence

<400> SEQUENCE: 3

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
```

```
              290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Ile
                370                 375                 380

Glu Gly Arg Ile Ser Glu Phe Ile Thr Asn Ser Gly Asp Arg Ile Asn
385                 390                 395                 400

Thr Val Arg Gly Pro Ile Thr Ile Ser Glu Ala Gly Phe Thr Leu Thr
                405                 410                 415

His Glu His Ile Cys Gly Ser Ser Ala Gly Phe Leu Arg Ala Trp Pro
                420                 425                 430

Glu Phe Phe Gly Ser Arg Ala Ala Leu Val Glu Lys Ala Val Arg Gly
                435                 440                 445

Leu Arg Arg Ala Arg Ala Ala Gly Val Arg Thr Ile Val Asp Val Ser
                450                 455                 460

Thr Phe Asp Ile Gly Arg Asp Val Ser Leu Leu Ala Glu Val Ser Arg
465                 470                 475                 480

Ala Ala Asp Val His Ile Val Ala Ala Thr Gly Leu Trp Glu Asp Pro
                485                 490                 495

Pro Leu Ser Met Arg Leu Arg Ser Val Glu Glu Leu Thr Gln Phe Phe
                500                 505                 510

Leu Arg Glu Ile Gln Tyr Gly Ile Glu Asp Thr Gly Ile Arg Ala Gly
                515                 520                 525

Ile Ile Lys Val Ala Thr Asn Gly Lys Ala Thr Pro Phe Gln Glu Leu
                530                 535                 540

Val Leu Arg Ala Ala Ala Arg Ala Ser Leu Ala Thr Gly Val Pro Val
545                 550                 555                 560

Thr Thr His Thr Leu Ala Ser Gln Arg Asp Gly Glu Gln Gln Ala Ala
                565                 570                 575

Ile Phe Glu Ser Glu Gly Leu Ser Pro Ser Arg Val Cys Ile Gly His
                580                 585                 590

Ser Asp Asp Thr Asp Asp Leu Ser Tyr Leu Thr Ala Leu Ala Ala Arg
                595                 600                 605

Gly Tyr Leu Ile Gly Leu Asp Gly Ile Pro His Ser Ala Ile Gly Leu
                610                 615                 620

Glu Asp Asn Ala Ser Ala Ser Ala Leu Leu Gly Asn Arg Ser Trp Gln
625                 630                 635                 640

Thr Arg Ala Leu Leu Ile Lys Ala Leu Ile Asp Gln Gly Tyr Met Lys
                645                 650                 655

Gln Ile Leu Val Ser Asn Asp Trp Leu Phe Gly Phe Ser Ser Tyr Val
                660                 665                 670

Thr Asn Ile Met Asp Val Met Asp Ser Val Asn Pro Asp Gly Met Ala
                675                 680                 685

Phe Ile Pro Leu Arg Val Ile Pro Phe Leu Arg Glu Lys Gly Val Ser
                690                 695                 700

Gln Glu Thr Leu Ala Gly Ile Thr Val Thr Asn Pro Ala Arg Phe Leu
705                 710                 715                 720
```

Ser Pro Thr Leu Arg Ala Ser
            725

<210> SEQ ID NO 4
<211> LENGTH: 336
<212> TYPE: PRT
<213> ORGANISM: Artificial Sequence
<220> FEATURE:
<223> OTHER INFORMATION: amino acid sequence of A 53 Q173N

<400> SEQUENCE: 4

Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Ala
        35                  40                  45

Ala Leu Val Glu Lys Ala Val Arg Gly Leu Arg Arg Ala Arg Ala Ala
    50                  55                  60

Gly Val Arg Thr Ile Val Asp Val Ser Thr Phe Asp Ala Gly Arg Asp
65                  70                  75                  80

Val Ser Leu Leu Ala Glu Val Ser Arg Ala Ala Asp Val His Ile Val
                85                  90                  95

Ala Ala Thr Gly Leu Trp Glu Asp Pro Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Asn
    130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Phe Ala Ser
                165                 170                 175

Gln Arg Asp Gly Glu Gln Gln Ala Ala Ile Phe Glu Ser Glu Gly Leu
            180                 185                 190

Ser Pro Ser Arg Val Cys Ile Gly His Ser Asp Asp Thr Asp Asp Leu
        195                 200                 205

Ser Tyr Leu Thr Ala Leu Ala Ala Arg Gly Tyr Leu Ile Gly Leu Asp
    210                 215                 220

Gly Ile Pro His Ser Ala Ile Gly Leu Glu Asp Asn Ala Ser Ala Ser
225                 230                 235                 240

Ala Leu Leu Gly Asn Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
            260                 265                 270

Trp Leu Phe Gly Phe Ser Ser Tyr Val Thr Asn Ile Met Asp Val Met
        275                 280                 285

Asp Ser Val Asn Pro Asp Gly Met Ala Phe Ile Pro Leu Arg Val Ile
    290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 5

<211> LENGTH: 365
<212> TYPE: PRT
<213> ORGANISM: Brevundimonas diminuta

<400> SEQUENCE: 5

Met Gln Thr Arg Arg Val Val Leu Lys Ser Ala Ala Ala Gly Thr
1               5                   10                  15

Leu Leu Gly Gly Leu Ala Gly Cys Ala Ser Val Ala Gly Ser Ile Gly
            20                  25                  30

Thr Gly Asp Arg Ile Asn Thr Val Arg Gly Pro Ile Thr Ile Ser Glu
        35                  40                  45

Ala Gly Phe Thr Leu Thr His Glu His Ile Cys Gly Ser Ser Ala Gly
    50                  55                  60

Phe Leu Arg Ala Trp Pro Glu Phe Phe Gly Ser Arg Lys Ala Leu Ala
65                  70                  75                  80

Glu Lys Ala Val Arg Gly Leu Arg Arg Ala Arg Ala Ala Gly Val Arg
                85                  90                  95

Thr Ile Val Asp Val Ser Thr Phe Asp Ile Gly Arg Asp Val Ser Leu
            100                 105                 110

Leu Ala Glu Val Ser Arg Ala Ala Asp Val His Ile Val Ala Ala Thr
        115                 120                 125

Gly Leu Trp Phe Asp Pro Pro Leu Ser Met Arg Leu Arg Ser Val Glu
    130                 135                 140

Glu Leu Thr Gln Phe Phe Leu Arg Glu Ile Gln Tyr Gly Ile Glu Asp
145                 150                 155                 160

Thr Gly Ile Arg Ala Gly Ile Ile Lys Val Ala Thr Thr Gly Lys Ala
                165                 170                 175

Thr Pro Phe Gln Glu Leu Val Leu Lys Ala Ala Ala Arg Ala Ser Leu
            180                 185                 190

Ala Thr Gly Val Pro Val Thr Thr His Thr Ala Ala Ser Gln Arg Asp
        195                 200                 205

Gly Glu Gln Gln Ala Ala Ile Phe Glu Ser Glu Gly Leu Ser Pro Ser
    210                 215                 220

Arg Val Cys Ile Gly His Ser Asp Asp Thr Asp Asp Leu Ser Tyr Leu
225                 230                 235                 240

Thr Ala Leu Ala Ala Arg Gly Tyr Leu Ile Gly Leu Asp His Ile Pro
                245                 250                 255

His Ser Ala Ile Gly Leu Glu Asp Asn Ala Ser Ala Ser Ala Leu Leu
            260                 265                 270

Gly Ile Arg Ser Trp Gln Thr Arg Ala Leu Leu Ile Lys Ala Leu Ile
        275                 280                 285

Asp Gln Gly Tyr Met Lys Gln Ile Leu Val Ser Asn Asp Trp Leu Phe
    290                 295                 300

Gly Phe Ser Ser Tyr Val Thr Asn Ile Met Asp Val Met Asp Arg Val
305                 310                 315                 320

Asn Pro Asp Gly Met Ala Phe Ile Pro Leu Arg Val Ile Pro Phe Leu
                325                 330                 335

Arg Glu Lys Gly Val Pro Gln Glu Thr Leu Ala Gly Ile Thr Val Thr
            340                 345                 350

Asn Pro Ala Arg Phe Leu Ser Pro Thr Leu Arg Ala Ser
        355                 360                 365

<210> SEQ ID NO 6
<211> LENGTH: 336
<212> TYPE: PRT

-continued

<213> ORGANISM: Artificial Sequence
<220> FEATURE:
<223> OTHER INFORMATION: amino acid sequence of PTE expressed in E.Coli
      without the MBP binding protein

<400> SEQUENCE: 6

Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Lys
        35                  40                  45

Ala Leu Ala Glu Lys Ala Val Arg Gly Leu Arg Arg Ala Arg Ala Ala
    50                  55                  60

Gly Val Arg Thr Ile Val Asp Val Ser Thr Phe Asp Ile Gly Arg Asp
65                  70                  75                  80

Val Ser Leu Leu Ala Glu Val Ser Arg Ala Ala Asp Val His Ile Val
                85                  90                  95

Ala Ala Thr Gly Leu Trp Phe Asp Pro Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Thr
130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Ala Ala Ser
                165                 170                 175

Gln Arg Gly Gly Glu Gln Gln Ala Ala Ile Phe Glu Ser Glu Gly Leu
            180                 185                 190

Ser Pro Ser Arg Val Cys Ile Gly His Ser Asp Asp Thr Asp Asp Leu
        195                 200                 205

Ser Tyr Leu Thr Ala Leu Ala Ala Arg Gly Tyr Leu Ile Gly Leu Asp
210                 215                 220

His Ile Pro His Ser Ala Ile Gly Leu Glu Asp Asn Ala Ser Ala Ser
225                 230                 235                 240

Ala Leu Leu Gly Ile Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
            260                 265                 270

Trp Leu Phe Gly Phe Ser Ser Tyr Val Thr Asn Ile Met Asp Val Met
        275                 280                 285

Asp Ser Val Asn Pro Asp Gly Met Ala Phe Ile Pro Leu Arg Val Ile
290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 7
<211> LENGTH: 728
<212> TYPE: PRT
<213> ORGANISM: Artificial Sequence
<220> FEATURE:
<223> OTHER INFORMATION: amino acid sequence of PTE expressed in E.Coli
      with the MBP binding protein (no additional mutations)

-continued

```
<400> SEQUENCE: 7

His Met Lys Ile Glu Glu Gly Lys Leu Val Ile Trp Ile Asn Gly Asp
1               5                   10                  15

Lys Gly Tyr Asn Gly Leu Ala Glu Val Gly Lys Lys Phe Glu Lys Asp
            20                  25                  30

Thr Gly Ile Lys Val Thr Val Glu His Pro Asp Lys Leu Glu Glu Lys
        35                  40                  45

Phe Pro Gln Val Ala Ala Thr Gly Asp Gly Pro Asp Ile Ile Phe Trp
    50                  55                  60

Ala His Asp Arg Phe Gly Gly Tyr Ala Gln Ser Gly Leu Leu Ala Glu
65                  70                  75                  80

Ile Thr Pro Asp Lys Ala Phe Gln Asp Lys Leu Tyr Pro Phe Thr Trp
                85                  90                  95

Asp Ala Val Arg Tyr Asn Gly Lys Leu Ile Ala Tyr Pro Ile Ala Val
            100                 105                 110

Glu Ala Leu Ser Leu Ile Tyr Asn Lys Asp Leu Leu Pro Asn Pro Pro
        115                 120                 125

Lys Thr Trp Glu Glu Ile Pro Ala Leu Asp Lys Glu Leu Lys Ala Lys
    130                 135                 140

Gly Lys Ser Ala Leu Met Phe Asn Leu Gln Glu Pro Tyr Phe Thr Trp
145                 150                 155                 160

Pro Leu Ile Ala Ala Asp Gly Gly Tyr Ala Phe Lys Tyr Glu Asn Gly
                165                 170                 175

Lys Tyr Asp Ile Lys Asp Val Gly Val Asp Asn Ala Gly Ala Lys Ala
            180                 185                 190

Gly Leu Thr Phe Leu Val Asp Leu Ile Lys Asn Lys His Met Asn Ala
        195                 200                 205

Asp Thr Asp Tyr Ser Ile Ala Glu Ala Ala Phe Asn Lys Gly Glu Thr
    210                 215                 220

Ala Met Thr Ile Asn Gly Pro Trp Ala Trp Ser Asn Ile Asp Thr Ser
225                 230                 235                 240

Lys Val Asn Tyr Gly Val Thr Val Leu Pro Thr Phe Lys Gly Gln Pro
                245                 250                 255

Ser Lys Pro Phe Val Gly Val Leu Ser Ala Gly Ile Asn Ala Ala Ser
            260                 265                 270

Pro Asn Lys Glu Leu Ala Lys Glu Phe Leu Glu Asn Tyr Leu Leu Thr
        275                 280                 285

Asp Glu Gly Leu Glu Ala Val Asn Lys Asp Lys Pro Leu Gly Ala Val
    290                 295                 300

Ala Leu Lys Ser Tyr Glu Glu Glu Leu Ala Lys Asp Pro Arg Ile Ala
305                 310                 315                 320

Ala Thr Met Glu Asn Ala Gln Lys Gly Glu Ile Met Pro Asn Ile Pro
                325                 330                 335

Gln Met Ser Ala Phe Trp Tyr Ala Val Arg Thr Ala Val Ile Asn Ala
            340                 345                 350

Ala Ser Gly Arg Gln Thr Val Asp Glu Ala Leu Lys Asp Ala Gln Thr
        355                 360                 365

Asn Ser Ser Ser Asn Asn Asn Asn Asn Asn Asn Asn Asn Asn Leu Gly
    370                 375                 380

Ile Glu Gly Arg Ile Ser Glu Phe Ile Thr Ser Gly Asp Arg Ile
385                 390                 395                 400

Asn Thr Val Arg Gly Pro Ile Thr Ile Ser Glu Ala Gly Phe Thr Leu
                405                 410                 415
```

```
Thr His Glu His Ile Cys Gly Ser Ser Ala Gly Phe Leu Arg Ala Trp
            420                 425                 430

Pro Glu Phe Phe Gly Ser Arg Lys Ala Leu Ala Glu Lys Ala Val Arg
            435                 440                 445

Gly Leu Arg Arg Ala Arg Ala Ala Gly Val Arg Thr Ile Val Asp Val
450                 455                 460

Ser Thr Phe Asp Ile Gly Arg Asp Val Ser Leu Leu Ala Glu Val Ser
465                 470                 475                 480

Arg Ala Ala Asp Val His Ile Val Ala Ala Thr Gly Leu Trp Phe Asp
                485                 490                 495

Pro Pro Leu Ser Met Arg Leu Arg Ser Val Glu Glu Leu Thr Gln Phe
            500                 505                 510

Phe Leu Arg Glu Ile Gln Tyr Gly Ile Glu Asp Thr Gly Ile Arg Ala
            515                 520                 525

Gly Ile Ile Lys Val Ala Thr Thr Gly Lys Ala Thr Pro Phe Gln Glu
530                 535                 540

Leu Val Leu Arg Ala Ala Ala Arg Ala Ser Leu Ala Thr Gly Val Pro
545                 550                 555                 560

Val Thr Thr His Thr Ala Ala Ser Gln Arg Gly Gly Glu Gln Gln Ala
                565                 570                 575

Ala Ile Phe Glu Ser Glu Gly Leu Ser Pro Ser Arg Val Cys Ile Gly
            580                 585                 590

His Ser Asp Asp Thr Asp Leu Ser Tyr Leu Thr Ala Leu Ala Ala
            595                 600                 605

Arg Gly Tyr Leu Ile Gly Leu Asp His Ile Pro His Ser Ala Ile Gly
            610                 615                 620

Leu Glu Asp Asn Ala Ser Ala Ser Ala Leu Leu Gly Ile Arg Ser Trp
625                 630                 635                 640

Gln Thr Arg Ala Leu Leu Ile Lys Ala Leu Ile Asp Gln Gly Tyr Met
                645                 650                 655

Lys Gln Ile Leu Val Ser Asn Asp Trp Leu Phe Gly Phe Ser Ser Tyr
            660                 665                 670

Val Thr Asn Ile Met Asp Val Met Asp Ser Val Asn Pro Asp Gly Met
            675                 680                 685

Ala Phe Ile Pro Leu Arg Val Ile Pro Phe Leu Arg Glu Lys Gly Val
            690                 695                 700

Pro Gln Glu Thr Leu Ala Gly Ile Thr Val Thr Asn Pro Ala Arg Phe
705                 710                 715                 720

Leu Ser Pro Thr Leu Arg Ala Ser
                725
```

<210> SEQ ID NO 8
<211> LENGTH: 727
<212> TYPE: PRT
<213> ORGANISM: Artificial Sequence
<220> FEATURE:
<223> OTHER INFORMATION: amino acid sequence of A53 Q173N for bacterial
      expression +MBP

<400> SEQUENCE: 8

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
```

```
                35                  40                  45
Pro Gln Val Ala Ala Thr Gly Asp Gly Pro Asp Ile Ile Phe Trp Ala
 50                  55                  60
His Asp Arg Phe Gly Gly Tyr Ala Gln Ser Gly Leu Leu Ala Glu Ile
 65                  70                  75                  80
Thr Pro Asp Lys Ala Phe Gln Asp Lys Leu Tyr Pro Phe Thr Trp Asp
                 85                  90                  95
Ala Val Arg Tyr Asn Gly Lys Leu Ile Ala Tyr Pro Ile Ala Val Glu
                100                 105                 110
Ala Leu Ser Leu Ile Tyr Asn Lys Asp Leu Leu Pro Asn Pro Pro Lys
                115                 120                 125
Thr Trp Glu Glu Ile Pro Ala Leu Asp Lys Glu Leu Lys Ala Lys Gly
130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
                180                 185                 190
Leu Thr Phe Leu Val Asp Leu Ile Lys Asn Lys His Met Asn Ala Asp
                195                 200                 205
Thr Asp Tyr Ser Ile Ala Glu Ala Ala Phe Asn Lys Gly Glu Thr Ala
                210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
                260                 265                 270
Asn Lys Glu Leu Ala Lys Glu Phe Leu Glu Asn Tyr Leu Leu Thr Asp
                275                 280                 285
Glu Gly Leu Glu Ala Val Asn Lys Asp Lys Pro Leu Gly Ala Val Ala
                290                 295                 300
Leu Lys Ser Tyr Glu Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
                355                 360                 365
Ser Ser Ser Asn Asn Asn Asn Asn Asn Asn Asn Asn Asn Leu Gly Ile
                370                 375                 380
Glu Gly Arg Ile Ser Glu Phe Ile Thr Asn Ser Gly Asp Arg Ile Asn
385                 390                 395                 400
Thr Val Arg Gly Pro Ile Thr Ile Ser Glu Ala Gly Phe Thr Leu Thr
                405                 410                 415
His Glu His Ile Cys Gly Ser Ser Ala Gly Phe Leu Arg Ala Trp Pro
                420                 425                 430
Glu Phe Phe Gly Ser Arg Ala Ala Leu Val Glu Lys Ala Val Arg Gly
                435                 440                 445
Leu Arg Arg Ala Arg Ala Ala Gly Val Arg Thr Ile Val Asp Val Ser
450                 455                 460
```

Thr Phe Asp Ala Gly Arg Asp Val Ser Leu Leu Ala Glu Val Ser Arg
465                 470                 475                 480

Ala Ala Asp Val His Ile Val Ala Ala Thr Gly Leu Trp Glu Asp Pro
            485                 490                 495

Pro Leu Ser Met Arg Leu Arg Ser Val Glu Glu Leu Thr Gln Phe Phe
        500                 505                 510

Leu Arg Glu Ile Gln Tyr Gly Ile Glu Asp Thr Gly Ile Arg Ala Gly
    515                 520                 525

Ile Ile Lys Val Ala Thr Asn Gly Lys Ala Thr Pro Phe Gln Glu Leu
530                 535                 540

Val Leu Arg Ala Ala Arg Ala Ser Leu Ala Thr Gly Val Pro Val
545                 550                 555                 560

Thr Thr His Thr Phe Ala Ser Gln Arg Asp Gly Glu Gln Gln Ala Ala
                565                 570                 575

Ile Phe Glu Ser Glu Gly Leu Ser Pro Ser Arg Val Cys Ile Gly His
            580                 585                 590

Ser Asp Asp Thr Asp Leu Ser Tyr Leu Thr Ala Leu Ala Ala Arg
        595                 600                 605

Gly Tyr Leu Ile Gly Leu Asp Gly Ile Pro His Ser Ala Ile Gly Leu
    610                 615                 620

Glu Asp Asn Ala Ser Ala Ser Ala Leu Leu Gly Asn Arg Ser Trp Gln
625                 630                 635                 640

Thr Arg Ala Leu Leu Ile Lys Ala Leu Ile Asp Gln Gly Tyr Met Lys
                645                 650                 655

Gln Ile Leu Val Ser Asn Asp Trp Leu Phe Gly Phe Ser Ser Tyr Val
            660                 665                 670

Thr Asn Ile Met Asp Val Met Asp Ser Val Asn Pro Asp Gly Met Ala
        675                 680                 685

Phe Ile Pro Leu Arg Val Ile Pro Phe Leu Arg Glu Lys Gly Val Pro
    690                 695                 700

Gln Glu Thr Leu Ala Gly Ile Thr Val Thr Asn Pro Ala Arg Phe Leu
705                 710                 715                 720

Ser Pro Thr Leu Arg Ala Ser
                725

<210> SEQ ID NO 9
<211> LENGTH: 2184
<212> TYPE: DNA
<213> ORGANISM: Artificial Sequence
<220> FEATURE:
<223> OTHER INFORMATION: MBP-C23-A203L DNA coding sequence

<400> SEQUENCE: 9
atgaaaatcg aagaaggtaa actggtaatc tggattaacg gcgataaagg ctataacggt     60
ctcgctgaag tcggtaagaa attcgagaaa gataccggaa ttaaagtcac cgttgagcat    120
ccggataaac tggaagagaa attcccacag gttgcggcaa ctggcgatgg ccctgacatt    180
atcttctggg cacacgaccg ctttggtggc tacgctcaat ctggcctgtt ggctgaaatc    240
accccggaca agcgttcca ggacaagctg tatccgttta cctgggatgc cgtacgttac    300
aacggcaagc tgattgctta cccgatcgct gttgaagcgt atcgctgat ttataacaaa    360 gatctgctgc cgaaccccgcc aaaaaacctgg gaagagatcc cggcgctgga taagaactg    420 aaagcgaaag gtaagagcgc gctgatgttc aacctgcaag aaccgtactt cacctggccg    480
ctgattgctg ctgacggggg ttatgcgttc aagtatgaaa acggcaagta cgacattaaa    540

```
gacgtgggcg tggataacgc tggcgcgaaa gcgggtctga ccttcctggt tgacctgatt      600
aaaaacaaac acatgaatgc agacaccgat tactccatcg cagaagctgc ctttaataaa      660
ggcgaaacag cgatgaccat caacggcccg tgggcatggt ccaacatcga caccagcaaa      720
gtgaattatg gtgtaacggt actgccgacc ttcaagggtc aaccatccaa accgttcgtt      780
ggcgtgctga gcgcaggtat taacgccgcc agtccgaaca agagctggc aaaagagttc       840 ctcgaaaact atctgctgac tgatgaaggt ctggaagcgg ttaataaaga caaaccgctg      900
ggtgccgtag cgctgaagtc ttacgaggaa gagttggcga agatccacg tattgccgcc       960 actatggaaa acgcccagaa aggtgaaatc atgccgaaca tcccgcagat gtccgctttc     1020
tggtatgccg tgcgtactgc ggtgatcaac gccgccagcg tcgtcagac tgtcgatgaa      1080 gccctgaaag acgcgcagac taattcgagc tcgaacaaca caacaataa caataacaac     1140 aacctcggga tcgagggaag gatttcagaa ttcatcacca cagcggcga tcggatcaat      1200 accgtgcgcg gtcctatcac aatctctgaa gcgggtttca cactgactca cgagcacatc     1260
tgcggcagct cggcaggatt cttgcgtgct tggccggagt tcttcggtag ccgcgcagcc     1320
ctagtggaaa aggctgtgag aggattgcgc gcgccagag cggctggcgt gcgaacgatt     1380
gtcgatgtgt cgactttcga tatcggtcgc gatgtcagtt tattggccga ggtttcgcgg     1440
gctgccgact tcatatcgt ggcggcgacc ggcttgtggg aggacccgcc actttcgatg     1500
cggttgagga gtgtagagga actcacacag ttcttcctgc gtgagattca atatggcatc     1560
gaagacaccg gaattagggc gggcattatc aaggtcgcga ccaatggcaa ggcgaccccc     1620
tttcaggagt tagtgttaag ggcggccgcc cgggccagct ggccaccgg tgttccggta      1680 accactcaca cgttggcaag tcagcgcgat ggtgagcagc aggccgccat ttttgagtcc     1740
gaaggcttga gccctcacg agtttgtatt ggtcacagcg atgatactga cgatttgagc     1800
tatctcaccg ccctcgctgc gcgcggatac ctcatcggtc tagacggcat cccgcacagt     1860
gcgattggtc tagaagataa tgcgagtgca tcagccctcc tgggcaaccg ttcgtggcaa     1920
acacgggctc tcttgatcaa ggcgctcatc gaccaaggct acatgaaaca aatcctcgtt     1980
tcgaatgact ggctgttcgg gttttcgagc tatgtcacca catcatgga cgtgatggat     2040 agcgtgaacc ccgacgggat ggccttcatt ccactgagag tgatcccatt cctacgagag     2100
aagggcgtct cacaggaaac gctggcaggc atcactgtga ccaaccccggc gcggttcttg     2160 tcaccgacct tgcgggcgtc atga                                              2184
```

<210> SEQ ID NO 10
<211> LENGTH: 2184
<212> TYPE: DNA
<213> ORGANISM: Artificial Sequence
<220> FEATURE:
<223> OTHER INFORMATION: MBP-A53-Q173N DNA coding sequence
<400> SEQUENCE: 10

```
atgaaaatcg aagaaggtaa actggtaatc tggattaacg gcgataaagg ctataacggt       60
ctcgctgaag tcggtaagaa attcgagaaa gataccggaa ttaaagtcac cgttgagcat      120
ccggataaac tggaagagaa attcccacag gttgcgcaa ctggcgatgg ccctgacatt       180
atcttctggg cacacgaccg ctttggtggc tacgctcaat ctggcctgtt ggctgaaatc      240
accccggaca aagcgttcca ggacaagctg tatccgttta cctgggatgc cgtacgttac      300
aacggcaagc tgattgctta cccgatcgct gttgaagcgt atcgctgat ttataacaaa       360
```

```
gatctgctgc cgaacccgcc aaaaacctgg aagagatcc cggcgctgga taagaactg      420 aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga cgcaggtat aacgccgcc agtccgaaca aagagctggc aaaagagttc      840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc      960 actatggaaa acgcccagaa aggtgaaatc atgccgaaca tcccgcagat gtccgctttc    1020
tggtatgccg tgcgtactgc ggtgatcaac gccgccagcg tcgtcagac tgtcgatgaa    1080 gccctgaaag acgcgcagac taattcgagc tcgaacaaca caacaataa caataacaac    1140 aacctcggga tcgagggaag gatttcagaa ttcatcacca acagcggcga tcggatcaat    1200
accgtgcgcg gtcctatcac aatctctgaa gcgggtttca cactgactca cgagcacatc    1260
tgcggcagct cggcaggatt cttgcgtgct tggccggagt tcttcggtag ccgcgcagcc    1320
ctagtggaaa aggctgtgag aggattgcgc gcgccagag cggctggcgt gcgaacgatt    1380
gtcgatgtgt cgactttcga tgccggtcgc gatgtcagtt tattggccga ggtttcgcgg    1440
gctgccgacg ttcatatcgt ggcggcgacc ggcttgtggg aggacccgcc acttcgatg    1500 cggttgagga gtgtagagga actcacacag ttcttcctgc gtgagattca atatggcatc    1560
gaagacaccg gaattagggc gggcattatc aaggtcgcga ccaatggcaa ggcgacccc    1620 tttcaggagt tagtgttaag ggcggccgcc cgggccagct ggccaccgg tgttccggta    1680 accactcaca cgtttgcaag tcagcgcgat ggtgagcagc aggccgccat ttttgagtcc    1740
gaaggcttga gcccctcacg agtttgtatt ggtcacagcg atgatactga cgatttgagc    1800
tatctcaccg ccctcgctgc gcgcggatac ctcatcggtc tagacggcat cccgcacagt    1860
gcgattggtc tagaagataa tgcgagtgca tcagccctcc tgggcaaccg ttcgtggcaa    1920
acacgggctc tcttgatcaa ggcgctcatc gaccaaggct acatgaaaca aatcctcgtt    1980
tcgaatgact ggctgttcgg gttttcgagc tatgtcacca acatcatgga cgtgatggat    2040
agcgtgaacc ccgacgggat ggccttcatt ccactgagag tgatcccatt cctacgagag    2100
aagggcgtcc cacaggaaac gctggcaggc atcactgtga ccaacccggc gcggttcttg    2160
tcaccgacct tgcgggcgtc atga                                            2184
```

<210> SEQ ID NO 11
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 11

```
Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Ala
```

```
            35                  40                  45
Ala Leu Val Glu Lys Ala Val Arg Gly Leu Arg Arg Ala Arg Ala Ala
 50                  55                  60

Gly Val Arg Thr Ile Val Asp Val Ser Thr Phe Asp Ile Gly Arg Asp
 65                  70                  75                  80

Val Ser Leu Leu Ala Glu Val Ser Arg Ala Asp Val His Ile Val
                 85                  90                  95

Ala Ala Thr Gly Leu Trp Glu Asp Pro Pro Leu Ser Met Arg Leu Arg
                100                 105                 110

Ser Val Glu Glu Leu Thr Gln Phe Phe Leu Arg Glu Ile Gln Tyr Gly
                115                 120                 125

Ile Glu Asp Thr Gly Ile Arg Ala Gly Ile Ile Lys Val Ala Thr Asn
                130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Ala Ala Ser
                165                 170                 175

Gln Arg Asp Gly Glu Gln Gln Ala Ala Ile Phe Glu Ser Glu Gly Leu
                180                 185                 190

Ser Pro Ser Arg Val Cys Ile Gly His Ser Asp Asp Thr Asp Asp Leu
                195                 200                 205

Ser Tyr Leu Thr Ala Leu Ala Ala Arg Gly Tyr Leu Ile Gly Leu Asp
                210                 215                 220

Gly Ile Pro His Ser Ala Ile Gly Leu Glu Asp Asn Ala Ser Ala Ser
225                 230                 235                 240

Ala Leu Leu Gly Asn Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
                260                 265                 270

Trp Leu Phe Gly Phe Ser Ser Trp Val Thr Asn Ile Met Asp Val Met
                275                 280                 285

Asp Ser Val Asn Pro Asp Gly Met Ala Phe Ile Pro Leu Arg Val Ile
                290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 12
<211> LENGTH: 1011
<212> TYPE: DNA
<213> ORGANISM: Artificial sequence
<220> FEATURE:
<223> OTHER INFORMATION: polynucleotide sequence encoding seq ID 11

<400> SEQUENCE: 12
atcaccaaca gcggcgatcg gatcaatacc gtgcgcggtc ctatcacaat ctctgaagcg     60
ggtttcacac tgactcacga gcacatctgc ggcagctcgg caggattctt gcgtgcttgg    120
ccggagttct tcggtagccg cgcagcccta gtggaaaagg ctgtgagagg attgcgccgc    180
gccagagcgg ctggcgtgcg aacgattgtc gatgtgtcga ctttcgatat cggtcgcgat    240
gtcagtttat tggccgaggt ttcgcgggct gccgacgttc atatcgtggc ggcgaccggc    300
ttgtgggagg acccgccact ttcgatgcgg ttgaggagtg tagaggaact cacacagttc    360
ttcctgcgtg agattcaata tggcatcgaa gacaccggaa ttagggcggg cattatcaag    420
```

```
gtcgcgacca atggcaaggc gaccccctttt caggagttag tgttaagggc ggccgcccgg     480
gccagcttgg ccaccggtgt tccggtaacc actcacacgg cagcaagtca gcgcgatggt     540
gagcagcagg ccgccatttt tgagtccgaa ggcttgagcc cctcacgagt ttgtattggt     600
cacagcgatg atactgacga tttgagctat ctcaccgccc tcgctgcgcg cggatacctc     660
atcggtctag acggcatccc gcacagtgcg attggtctag aagataatgc gagtgcatca     720
gccctcctgg caaccgttc gtggcaaaca cgggctctct tgatcaaggc gctcatcgac     780
caaggctaca tgaaacaaat cctcgtttcg aatgactggc tgttcgggtt ttcgagctgg     840
gtcaccaaca tcatggacgt gatggatagc gtgaacccg acgggatggc cttcattcca     900
ctgagagtga tcccattcct acgagagaag ggcgtctcac aggaaacgct ggcaggcatc     960
actgtgacca acccgcgcg gttcttgtca ccgaccttgc gggcgtcatg a              1011
```

<210> SEQ ID NO 13
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 13

```
Ile Thr Asn Ser Gly Asp Arg Ile Asn Thr Val Arg Gly Pro Ile Thr
1               5                  10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Gly Ser Arg Ala
        35                  40                  45

Ala Leu Val Glu Lys Ala Val Arg Gly Leu Arg Arg Ala Arg Ala Ala
    50                  55                  60

Gly Val Arg Thr Ile Val Asp Val Ser Thr Phe Asp Ile Gly Arg Asp
65                  70                  75                  80

Val Ser Leu Leu Ala Glu Val Ser Arg Ala Ala Asp Val His Ile Val
                85                  90                  95

Ala Ala Thr Gly Leu Trp Glu Asp Pro Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Asn
    130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Leu Ala Ser
                165                 170                 175

Gln Arg Asp Gly Glu Gln Gln Ala Ala Ile Phe Glu Ser Glu Gly Leu
            180                 185                 190

Ser Pro Ser Arg Val Cys Ile Gly His Ser Asp Asp Thr Asp Asp Leu
        195                 200                 205

Ser Tyr Leu Thr Ala Leu Ala Ala Arg Gly Tyr Leu Ile Gly Leu Asp
    210                 215                 220

Gly Ile Pro His Ser Ala Ile Gly Leu Glu Asp Asn Ala Ser Ala Ser
225                 230                 235                 240

Ala Gly Trp Gly Asn Arg Ser Trp Gln Thr Arg Ala Leu Leu Ile Lys
                245                 250                 255
```

```
Ala Leu Ile Asp Gln Gly Tyr Met Lys Gln Ile Leu Val Ser Asn Asp
            260                 265                 270

Trp Leu Phe Gly Phe Ser Ser Tyr Val Thr Asn Ile Met Asp Val Met
        275                 280                 285

Asp Ser Val Asn Pro Asp Gly Met Ala Phe Ile Pro Leu Arg Val Ile
    290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 14
<211> LENGTH: 1011
<212> TYPE: DNA
<213> ORGANISM: Artificial sequence
<220> FEATURE:
<223> OTHER INFORMATION: polynucleotide sequence encoding seq ID 13

<400> SEQUENCE: 14
atcaccaaca gcggcgatcg gatcaatacc gtgcgcggtc ctatcacaat ctctgaagcg      60
ggtttcacac tgactcacga gcacatctgc ggcagctcgg caggattctt gcgtgcttgg     120
ccggagttct tcggtagccg cgcagcccta gtggaaaagg ctgtgagagg attgcgccgc     180
gccagagcgg ctggcgtgcg aacgattgtc gatgtgtcga ctttcgatat cggtcgcgat     240
gtcagtttat tggccgaggt ttcgcgggct gccgacgttc atatcgtggc ggcgaccggc     300
ttgtgggagg acccgccact ttcgatgcgg ttgaggagtg tagaggaact cacacagttc     360
ttcctgcgtg agattcaata tggcatcgaa gacaccggaa ttagggcggg cattatcaag     420
gtcgcgacca atggcaaggc gacccccttt caggagttag tgttaagggc ggccgcccgg     480
gccagcttgg ccaccggtgt tccggtaacc actcacacgt tggcaagtca gcgcgatggt     540
gagcagcagg ccgccatttt tgagtccgaa ggcttgagcc cctcacgagt ttgtattggt     600
cacagcgatg atactgacga tttgagctat ctcaccgccc tcgctgcgcg cggataccct     660
atcggtctag acggcatccc gcacagtgcg attggtctag aagataatgc gagtgcatca     720
gccggatggg gcaaccgttc gtggcaaaca cgggctctct tgatcaaggc gctcatcgac     780
caaggctaca tgaaacaaat cctcgtttcg aatgactggc tgttcgggtt ttcgagctat     840
gtcaccaaca tcatggacgt gatggatagc gtgaaccccg acgggatggc cttcattcca     900
ctgagagtga tcccattcct acgagagaag ggcgtctcac aggaaacgct ggcaggcatc     960
actgtgacca cccggcgcg gttcttgtca ccgaccttgc gggcgtcatg a              1011

<210> SEQ ID NO 15
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 15

Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Ala
        35                  40                  45

Ala Leu Val Glu Lys Ala Val Arg Gly Leu Arg Arg Ala Arg Ala Ala
```

|   |   |   | 50 |   |   |   | 55 |   |   |   | 60 |   |   |
|---|---|---|---|---|---|---|---|---|---|---|---|---|---|

Gly Val Arg Thr Ile Val Asp Val Ser Thr Phe Asp Ile Gly Arg Asp
 65                  70                  75                  80

Val Ser Leu Leu Ala Glu Val Ser Arg Ala Ala Asp Val His Ile Val
                 85                  90                  95

Ala Ala Thr Gly Leu Trp Glu Asp Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Asn
130                 135                 140

Gly Lys Ala Thr Pro Phe Gln Glu Leu Val Leu Arg Ala Ala Arg
145                 150                 155                 160

Ala Ser Leu Ala Thr Gly Val Pro Val Thr Thr His Thr Leu Ala Ser
                165                 170                 175

Gln Arg Asp Gly Glu Gln Gln Ala Ala Ile Phe Glu Ser Gly Leu
            180                 185                 190

Ser Pro Ser Arg Val Cys Ile Gly His Ser Asp Asp Thr Asp Asp Leu
        195                 200                 205

Ser Tyr Leu Thr Ala Leu Ala Ala Arg Gly Tyr Leu Ile Gly Leu Asp
210                 215                 220

Gly Ile Pro His Ser Ala Ile Gly Leu Glu Asp Asn Ala Ser Ala Ser
225                 230                 235                 240

Ala Arg Leu Gly Asn Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
            260                 265                 270

Trp Leu Phe Gly Phe Ser Ser Tyr Val Thr Asn Ile Met Asp Val Met
        275                 280                 285

Asp Ser Val Asn Pro Asp Gly Met Ala Phe Ile Pro Leu Arg Val Ile
290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 16
<211> LENGTH: 1011
<212> TYPE: DNA
<213> ORGANISM: Artificial sequence
<220> FEATURE:
<223> OTHER INFORMATION: polynucleotide sequence encoding seq ID 15

<400> SEQUENCE: 16
atcaccaaca gcggcgatcg gatcaatacc gtgcgcggtc ctatcacaat ctctgaagcg      60
ggtttcacac tgactcacga gcacatctgc ggcagctcgg caggattctt gcgtgcttgg     120
ccggagttct tcggtagccg cgcagcccta gtggaaaagg ctgtgagagg attgcgccgc     180
gccagagcgg ctggcgtgcg aacgattgtc gatgtgtcga ctttcgatat cggtcgcgat     240
gtcagtttat tggccgaggt ttcgcgggct gccgacgttc atatcgtggc ggcgaccggc     300
ttgtgggagg acccgccact ttcgatgcgg ttgaggagtg tagaggaact cacacagttc     360
ttcctgcgtg agattcaata tggcatcgaa gacaccggaa ttagggcggg cattatcaag     420
gtcgcgacca atggcaaggc gaccccctttt caggagttag tgttaagggc ggccgcccgg     480

```
gccagcttgg ccaccggtgt tccggtaacc actcacacgt tggcaagtca gcgcgatggt    540
gagcagcagg ccgccatttt tgagtccgaa ggcttgagcc cctcacgagt ttgtattggt    600
cacagcgatg atactgacga tttgagctat ctcaccgccc tcgctgcgcg cggatacctc    660
atcggtctag acggcatccc gcacagtgcg attggtctag aagataatgc gagtgcatca    720
gccaggctgg gcaaccgttc gtggcaaaca cgggctctct tgatcaaggc gctcatcgac    780
caaggctaca tgaaacaaat cctcgtttcg aatgactggc tgttcgggtt ttcgagctat    840
gtcaccaaca tcatggacgt gatggatagc gtgaaccccg acgggatggc cttcattcca    900
ctgagagtga tcccattcct acgagagaag ggcgtctcac aggaaacgct ggcaggcatc    960
actgtgacca acccggcgcg gttcttgtca ccgaccttgc gggcgtcatg a            1011
```

<210> SEQ ID NO 17
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 17

```
Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Ala
        35                  40                  45

Ala Leu Val Glu Lys Ala Val Arg Gly Leu Arg Arg Ala Arg Ala Ala
    50                  55                  60

Gly Val Arg Thr Ile Val Asp Val Ser Thr Phe Asp Ile Gly Arg Asp
65                  70                  75                  80

Val Ser Leu Leu Ala Glu Val Ser Arg Ala Ala Asp Val His Ile Val
                85                  90                  95

Ala Ala Thr Gly Leu Trp Glu Asp Pro Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Asn
    130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Ala Ala Ser
                165                 170                 175

Gln Arg Asp Gly Glu Gln Gln Ala Ala Ile Phe Glu Ser Glu Gly Leu
            180                 185                 190

Ser Pro Ser Arg Val Cys Ile Gly His Ser Asp Asp Thr Asp Asp Leu
        195                 200                 205

Ser Tyr Leu Thr Ala Leu Ala Ala Arg Gly Tyr Leu Ile Gly Leu Asp
    210                 215                 220

Gly Ile Pro His Ser Ala Ile Gly Leu Glu Asp Asn Ala Ser Ala Ser
225                 230                 235                 240

Glu Leu Leu Gly Asn Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
            260                 265                 270
```

Trp Leu Phe Gly Phe Ser Ser Trp Val Thr Asn Ile Met Asp Val Met
            275                 280                 285

Asp Ser Val Asn Pro Asp Gly Met Ala Phe Ile Pro Leu Arg Val Ile
        290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 18
<211> LENGTH: 1011
<212> TYPE: DNA
<213> ORGANISM: Artificial sequence
<220> FEATURE:
<223> OTHER INFORMATION: polynucleotide sequence encoding seq ID 17

<400> SEQUENCE: 18

| | |
|---|---|
| atcaccaaca gcggcgatcg gatcaatacc gtgcgcggtc ctatcacaat ctctgaagcg | 60 |
| ggtttcacac tgactcacga gcacatctgc ggcagctcgg caggattctt gcgtgcttgg | 120 |
| ccggagttct tcggtagccg cgcagcccta gtggaaaagg ctgtgagagg attgcgccgc | 180 |
| gccagagcgg ctggcgtgcg aacgattgtc gatgtgtcga ctttcgatat cggtcgcgat | 240 |
| gtcagtttat tggccgaggt ttcgcgggct gccgacgttc atatcgtggc ggcgaccggc | 300 |
| ttgtgggagg acccgccact ttcgatgcgg ttgaggagtg tagaggaact cacacagttc | 360 |
| ttcctgcgtg agattcaata tggcatcgaa gacaccggaa ttagggcggg cattatcaag | 420 |
| gtcgcgacca atggcaaggc gacccccttt caggagttag tgttaagggc ggccgcccgg | 480 |
| gccagcttgg ccaccggtgt tccggtaacc actcacacgg cagcaagtca gcgcgatggt | 540 |
| gagcagcagg ccgccatttt tgagtccgaa ggcttgagcc cctcacgagt ttgtattggt | 600 |
| cacagcgatg atactgacga tttgagctat ctcaccgccc tcgctgcgcg cggataccctc | 660 |
| atcggtctag acggcatccc gcacagtgcg attggtctag aagataatgc gagtgcatca | 720 |
| gaactcctgg gcaaccgttc gtggcaaaca cgggctctct tgatcaaggc gctcatcgac | 780 |
| caaggctaca tgaaacaaat cctcgtttcg aatgactggc tgttcgggtt ttcgagctgg | 840 |
| gtcaccaaca tcatggacgt gatggatagc gtgaaccccg acgggatggc cttcattcca | 900 |
| ctgagagtga tcccattcct acgagagaag ggcgtctcac aggaaacgct ggcaggcatc | 960 |
| actgtgacca acccggcgcg gttcttgtca ccgaccttgc gggcgtcatg a | 1011 |

<210> SEQ ID NO 19
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 19

Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Gly Ser Arg Ala
        35                  40                  45

Ala Leu Val Glu Lys Ala Val Arg Gly Leu Arg Arg Ala Arg Ala Ala
        50                  55                  60

Gly Val Arg Thr Ile Val Asp Val Ser Thr Phe Asp Ile Gly Arg Asp

```
                65                  70                  75                  80
Val Ser Leu Leu Ala Glu Val Ser Arg Ala Ala Asp Val His Ile Val
                    85                  90                  95

Ala Ala Thr Gly Leu Trp Glu Asp Pro Pro Leu Ser Met Arg Leu Arg
                100                 105                 110

Ser Val Glu Glu Leu Thr Gln Phe Phe Leu Arg Glu Ile Gln Tyr Gly
                115                 120                 125

Ile Glu Asp Thr Gly Ile Arg Ala Gly Ile Ile Lys Val Ala Thr Asn
130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Leu Ala Ser
                165                 170                 175

Gln Arg Asp Gly Glu Gln Gln Ala Ala Ile Phe Glu Ser Glu Gly Leu
                180                 185                 190

Ser Pro Ser Arg Val Cys Ile Gly His Ser Asp Asp Thr Asp Asp Leu
                195                 200                 205

Ser Tyr Leu Thr Ala Leu Ala Ala Arg Gly Tyr Leu Ile Gly Leu Asp
210                 215                 220

Gly Ile Pro His Ser Ala Ile Gly Leu Glu Asp Asn Ala Ser Ala Ser
225                 230                 235                 240

Ala Leu Leu Gly Asn Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
                260                 265                 270

Trp Leu Phe Gly Phe Ser Ser Trp Val Thr Asn Ile Met Asp Val Met
                275                 280                 285

Asp Ser Val Asn Pro Asp Gly Met Ala Phe Ile Pro Leu Arg Val Ile
                290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 20
<211> LENGTH: 1011
<212> TYPE: DNA
<213> ORGANISM: Artificial sequence
<220> FEATURE:
<223> OTHER INFORMATION: polynucleotide sequence encoding seq ID 19

<400> SEQUENCE: 20
atcaccaaca gcggcgatcg gatcaatacc gtgcgcggtc ctatcacaat ctctgaagcg      60
ggtttcacac tgactcacga gcacatctgc ggcagctcgg caggattctt gcgtgcttgg     120
ccggagttct tcggtagccg cgcagcccta gtggaaaagg ctgtgagagg attgcgccgc     180
gccagagcgg ctggcgtgcg aacgattgtc gatgtgtcga ctttcgatat cggtcgcgat     240
gtcagtttat tggccgaggt ttcgcgggct gccgacgttc atatcgtggc ggcgaccggc     300
ttgtgggagg acccgccact ttcgatgcgg ttgaggagtg tagaggaact cacacagttc     360
ttcctgcgtg agattcaata tggcatcgaa gacaccggaa ttagggcggg cattatcaag     420
gtcgcgacca atggcaaggc gaccccctt caggagttag tgttaagggc ggccgcccgg     480
gccagcttgg ccaccggtgt tccggtaacc actcacacgt tggcaagtca gcgcgatggt     540
gagcagcagg ccgccatttt tgagtccgaa ggcttgagcc cctcacgagt tgtattggt      600
```

```
cacagcgatg atactgacga tttgagctat ctcaccgccc tcgctgcgcg cggatacctc    660
atcggtctag acggcatccc gcacagtgcg attggtctag aagataatgc gagtgcatca    720
gccctcctgg caaccgttc gtggcaaaca cgggctctct tgatcaaggc gctcatcgac     780
caaggctaca tgaaacaaat cctcgtttcg aatgactggc tgttcgggtt ttcgagctgg    840
gtcaccaaca tcatggacgt gatggatagc gtgaacccccg acgggatggc cttcattcca   900
ctgagagtga tcccattcct acgagagaag ggcgtctcac aggaaacgct ggcaggcatc    960
actgtgacca acccggcgcg gttcttgtca ccgaccttgc gggcgtcatg a            1011
```

<210> SEQ ID NO 21
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 21

```
Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Ala
        35                  40                  45

Ala Leu Val Glu Lys Ala Val Arg Gly Leu Arg Arg Ala Arg Ala Ala
    50                  55                  60

Gly Val Arg Thr Ile Val Asp Val Ser Thr Phe Asp Ala Gly Arg Asp
65                  70                  75                  80

Val Ser Leu Leu Ala Glu Val Ser Arg Ala Ala Asp Val His Ile Val
                85                  90                  95

Ala Ala Thr Gly Leu Trp Glu Asp Pro Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Asn
    130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Ala Ala Ser
                165                 170                 175

Gln Arg Asp Gly Glu Gln Gln Ala Ala Ile Phe Glu Ser Glu Gly Leu
            180                 185                 190

Ser Pro Ser Arg Val Cys Ile Gly His Ser Asp Asp Thr Asp Asp Leu
        195                 200                 205

Ser Tyr Leu Thr Ala Leu Ala Ala Arg Gly Tyr Leu Ile Gly Leu Asp
    210                 215                 220

Gly Ile Pro His Ser Ala Ile Gly Leu Glu Asp Asn Ala Ser Ala Ser
225                 230                 235                 240

Ala Leu Leu Gly Asn Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
            260                 265                 270

Trp Leu Phe Gly Phe Ser Ser Tyr Val Thr Asn Ile Met Asp Val Met
        275                 280                 285
```

```
Asp Ser Val Asn Pro Asp Gly Met Ala Phe Ile Pro Leu Arg Val Ile
        290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 22
<211> LENGTH: 1011
<212> TYPE: DNA
<213> ORGANISM: Artificial sequence
<220> FEATURE:
<223> OTHER INFORMATION: polynucleotide sequence encoding seq ID 21

<400> SEQUENCE: 22
atcaccaaca gcggcgatcg gatcaatacc gtgcgcggtc ctatcacaat ctctgaagcg      60
ggtttcacac tgactcacga gcacatctgc ggcagctcgg caggattctt gcgtgcttgg     120
ccggagttct tcggtagccg cgcagcccta gtggaaaagg ctgtgagagg attgcgccgc     180
gccagagcgg ctggcgtgcg aacgattgtc gatgtgtcga ctttcgatgc cggtcgcgat     240
gtcagtttat tggccgaggt ttcgcgggct gccgacgttc atatcgtggc ggcgaccggc     300
ttgtgggagg acccgccact ttcgatgcgg ttgaggagtg tagaggaact cacacagttc     360
ttcctgcgtg agattcaata tggcatcgaa gacaccggaa ttagggcggg cattatcaag     420
gtcgcgacca atggcaaggc gaccccttt caggagttag tgttaagggc ggccgcccgg     480
gccagcttgg ccaccggtgt tccggtaacc actcacacgg cagcaagtca gcgcgatggt     540
gagcagcagg ccgccatttt tgagtccgaa ggcttgagcc cctcacgagt ttgtattggt     600
cacagcgatg atactgacga tttgagctat ctcaccgccc tcgctgcgcg cggataccta     660
atcggtctag acggcatccc gcacagtgcg attggtctag aagataatgc gagtgcatca     720
gccctcctgg caaccgttc gtggcaaaca cgggctctct tgatcaaggc gctcatcgac     780
caaggctaca tgaaacaaat cctcgtttcg aatgactggc tgttcgggtt ttcgagctat     840
gtcaccaaca tcatggacgt gatggatagc gtgaaccccg acgggatggc cttcattcca     900
ctgagagtga tcccattcct acgagagaag ggcgtcccac aggaaacgct ggcaggcatc     960
actgtgacca acccggcgcg gttcttgtca ccgaccttgc gggcgtcatg a              1011

<210> SEQ ID NO 23
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 23

Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
                20                  25                  30

Ser Ala Gly Phe Leu Arg Ala Trp Pro Glu Phe Phe Gly Ser Arg Ala
            35                  40                  45

Ala Leu Val Glu Lys Ala Val Arg Gly Leu Arg Arg Ala Arg Ala Ala
        50                  55                  60

Gly Val Arg Thr Ile Val Asp Val Ser Thr Phe Asp Ala Gly Arg Asp
65                  70                  75                  80

Val Ser Leu Leu Ala Glu Val Ser Arg Ala Ala Asp Val His Ile Val
```

|  |  |  |  | 85 |  |  |  |  | 90 |  |  |  |  | 95 |  |
|---|---|---|---|---|---|---|---|---|---|---|---|---|---|---|---|

Ala Ala Thr Gly Leu Trp Glu Asp Pro Pro Leu Ser Met Arg Leu Arg
                    100                 105                 110

Ser Val Glu Glu Leu Thr Gln Phe Phe Leu Arg Glu Ile Gln Tyr Gly
            115                 120                 125

Ile Glu Asp Thr Gly Ile Arg Ala Gly Ile Ile Lys Val Ala Thr Asn
        130                 135                 140

Gly Lys Ala Thr Pro Phe Gln Glu Leu Val Leu Arg Ala Ala Arg
145                 150                 155                 160

Ala Ser Leu Ala Thr Gly Val Pro Val Thr Thr His Thr Leu Ala Ser
                165                 170                 175

Gln Arg Asp Gly Glu Gln Gln Ala Ala Ile Phe Glu Ser Glu Gly Leu
            180                 185                 190

Ser Pro Ser Arg Val Cys Ile Gly His Ser Asp Thr Asp Asp Leu
        195                 200                 205

Ser Tyr Leu Thr Ala Leu Ala Ala Arg Gly Tyr Leu Ile Gly Leu Asp
        210                 215                 220

Gly Ile Pro His Ser Ala Ile Gly Leu Glu Asp Asn Ala Ser Ala Ser
225                 230                 235                 240

Ala Leu Leu Gly Asn Arg Ser Trp Gln Thr Arg Ala Leu Leu Ile Lys
                245                 250                 255

Ala Leu Ile Asp Gln Gly Tyr Met Lys Gln Ile Leu Val Ser Asn Asp
                260                 265                 270

Trp Leu Phe Gly Phe Ser Ser Tyr Val Thr Asn Ile Met Asp Val Met
        275                 280                 285

Asp Ser Val Asn Pro Asp Gly Met Ala Phe Ile Pro Leu Arg Val Ile
        290                 295                 300

Pro Phe Leu Arg Glu Lys Gly Val Pro Gln Glu Thr Leu Ala Gly Ile
305                 310                 315                 320

Thr Val Thr Asn Pro Ala Arg Phe Leu Ser Pro Thr Leu Arg Ala Ser
                325                 330                 335

<210> SEQ ID NO 24
<211> LENGTH: 1011
<212> TYPE: DNA
<213> ORGANISM: Artificial sequence
<220> FEATURE:
<223> OTHER INFORMATION: polynucleotide sequence encoding seq ID 23

<400> SEQUENCE: 24

| atcaccaaca gcggcgatcg gatcaatacc gtgcgcggtc ctatcacaat ctctgaagcg | 60 |
|---|---|
| ggtttcacac tgactcacga gcacatctgc ggcagctcgg caggattctt cgtgcttgg | 120 |
| ccggagttct tcggtagccg cgcagcccta gtggaaaagg ctgtgagagg attgcgccgc | 180 |
| gccagagcgg ctggcgtgcg aacgattgtc gatgtgtcga cttctgatgc cggtcgcgat | 240 |
| gtcagtttat tggccgaggt ttcgcgggct gccgacgttc atatcgtggc ggcgaccggc | 300 |
| tgtgggagg acccgccact ttcgatgcgg ttgaggagtg tagaggaact cacacagttc | 360 |
| ttcctgcgtg agattcaata tggcatcgaa gacaccggaa ttagggcggg cattatcaag | 420 |
| gtcgcgacca atggcaaggc gaccccttt caggagttag tgttaagggc ggccgcccgg | 480 |
| gccagcttgg ccaccggtgt tccggtaacc actcacacgt tggcaagtca gcgcgatggt | 540 |
| gagcagcagg ccgccatttt tgagtccgaa ggcttgagcc cctcacgagt ttgtattggt | 600 |
| cacagcgatg atactgacga tttgagctat ctcaccgccc tcgctgcgcg cggataccte | 660 |

```
atcggtctag acggcatccc gcacagtgcg attggtctag aagataatgc gagtgcatca    720
gccctcctgg gcaaccgttc gtggcaaaca cgggctctct tgatcaaggc gctcatcgac    780
caaggctaca tgaaacaaat cctcgtttcg aatgactggc tgttcgggtt ttcgagctat    840
gtcaccaaca tcatggacgt gatggatagc gtgaacccg acgggatggc cttcattcca     900
ctgagagtga tcccattcct acgagagaag ggcgtcccac aggaaacgct ggcaggcatc    960
actgtgacca acccggcgcg gttcttgtca ccgaccttgc gggcgtcatg a            1011
```

<210> SEQ ID NO 25
<211> LENGTH: 332
<212> TYPE: PRT
<213> ORGANISM: Artificial Sequence
<220> FEATURE:
<223> OTHER INFORMATION: genetically modified polypeptide

<400> SEQUENCE: 25

```
Gly Asp Arg Ile Asn Thr Val Arg Gly Pro Ile Thr Ile Ser Glu Leu
1               5                   10                  15

Gly Phe Thr Leu Met His Glu His Ile Cys Gly Ser Ser Ala Gly Phe
            20                  25                  30

Leu Arg Ala Trp Pro Glu Phe Phe Gly Ser Arg Ala Ala Leu Val Glu
        35                  40                  45

Lys Ala Val Arg Gly Leu Arg Arg Ala Arg Ala Gly Val Asp Thr
    50                  55                  60

Ile Val Asp Val Ser Thr Phe Asp Ile Gly Arg Asp Val Glu Leu Leu
65                  70                  75                  80

Ala Glu Val Ala Glu Ala Ala Asp Val His Ile Val Ala Ala Thr Gly
                85                  90                  95

Leu Trp Glu Asp Pro Pro Leu Ser Met Arg Leu Arg Ser Val Glu Glu
            100                 105                 110

Leu Thr Gln Phe Phe Leu Arg Glu Ile Gln Tyr Gly Ile Glu Asp Thr
        115                 120                 125

Gly Ile Arg Ala Gly Ile Ile Lys Val Ala Thr Asn Gly Lys Ala Thr
    130                 135                 140

Pro Phe Gln Glu Arg Val Leu Arg Ala Ala Arg Ala Ser Leu Glu
145                 150                 155                 160

Thr Gly Val Pro Val Thr Thr His Thr Asp Ala Ser Gln Arg Asp Gly
                165                 170                 175

Glu Glu Gln Ala Asp Ile Phe Glu Ser Glu Gly Leu Asp Pro Ser Arg
            180                 185                 190

Val Cys Ile Gly His Ala Asp Thr Asp Leu Asp Tyr Leu Thr
        195                 200                 205

Glu Leu Ala Ala Arg Gly Tyr Leu Ile Gly Leu Asp Gly Ile Pro His
    210                 215                 220

Ser Ala Ile Gly Leu Glu Asp Asn Ala Ser Ala Ala Leu Leu Gly
225                 230                 235                 240

Asn Arg Ser Trp Gln Thr Arg Ala Leu Leu Ile Lys Ala Leu Ile Asp
                245                 250                 255

Gln Gly Tyr Ala Asp Gln Ile Leu Val Ser Asn Asp Trp Leu Phe Gly
            260                 265                 270

Phe Ser Ser Trp Val Thr Asn Ile Met Asp Val Met Asp Ser Val Asn
        275                 280                 285

Pro Asp Gly Met Ala His Ile Pro Glu Arg Val Ile Pro Phe Leu Arg
    290                 295                 300
```

Glu Lys Gly Val Pro Asp Glu Thr Leu Asp Thr Ile Met Val Glu Asn
305                 310                 315                 320

Pro Ala Arg Phe Leu Ser Pro Thr Leu Arg Ala Ser
                325                 330

<210> SEQ ID NO 26
<211> LENGTH: 1049
<212> TYPE: DNA
<213> ORGANISM: Artificial sequence
<220> FEATURE:
<223> OTHER INFORMATION: polynucleotide sequence encoding seq ID 25

<400> SEQUENCE: 26
ggaaggattt cagaattcat caccaacagc ggcgaccgta tcaacaccgt tcgtggtccg        60
atcaccatct ctgagctggg tttcacccctg atgcacgaac acatctgcgg ttcttctgcg      120
ggtttcctgc gcgcgtggcc ggaattttc ggttctcgtg cggcgctggt tgagaaagcg       180
gttcgcggtc tgcgtcgtgc ccgtgctgct ggtgtcgata ccatcgttga cgtttctacc      240
tttgatatcg gtcgtgacgt tgaactgctg gcggaggttg ccgaggcagc ggacgttcac      300
atcgtagctg ccaccggtct gtgggaagac ccaccgctgt ctatgcgtct gcgctctgtt      360
gaagaactga cccaattctt cctccgtgag atccagtacg gtattgagga caccggtatc      420
cgtgcgggta tcatcaaagt tgcgaccaac ggtaaagcga ccccgttcca ggaacgcgta      480
ctccgtgccg ctgcgcgtgc gtctctggaa actggtgtac cggttactac ccacaccgac      540
gcctctcagc gtgacggtga agagcaagcg gacatctttg agtctgaagg cctggacccg      600
tctcgcgttt gcatcggtca cgcggacgat accgacgacc tggactatct gacggaactg      660
gcggctcgcg gctacctgat tggtctggac ggcatcccgc actctgcgat cggcctcgaa      720
gacaacgctt ctgctgccgc cctcctgggt aatcgttctt ggcagactcg tgctctgctg      780
atcaaagcgc tgatcgacca gggctatgcg gaccagatcc tggtttctaa cgactggctg      840 ttcggttct ctctcttgggt taccaacatt atggacgtta tggattctgt taacccggac      900
ggtatggcgc acatccctga acgtgtgatc ccgtttctgc gtgaaaaagg tgttccggac      960
gaaaccctgg acaccatcat ggtagagaac ccggcacgtt ttctctctcc gacgctccgc     1020
gcgtcttgat aactgcaggc aagcttggc                                        1049

<210> SEQ ID NO 27
<211> LENGTH: 332
<212> TYPE: PRT
<213> ORGANISM: Artificial Sequence
<220> FEATURE:
<223> OTHER INFORMATION: genetically modified polypeptide

<400> SEQUENCE: 27

Gly Asp Arg Ile Asn Thr Val Arg Gly Pro Ile Thr Ile Ser Glu Ala
1               5                   10                  15

Gly Phe Thr Leu Met His Glu His Ile Cys Gly Ser Ser Ala Gly Phe
                20                  25                  30

Leu Arg Ala Trp Pro Glu Phe Phe Gly Ser Arg Ala Ala Leu Val Glu
            35                  40                  45

Lys Ala Val Arg Gly Leu Arg Arg Ala Arg Ala Gly Val Arg Thr
        50                  55                  60

Ile Val Asp Val Ser Thr Phe Asp Ile Gly Arg Asp Val Glu Leu Leu
65                  70                  75                  80

Ala Glu Val Ser Glu Ala Ala Asp Val His Ile Val Ala Ala Thr Gly
                85                  90                  95

Leu Trp Glu Asp Pro Pro Leu Ser Met Arg Leu Arg Ser Val Glu Glu
            100                 105                 110

Leu Thr Gln Phe Phe Leu Arg Glu Ile Gln Tyr Gly Ile Glu Asp Thr
            115                 120                 125

Gly Ile Arg Ala Gly Ile Ile Lys Val Ala Thr Asn Gly Lys Ala Thr
130                 135                 140

Pro Phe Gln Glu Arg Val Leu Arg Ala Ala Arg Ala Ser Leu Ala
145                 150                 155                 160

Thr Gly Val Pro Val Thr Thr His Thr Asp Ala Ser Gln Arg Asp Gly
                165                 170                 175

Glu Gln Gln Ala Asp Ile Phe Glu Ser Glu Gly Leu Asp Pro Ser Arg
            180                 185                 190

Val Cys Ile Gly His Ser Asp Asp Thr Asp Asp Leu Asp Tyr Leu Thr
            195                 200                 205

Ala Leu Ala Ala Arg Gly Tyr Leu Ile Gly Leu Asp Gly Ile Pro His
            210                 215                 220

Ser Ala Ile Gly Leu Glu Asp Asn Ala Ser Ala Ala Leu Leu Gly
225                 230                 235                 240

Asn Arg Ser Trp Gln Thr Arg Ala Leu Leu Ile Lys Ala Leu Ile Asp
                245                 250                 255

Gln Gly Tyr Ala Asp Gln Ile Leu Val Ser Asn Asp Trp Leu Phe Gly
            260                 265                 270

Phe Ser Ser Trp Val Thr Asn Ile Met Asp Val Met Asp Ser Val Asn
            275                 280                 285

Pro Asp Gly Met Ala Phe Ile Pro Leu Arg Val Ile Pro Phe Leu Arg
            290                 295                 300

Glu Lys Gly Val Pro Asp Glu Thr Leu Glu Thr Ile Met Val Asp Asn
305                 310                 315                 320

Pro Ala Arg Phe Leu Ser Pro Thr Leu Arg Ala Ser
                325                 330

<210> SEQ ID NO 28
<211> LENGTH: 1049
<212> TYPE: DNA
<213> ORGANISM: Artificial sequence
<220> FEATURE:
<223> OTHER INFORMATION: polynucleotide sequence encoding seq ID 27

<400> SEQUENCE: 28
ggaaggattt cagaattcat caccaacagc ggcgaccgta tcaacaccgt acgtggtccg     60
atcaccatct ccgaagcggg tttcaccctg atgcacgaac acatctgcgg ttcttctgcg    120
ggcttcctcc gcgcttggcc ggagttcttt ggttctcgcg ctgctctggt tgaaaaagcg    180
gttcgtggtc tgcgtcgtgc tcgtgctgcc ggtgtgcgta ccatcgttga cgtttctacc    240
ttcgacattg gcgcgatgt cgagctgctc gccgaagttt ctgaagcggc ggacgttcat    300
attgttgcgg caaccggtct gtgggaggac cctccgctgt ctatgcgcct ccgttctgtt    360
gaagagctca cccagttttt tctccgcgaa atccagtacg gtatcgaaga cactggtatc    420
cgtgcgggta tcatcaaagt tgcgaccaac ggtaaagcaa ccccgttcca ggaacgtgtt    480
ctccgtgcag cagcccgtgc gtctctggcg accggcgttc cggtcaccac ccacaccgac    540
gcttctcagc gtgacggtga acagcaggcg gacatcttcg aatctgaagg cctcgacccg    600
tctcgtgttt gcatcggtca ttctgatgac acggacgacc tggactacct gaccgcgctg    660
gccgctcgtg gttatctcat tggtctggac ggcattccgc attctgcgat cggcctggaa    720

```
gacaacgcgt ctgcggctgc actgctgggt aaccgttctt ggcagacccg tgccctgctg    780
atcaaagcgc tgatcgacca gggttacgcg gaccagatcc tggtttctaa cgactggctg    840
ttcggtttct cttcttgggt taccaacatc atggacgtta tggactctgt taacccggac    900
ggtatggcgt tcatcccact ccgtgtgatc ccttttctgc gtgagaaggg tgttccggat    960
gaaactctgg agacgattat ggttgacaac ccggcacgtt ttctgtctcc gactctgcgc    1020
gcgtcttgat aactgcaggc aagcttggc    1049
```

<210> SEQ ID NO 29
<211> LENGTH: 332
<212> TYPE: PRT
<213> ORGANISM: Artificial Sequence
<220> FEATURE:
<223> OTHER INFORMATION: genetically modified polypeptide

<400> SEQUENCE: 29

```
Gly Asp Arg Ile Asn Thr Val Arg Gly Pro Ile Thr Ile Ser Glu Ala
1               5                   10                  15

Gly Phe Thr Leu Thr His Glu His Ile Cys Gly Ser Ser Ala Gly Phe
            20                  25                  30

Leu Arg Ala Trp Pro Glu Phe Phe Gly Ser Arg Ala Ala Leu Val Glu
        35                  40                  45

Lys Ala Val Arg Gly Leu Arg Arg Ala Arg Ala Ala Gly Val Arg Thr
    50                  55                  60

Ile Val Asp Val Ser Thr Phe Asp Ile Gly Arg Asp Val Ser Leu Leu
65                  70                  75                  80

Ala Glu Val Ser Glu Ala Ala Asp Val His Ile Val Ala Ala Thr Gly
                85                  90                  95

Leu Trp Glu Asp Pro Pro Leu Ser Met Arg Leu Arg Ser Val Glu Glu
            100                 105                 110

Leu Thr Gln Phe Phe Leu Arg Glu Ile Gln Tyr Gly Ile Glu Asp Thr
        115                 120                 125

Gly Ile Arg Ala Gly Ile Ile Lys Val Ala Thr Asn Gly Lys Ala Thr
    130                 135                 140

Pro Phe Gln Glu Leu Val Leu Arg Ala Ala Arg Ala Ser Leu Ala
145                 150                 155                 160

Thr Gly Val Pro Val Thr Thr His Thr Asp Ala Ser Gln Arg Asp Gly
                165                 170                 175

Glu Gln Gln Ala Ala Ile Phe Glu Ser Glu Gly Leu Asp Pro Ser Arg
            180                 185                 190

Val Cys Ile Gly His Ser Asp Asp Thr Asp Asp Leu Asp Tyr Leu Thr
        195                 200                 205

Ala Leu Ala Ala Arg Gly Tyr Leu Ile Gly Leu Asp Gly Ile Pro His
    210                 215                 220

Ser Ala Ile Gly Leu Glu Asp Asn Ala Ser Ala Ser Ala Leu Leu Gly
225                 230                 235                 240

Asn Arg Ser Trp Gln Thr Arg Ala Leu Leu Ile Lys Ala Leu Ile Asp
                245                 250                 255

Gln Gly Tyr Val Lys Gln Ile Leu Val Ser Asn Asp Trp Leu Phe Gly
            260                 265                 270

Phe Ser Ser Trp Val Thr Asn Ile Met Asp Val Met Asp Ser Val Asn
        275                 280                 285

Pro Asp Gly Met Ala Phe Ile Pro Leu Arg Val Ile Pro Phe Leu Arg
    290                 295                 300
```

Glu Lys Gly Val Pro Gln Glu Thr Leu Ala Thr Ile Thr Val Glu Asn
305                 310                 315                 320

Pro Ala Arg Phe Leu Ser Pro Thr Leu Arg Ala Ser
            325                 330

<210> SEQ ID NO 30
<211> LENGTH: 1049
<212> TYPE: DNA
<213> ORGANISM: Artificial sequence
<220> FEATURE:
<223> OTHER INFORMATION: polynucleotide sequence encoding seq ID 29

<400> SEQUENCE: 30

```
ggaaggattt cagaattcat caccaacagc ggcgaccgta tcaacaccgt ccgtggtccg      60
atcaccatct ctgaggcggg cttcaccctg actcacgaac acatttgcgg ttctagcgca     120
ggttttctgc gcgcttggcc ggagtttttc ggttctcgtg ctgctctggt ggaaaaagcg     180
gttcgtggcc tgcgtcgtgc gcgtgcggct ggtgtgcgta ccatcgttga cgtttctacc     240
ttcgacattg gtcgtgatgt ttctctgctg gccgaggttt ctgaagcggc cgatgttcac     300
attgttgcag cgactggtct gtgggaagat ccgccgctgt ctatgcgtct gcgctctgtt     360
gaagaactca cccagttctt tctccgtgaa atccagtacg gcatcgagga cacgggtatc     420
cgtgccggta tcattaaagt tgccaccaac ggtaaagcga cccgtttca ggaactggtt      480
ctgcgtgcag cagctcgtgc ctccctcgcc accggcgttc cggtcaccac ccacaccgac     540
gcttctcagc gtgacggtga acagcaggcg gcgatcttcg aaagcgaagg tctggacccg     600
tctcgtgttt gtatcggtca ctctgacgac accgatgatc tggactacct gaccgcgctc     660
gcggctcgtg gttacctgat tggcctggat ggtattccgc actctgcgat cggcctcgaa     720
gacaacgcat ctgcgtccgc tctgctcggt aatcgctctt ggcagacccg tgcgctgctg     780
atcaaagcgc tgatcgacca gggctacgtt aaacagatcc tggtttctaa cgattggctg     840
ttcggttttt cttcttgggt taccaacatc atggacgtta tggactctgt taacccagac     900
ggtatggcgt tcatcccgct gcgtgttatc ccgttcctgc gcgagaaagg tgttccacaa     960
gagacgctgg cgaccatcac cgttgaaaac cctgctcgtt tcctgtctcc aaccctccgt    1020
gcttcttgat aactgcaggc aagcttggc                                      1049
```

<210> SEQ ID NO 31
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 31

Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Ala
        35                  40                  45

Ala Leu Val Glu Lys Ala Val Arg Gly Leu Arg Arg Ala Arg Ala Ala
    50                  55                  60

Gly Val Arg Thr Ile Val Asp Val Ser Thr Phe Asp Ile Gly Arg Asp
65                  70                  75                  80

Val Ser Leu Leu Ala Glu Val Ser Glu Ala Ala Asp Val His Ile Val

```
                   85                  90                  95
Ala Ala Thr Gly Leu Trp Glu Asp Pro Pro Leu Ser Met Arg Leu Arg
                100                 105                 110

Ser Val Glu Glu Leu Thr Gln Phe Phe Leu Arg Glu Ile Gln Tyr Gly
            115                 120                 125

Ile Glu Asp Thr Gly Ile Arg Ala Gly Ile Ile Lys Val Ala Thr Asn
        130                 135                 140

Gly Lys Ala Thr Pro Phe Gln Glu Leu Val Leu Arg Ala Ala Arg
145                 150                 155                 160

Ala Ser Leu Ala Thr Gly Val Pro Val Thr Thr His Thr Asp Ala Ser
                165                 170                 175

Gln Arg Asp Gly Glu Gln Gln Ala Ala Ile Phe Glu Ser Glu Gly Leu
            180                 185                 190

Asp Pro Ser Arg Val Cys Ile Gly His Ser Asp Thr Asp Leu
        195                 200                 205

Asp Tyr Leu Thr Ala Leu Ala Ala Arg Gly Tyr Leu Ile Gly Leu Asp
        210                 215                 220

Gly Ile Pro His Ser Ala Ile Gly Leu Glu Asp Asn Ala Met Ala Ser
225                 230                 235                 240

Ser Trp Leu Gly Asn Arg Ser Trp Gln Thr Arg Ala Leu Leu Ile Lys
                245                 250                 255

Ala Leu Ile Asp Gln Gly Tyr Val Lys Gln Ile Leu Val Ser Asn Asp
            260                 265                 270

Trp Leu Phe Gly Phe Ser Ser Trp Val Thr Asn Ile Met Asp Val Met
        275                 280                 285

Asp Ser Val Asn Pro Asp Gly Met Ala Phe Ile Pro Leu Arg Val Ile
        290                 295                 300

Pro Phe Leu Arg Glu Lys Gly Val Pro Gln Glu Thr Leu Ala Thr Ile
305                 310                 315                 320

Thr Val Glu Asn Pro Ala Arg Phe Leu Ser Pro Thr Leu Arg Ala Ser
                325                 330                 335

<210> SEQ ID NO 32
<211> LENGTH: 1011
<212> TYPE: DNA
<213> ORGANISM: Artificial sequence
<220> FEATURE:
<223> OTHER INFORMATION: polynucleotide sequence encoding seq ID 31

<400> SEQUENCE: 32
atcaccaaca gcggcgaccg tatcaacacc gtccgtggtc cgatcaccat ctctgaggcg      60
ggcttcaccc tgactcacga acacatttgc ggttctagcg caggttttct gcgcgcttgg    120
ccggagtttt tcggttctcg tgctgctctg gtggaaaaag cggttcgtgg cctgcgtcgt    180
gcgcgtgcgg ctggtgtgcg taccatcgtt gacgtttcta ccttcgacat tggtcgtgat    240
gtttctctgc tggccgaggt ttctgaagcg gccgatgttc acattgttgc agcgactggt    300
ctgtgggaag atccgccgct gtctatgcgt ctgcgctctg ttgaagaact cacccagttc    360
tttctccgtg aaatccagta cggcatcgag gacacgggta ccgtgccgg tatcattaaa     420 gttgccacca cggtaaagc gaccccgttt caggaactgg ttctgcgtgc agcagctcgt     480
gcctccctcg ccaccggcgt tccggtcacc acccacaccg acgcttctca gcgtgacggt    540
gaacagcagg cggcgatctt cgaaagcgaa ggtctggacc cgtctcgtgt ttgtatcggt    600
cactctgacg acaccgatga tctggactac ctgaccgcgc tcgcggctcg tggttacctg    660
```

```
attggcctgg atggtattcc gcactctgcg atcggcctcg aagacaacgc aatggcgtcc    720
agctggctcg gtaatcgctc ttggcagacc cgtgcgctgc tgatcaaagc gctgatcgac    780
cagggctacg ttaaacagat cctggttttct aacgattggc tgttcggttt ttcttcttgg    840
gttaccaaca tcatggacgt tatggactct gttaacccag acggtatggc gttcatcccg    900
ctgcgtgtta tcccgttcct gcgcgagaaa ggtgttccac aagagacgct ggcgaccatc    960
accgttgaaa accctgctcg tttcctgtct ccaaccctcc gtgcttcttg a             1011
```

<210> SEQ ID NO 33
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 33

```
Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
                20                  25                  30

Ser Ala Gly Phe Leu Arg Ala Trp Pro Glu Phe Phe Gly Ser Arg Ala
            35                  40                  45

Ala Leu Val Glu Lys Ala Val Arg Gly Leu Arg Arg Ala Arg Ala Ala
        50                  55                  60

Gly Val Arg Thr Ile Val Asp Val Ser Thr Phe Asp Ile Gly Arg Asp
65                  70                  75                  80

Val Ser Leu Leu Ala Glu Val Ser Glu Ala Ala Asp Val His Ile Val
                85                  90                  95

Ala Ala Thr Gly Leu Trp Glu Asp Pro Pro Leu Ser Met Arg Leu Arg
            100                 105                 110

Ser Val Glu Glu Leu Thr Gln Phe Phe Leu Arg Glu Ile Gln Tyr Gly
        115                 120                 125

Ile Glu Asp Thr Gly Ile Arg Ala Gly Ile Ile Lys Val Ala Thr Asn
130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Asp Ala Ser
                165                 170                 175

Gln Arg Asp Gly Glu Gln Gln Ala Ala Ile Phe Glu Ser Glu Gly Leu
            180                 185                 190

Asp Pro Ser Arg Val Cys Ile Gly His Ser Asp Asp Thr Asp Asp Leu
        195                 200                 205

Asp Tyr Leu Thr Ala Leu Ala Ala Arg Gly Tyr Leu Ile Gly Leu Asp
210                 215                 220

Gly Ile Pro His Ser Ala Ile Gly Leu Glu Asp Asn Ala Arg Ala Ser
225                 230                 235                 240

Ser Trp Leu Gly Asn Arg Ser Trp Gln Thr Arg Ala Leu Leu Ile Lys
                245                 250                 255

Ala Leu Ile Asp Gln Gly Tyr Val Lys Gln Ile Leu Val Ser Asn Asp
            260                 265                 270

Trp Leu Phe Gly Phe Ser Ser Trp Val Thr Asn Ile Met Asp Val Met
        275                 280                 285

Asp Ser Val Asn Pro Asp Gly Met Ala Phe Ile Pro Leu Arg Val Ile
290                 295                 300
```

```
Pro Phe Leu Arg Glu Lys Gly Val Pro Gln Glu Thr Leu Ala Thr Ile
305                 310                 315                 320

Thr Val Glu Asn Pro Ala Arg Phe Leu Ser Pro Thr Leu Arg Ala Ser
            325                 330                 335
```

<210> SEQ ID NO 34
<211> LENGTH: 1011
<212> TYPE: DNA
<213> ORGANISM: Artificial sequence
<220> FEATURE:
<223> OTHER INFORMATION: polynucleotide sequence encoding seq ID 33

<400> SEQUENCE: 34

```
atcaccaaca gcggcgaccg tatcaacacc gtccgtggtc cgatcaccat ctctgaggcg    60
ggcttcaccc tgactcacga acacatttgc ggttctagcg caggttttct gcgcgcttgg   120
ccggagtttt tcggttctcg tgctgctctg gtggaaaaag cggttcgtgg cctgcgtcgt   180
gcgcgtgcgg ctggtgtgcg taccatcgtt gacgtttcta ccttcgacat tggtcgtgat   240
gtttctctgc tggccgaggt ttctgaagcg gccgatgttc acattgttgc agcgactggt   300
ctgtgggaag atccgccgct gtctatgcgt ctgcgctctg ttgaagaact cacccagttc   360
tttctccgtg aaatccagta cggcatcgag gacacgggta ccgtgccgg tatcattaaa    420
gttgccacca acggtaaagc gaccccgttt caggaactgg ttctgcgtgc agcagctcgt   480
gcctccctcg ccaccggcgt tccggtcacc acccacaccg acgcttctca gcgtgacggt   540
gaacagcagg cggcgatctt cgaaagcgaa ggtctggacc cgtctcgtgt ttgtatcggt   600
cactctgacg acaccgatga tctggactac ctgaccgcgc tcgcggctcg tggttacctg   660
attggcctgg atggtattcc gcactctgcg atcggcctcg aagacaacgc aagggcgtcc   720
agctggctcg gtaatcgctc ttggcagacc cgtgcgctgc tgatcaaagc gctgatcgac   780
cagggctacg ttaaacagat cctggttttct aacgattggc tgttcggttt ttcttcttgg   840
gttaccaaca tcatggacgt tatggactct gttaacccag acggtatggc gttcatcccg   900
ctgcgtgtta tcccgttcct gcgcgagaaa ggtgttccac aagagacgct ggcgaccatc   960
accgttgaaa accctgctcg tttcctgtct ccaaccctcc gtgcttcttg a           1011
```

<210> SEQ ID NO 35
<211> LENGTH: 336
<212> TYPE: PRT
<213> ORGANISM: Artificial Sequence
<220> FEATURE:
<223> OTHER INFORMATION: genetically modified polypeptide

<400> SEQUENCE: 35

```
Ile Thr Asn Ser Gly Asp Arg Ile Asn Thr Val Arg Gly Pro Ile Thr
1               5                   10                  15

Ile Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Ala
        35                  40                  45

Ala Leu Val Glu Lys Ala Val Arg Gly Leu Arg Arg Ala Arg Ala Ala
    50                  55                  60

Gly Val Arg Thr Ile Val Asp Val Ser Thr Phe Asp Ile Gly Arg Asp
65                  70                  75                  80

Val Ser Leu Leu Ala Glu Val Ser Glu Ala Ala Asp Val His Ile Val
                85                  90                  95

Ala Ala Thr Gly Leu Trp Glu Asp Pro Pro Leu Ser Met Arg Leu Arg
```

```
            100                 105                 110
Ser Val Glu Glu Leu Thr Gln Phe Phe Leu Arg Glu Ile Gln Tyr Gly
            115                 120                 125

Ile Glu Asp Thr Gly Ile Arg Ala Gly Ile Ile Lys Val Ala Thr Asn
        130                 135                 140

Gly Lys Ala Thr Pro Phe Gln Glu Leu Val Leu Arg Ala Ala Ala Arg
145                 150                 155                 160

Ala Ser Leu Ala Thr Gly Val Pro Val Thr Thr His Thr Asp Ala Ser
                165                 170                 175

Gln Arg Asp Gly Glu Gln Gln Ala Ala Ile Phe Glu Ser Glu Gly Leu
            180                 185                 190

Asp Pro Ser Arg Val Cys Ile Gly His Ser Asp Asp Thr Asp Asp Leu
        195                 200                 205

Asp Tyr Leu Thr Ala Leu Ala Ala Arg Gly Tyr Leu Ile Gly Leu Asp
    210                 215                 220

Gly Ile Pro His Ser Ala Ile Gly Leu Glu Asp Asn Ala Arg Ala Ser
225                 230                 235                 240

Asp Trp Leu Gly Asn Arg Ser Trp Gln Thr Arg Ala Leu Leu Ile Lys
                245                 250                 255

Ala Leu Ile Asp Gln Gly Tyr Val Lys Gln Ile Leu Val Ser Asn Asp
            260                 265                 270

Trp Leu Phe Gly Phe Ser Ser Trp Val Thr Asn Ile Met Asp Val Met
        275                 280                 285

Asp Ser Val Asn Pro Asp Gly Met Ala Phe Ile Pro Leu Arg Val Ile
    290                 295                 300

Pro Phe Leu Arg Glu Lys Gly Val Pro Gln Glu Thr Leu Ala Thr Ile
305                 310                 315                 320

Thr Val Glu Asn Pro Ala Arg Phe Leu Ser Pro Thr Leu Arg Ala Ser
                325                 330                 335

<210> SEQ ID NO 36
<211> LENGTH: 1011
<212> TYPE: DNA
<213> ORGANISM: Artificial sequence
<220> FEATURE:
<223> OTHER INFORMATION: polynucleotide sequence encoding seq ID 35

<400> SEQUENCE: 36
atcaccaaca gcggcgaccg tatcaacacc gtccgtggtc cgatcaccat ctctgaggcg      60
ggcttcaccc tgactcacga acacatttgc ggttctagcg caggttttct gcgcgcttgg    120
ccggagtttt tcggttctcg tgctgctctg gtggaaaaag cggttcgtgg cctgcgtcgt    180
gcgcgtgcgg ctggtgtgcg taccatcgtt gacgtttcta ccttcgacat tggtcgtgat    240
gtttctctgc tggccgaggt ttctgaagcg gccgatgttc acattgttgc agcgactggt    300
ctgtgggaag atccgccgct gtctatgcgt ctgcgctctg ttgaagaact cacccagttc    360
tttctccgtg aaatccagta cggcatcgag gacacgggta ccgtgccgg tatcattaaa     420 gttgccacca acggtaaagc gaccccgttt caggaactgg ttctgcgtgc agcagctcgt    480
gcctccctcg ccaccggcgt tccggtcacc cccacaccg acgcttctca gcgtgacggt     540
gaacagcagg cggcgatctt cgaaagcgaa ggtctggacc cgtctcgtgt ttgtatcggt    600
cactctgacg acaccgatga tctggactac ctgaccgcgc tcgcggctcg tggttacctg    660
attggcctgg atggtattcc gcactctgcg atcggcctcg aagacaacgc aagggcgtcc    720
gattggctcg gtaatcgctc ttggcagacc cgtgcgctgc tgatcaaagc gctgatcgac    780
```

```
caggyctacg ttaaacagat cctggtttct aacgattggc tgttcggttt ttcttcttgg    840
gttaccaaca tcatggacgt tatggactct gttaacccag acggtatggc gttcatcccg    900
ctgcgtgtta tcccgttcct gcgcgagaaa ggtgttccac aagagacgct ggcgaccatc    960
accgttgaaa accctgctcg tttcctgtct ccaaccctcc gtgcttcttg a            1011
```

ISOLATED PHOSPHOTRIESTERASE POLYPEPTIDES, POLYNUCLEOTIDES ENCODING SAME AND USES THEREOF IN TREATING OR PREVENTING ORGANOPHOSPHATE EXPOSURE ASSOCIATED DAMAGE

RELATED APPLICATIONS

This application is a National Phase of PCT Patent Application No. PCT/IL2015/051203 having International filing date of Dec. 10, 2015, which claims the benefit of priority under 35 USC § 119(e) of U.S. Provisional Patent Application No. 62/090,411 filed on Dec. 11, 2014. The contents of the above applications are all incorporated by reference as if fully set forth herein in their entirety.

SEQUENCE LISTING STATEMENT

The ASCII file, entitled 70238SequenceListing.txt, created on Jun. 11, 2017, comprising 102,403 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to phosphotriesterase (PTE) enzymes capable of hydrolyzing nerve gases and, more particularly, but not exclusively, to V-type nerve gases.

At present, both prophylaxis and post-intoxication treatments of chemical warfare nerve agent (CWNA) poisoning are based on drugs selected to counteract the symptoms caused by accumulation of acetylcholine in cholinergic neurons. Current antidotal régimes consist of pretreatment with pyridostigmine, and of post-exposure therapy that involves administration of a cocktail containing atropine, an oxime reactivator and an anticonvulsant drug such as diazepam. The multi-drug approach against CWNA toxicity has been adopted by many countries and integrated into their civil and military medical doctrines. However, it is commonly recognized that these drug régimes suffer from several disadvantages that call for new therapeutic strategies. The preferred approach is to rapidly detoxify the CWNA in the blood before it has had the chance to reach its physiological targets. One way of achieving this objective is by the use of bioscavengers. However, use of the best stoichiometric bioscavenger currently available (human butyrylcholinesterase, hBChE) requires administration of hundreds of milligrams of protein to confer protection against toxic doses of CWNA. A safer and more effective treatment strategy can be achieved by using a catalytic bioscavenger to rapidly degrade the intoxicating OP in the circulation.

The promiscuous nerve-agent hydrolyzing activities of the enzyme phosphotriesterase (PTE) make it a prime candidate both for prophylactic and post exposure treatment of nerve-agent intoxications. However, efficient in-vivo detoxification using low doses of enzymes (≤50 mg/70 kg) following exposure to toxic doses of nerve agents, requires that their catalytic efficiencies (kcat/KM) towards the toxic nerve agent isomers will be increased.

PTE variants that can efficiently hydrolyze V-type nerve agents are disclosed in Cherney et al, 2013, ACS Chem Biol 8: 2394-2403. In-vivo post-exposure activity of one of these variant was demonstrated in guinea-pigs intoxicated with a lethal dose of VX (Worek et al, 2014, Toxicol Lett 231: 45-54).

Additional background art includes U.S. Pat. No. 8,735,124.

SUMMARY OF THE INVENTION

According to an aspect of the present invention, there is provided a genetically modified polypeptide comprising an amino acid sequence of phosphotriesterase (PTE) having at least twice the catalytic efficiency for a V-type nerve agent as a polypeptide which consists of the sequence as set forth in SEQ ID NO: 1, when assayed at 25° C. under identical conditions.

According to an aspect of the present invention, there is provided a genetically modified polypeptide comprising an amino acid sequence of phosphotriesterase (PTE) having catalytic efficiency $k_{cat}/K_M$ greater than $3 \cdot 10^6 M^{-1}$ min$^{-1}$ for the Sp isomer of RVX, retaining at least 50% of its catalytic activity at 50° C. as its catalytic activity at 25° C., when measured in a cell lysate.

According to an aspect of the present invention, there is provided a method of detoxifying a surface, the method comprising contacting the surface with the isolated polypeptide described herein, thereby detoxifying the surface.

According to an aspect of the present invention, there is provided an isolated polypeptide comprising an amino acid sequence of PTE having catalytic efficiency of $k_{cat}/K_M \approx 10^6 \cdot 5 \cdot 10^7$ M$^{-1}$ min$^{-1}$ for a V-type organophosphate, wherein the amino acid sequence comprises each of the mutations F132E, T173N, H254G, A203L, K77A, A80V, G208D and I274N.

According to an aspect of the present invention, there is provided an isolated polypeptide comprising an amino acid sequence of PTE having catalytic efficiency of $k_{cat}/K_M \approx 10^6 \cdot 5 \cdot 10^7$ M$^{-1}$ min$^{-1}$ for a V-type organophosphate, wherein the amino acid sequence comprises the mutations T173N, I106A, F132E, A203F, H254G, K77A, A80V, G208D and I274N.

According to an aspect of the present invention, there is provided a genetically modified polypeptide comprising an amino acid sequence at least 99% homologous to the sequence as set forth in SEQ ID NO: 2, 3, 4, 8, 11, 13, 15, 17, 19, 21, 23, 25, 27, 29, 31, 33, or 35.

According to an aspect of the present invention, there is provided an isolated polynucleotide comprising a nucleic acid sequence encoding the polypeptide described herein.

According to an aspect of the present invention, there is provided a pharmaceutical composition comprising as an active ingredient the isolated polypeptide described herein and a pharmaceutically acceptable carrier.

According to an aspect of the present invention, there is provided a nucleic acid construct comprising the isolated polynucleotide described herein and a cis-regulatory element driving expression of the polynucleotide.

According to an aspect of the present invention, there is provided a method of treating an organophosphate exposure associated damage in a subject, comprising administering to the subject a therapeutically effective amount of the isolated polypeptide described herein.

According to an aspect of the present invention, there is provided an article of manufacture for treating or preventing organophosphate exposure associated damage, the article of manufacture comprising the isolated polypeptide described herein immobilized on to a solid support.

According to an aspect of the present invention, there is provided an isolated polypeptide comprising the amino acid sequence as set forth in SEQ ID NO: 2, 3, 4, 8, 11, 13, 15, 17, 19, 21, 23, 25, 27, 29, 31, 33, or 35.

According to embodiments of the present invention, the V-type nerve agent comprises a Sp isomer.

According to embodiments of the present invention, the V-type nerve agent is selected from the group consisting of VX, RVX and CVX.

According to embodiments of the present invention, the V-type nerve agent is the Sp isomer of VX.

According to embodiments of the present invention, the catalytic activity in the presence of 50 μM of the metal chelator 1,10 phenantroline is at least 50% of its catalytic activity in the absence of the metal chelator.

According to embodiments of the present invention, the amino acid sequence of PTE comprises the mutation A203L.

According to embodiments of the present invention, the amino acid sequence of PTE comprises the mutation Y309W.

According to embodiments of the present invention, the amino acid of PTE at position 271 is glycine or arginine.

According to embodiments of the present invention, the amino acid sequence of PTE further comprises the mutation L272W.

According to embodiments of the present invention, the amino acid sequence of PTE further comprises the mutation A270E and/or A203L.

According to embodiments of the present invention, the amino acid sequence of PTE comprises the mutations F132E, T173N, H254G and A203L.

According to embodiments of the present invention, the amino acid sequence of PTE comprises the mutation T173N.

According to embodiments of the present invention, the amino acid at position 203 of the polypeptide is alanine.

According to embodiments of the present invention, the amino acid at position 203 of the polypeptide is phenylalanine.

According to embodiments of the present invention, the amino acid sequence of PTE comprises the mutation T173N, I106A, F132E and H254G.

According to embodiments of the present invention, the modified polypeptide further comprises the mutation A203F or A203L.

According to embodiments of the present invention, the amino acid sequence of PTE comprises the mutation T173Q, I106A, F132E and H254G.

According to embodiments of the present invention, the amino acid sequence of PTE further comprises the mutations K77A, A80V, G208D and I274N.

According to embodiments of the present invention, the polypeptide further comprises the mutation P342S.

According to embodiments of the present invention, the genetically modified polypeptide is expressed in bacteria.

According to embodiments of the present invention, the genetically modified polypeptide comprises an amino acid sequence at least 99% homologous to the sequence as set forth in SEQ ID NO: 2, 3, 11, 13, 15, 17, 19, 25, 27, 29, 31, 33 or 35.

According to embodiments of the present invention, the genetically modified polypeptide comprises an amino acid sequence at least 99% homologous to the sequence as set forth in SEQ ID NO: 4, 8, 21 or 23.

According to embodiments of the present invention, the solid support is for topical administration.

According to embodiments of the present invention, the solid support for topical administration is selected from the group consisting of a sponge, a wipe and a fabric.

According to embodiments of the present invention, the solid support is selected from the group consisting of a filter, a fabric and a lining.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 illustrates the docking of VX into the structure of PTE variant C23.

FIG. 2 illustrates the docking of RVX into the structure of PTE variant C23.

FIG. 3 is a bar graph illustrating the thermal stability of PTE variants, wt S5, C23, and A53.

FIG. 4 is a bar graph illustrating metal chelation with 50 μM 1,10 phenantroline.

FIG. 5 is a bar graph illustrating thermal stability of A53 variants obtained by site-directed mutagenesis. Control is at 25° C.

FIG. 6 is a bar graph illustrating metal chelation studies (50 μM 1,10 phenantroline) with variants obtained by site-directed mutagenesis of A53. Control is without chelator.

FIG. 7 is a bar graph illustrating the cell lysate paraoxonase activity of particular variants performed at room temperature.

FIG. 8 is a bar graph illustrating the room temperature activities measured following a 5-6 hour incubation in the absence of Zinc.

FIG. 9 represents the average residual activity after 30 minute incubation with 50 μM 1,10-orthophenanthroline of particular variants. Error bars denote the S.D. for all replicas of each clone from two individual experiments.

FIG. 10 is a bar graph illustrating the thermal activity of particular variants.

FIG. 11 is a bar graph illustrating the cell lysate paraoxonase activity of particular variants performed at room temperature in the presence and absence of zinc.

Figure 1:
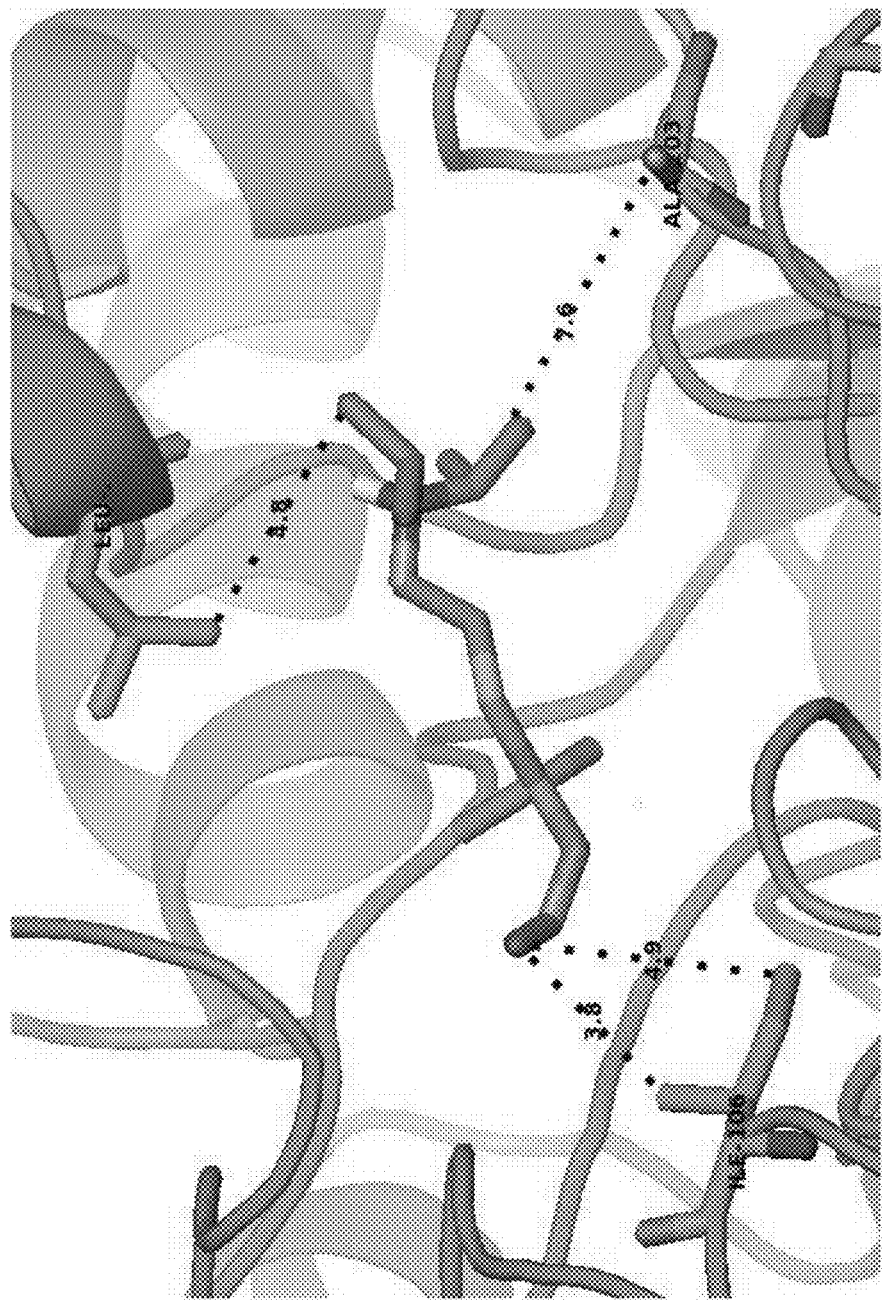

FIG. 12 is a bar graph illustrating the thermal activity of particular variants in the presence and absence of zinc.

DESCRIPTION OF SPECIFIC EMBODIMENTS OF THE INVENTION

The present invention, in some embodiments thereof, relates to phosphotriesterase (PTE) enzymes capable of hydrolyzing nerve gases and, more particularly, but not exclusively, to V-type nerve gases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The promiscuous nerve-agent hydrolyzing activities of the enzyme phosphotriesterase (PTE) make it a prime candidate both for prophylactic and post exposure treatment of nerve-agent intoxications. However, efficient in-vivo detoxification using low doses of enzymes (≤50 mg/70 kg) following exposure to toxic doses of nerve agents, requires that their catalytic efficiencies ($k_{cat}/K_M$) towards the toxic nerve agent isomers will be greater than $1\times10^7$ M−1min−1.

Previously the present inventors generated PTE variants whose activity against the three major V-type nerve agents (VX, RVX and CVX) was improved 500-5000 fold relative to wt PTE (Cherny et al, 2013, ACS Chem Biol 8: 2394-2403). However, these variants were not sufficiently active for clinical use. This was manifested in in-vivo experiments which were performed, where a dose of 5 mg/Kg of the evolved PTE variant C23 was needed in order to provide effective post-exposure protection from VX (Worek et al, 2014, Toxicol Lett 231: 45-54). Post-intoxication survival was improved also by treatment with a lower dose of C23 (2.5 mg/Kg) but was accompanied by severe intoxication symptoms (Worek et al, 2014, Toxicol Lett 231: 45-54). These results warranted additional enhancement of the catalytic activities of PTE in order to obtain variants that could serve as lead compounds for further drug development.

The present inventors have now found that two additional mutations (A203L and Y309W) carried out on the previously disclosed C23 mutant (Cherny et al, 2013, ACS Chem Biol 8: 2394-2403) increased its catalytic activity by approximately 2.5 fold.

Further, an additional mutation (Q173N) carried out on the previously disclosed A53 mutant enhanced the stability of the protein.

In addition, an F203A mutation carried out on the previously disclosed A53 mutant also enhanced the stability of the protein.

Using the A53 and the C23 mutants as starting points additional mutants were generated having enhanced catalytic activities and/or stabilities.

Thus, according to one aspect of the invention there is provided a genetically modified polypeptide comprising an amino acid sequence of phosphotriesterase (PTE) having at least twice the catalytic efficiency for a V-type nerve agent as a polypeptide which consists of the sequence as set forth in SEQ ID NO: 1, when assayed at 25° C. under identical conditions.

As used herein, the term "phosphotriesterase", also referred to as Parathion hydrolase (EC: 3.1.8.1), refers to an enzyme belonging to the amidohydrolase superfamily. The phosphotriesterases of this aspect of the present invention are bacterial phosphotriesterases that have an enhanced catalytic activity towards V-type organophosphonates due to an extended loop 7 amino acid sequence, as compared to other phosphotriesterases. Such phosphotriesterases have been identified in *Brevundimonas diminuta, Flavobacterium* sp. (PTEflavob) and *Agrobacterium* sp.

According to one embodiment the protein on which modifications are performed may comprise a sequence as set forth SEQ ID NO: 5.

In a specific embodiment the enzyme is expressible in *E. Coli*. In this embodiment, the protein on which modifications are performed may comprise a sequence as set forth in SEQ ID NO: 6 or SEQ ID NO: 7.

As used herein, a "nerve agent" refers to an organophosphate (OP) compound such as having an acetylcholinesterase inhibitory activity. The toxicity of an OP compound depends on the rate of its inhibition of acetylcholinesterase with the concomitant release of the leaving group such as fluoride, alkylthiolate, cyanide or aryoxy group. The nerve agent may be a racemic composition or a purified enantiomer (e.g., Sp or Rp). According to this aspect of the present invention the nerve agent is a V-type nerve agent (e.g., VX, CVX or RVX).

According to another embodiment, the variant has at least twice the catalytic efficiency for the Sp isomer of a V type nerve agent as a polypeptide which consists of the sequence as set forth in SEQ ID NO: 1, when assayed under identical conditions.

According to another embodiment, the variant has at least twice the catalytic efficiency for the Sp isomer of V-X as a polypeptide which consists of the sequence as set forth in SEQ ID NO: 1, when assayed under identical conditions.

Methods of measuring catalytic efficiency of the variants described herein are known in the art and include for example measuring the release of thiol leaving group using the Ellman's reagent dithionitrobenzoic acid (DTNB) following incubation with the PTE variants, or by measuring the rate of loss of AChE inhibition upon incubation of racemic OPs with the PTE variants. Both of these methods are further described in the Examples section herein below.

Catalytic activities may be accurately compared when the same assay method is used, under the same experimental conditions (temperature, time etc.). In order to minimize differences in experimental conditions, it is preferable that the catalytic activities of the test polypeptide and control (SEQ ID NO: 1, also referred to herein as C23) are measured at substantially the same time (e.g. during the same experiment) and using the same stock solutions.

According to an embodiment of this aspect of the present invention, the test polypeptide has at least 1.8. 1.9. 2. 2.1, 2.2, 2.3, 2.4, 2.5, 2.6, 2.7, 2.8, 2.9, 3, 4, 5, 6, 7, 8, 9 or even 10 times the catalytic efficiency for a V-type nerve agent as a polypeptide which consists of the sequence as set forth in SEQ ID NO: 1, when assayed at 25° C., under identical conditions.

Methods of selecting PTE polypeptides with the desired activity are provided in the Examples section below. Typically, these methods involve directed evolution of PTE using structure-based as well as random mutagenesis, and combining low-throughput methodologies (96-well plate screening) with high-throughput screens e.g., using compartmentalization in emulsions.

As used herein the phrase "in vitro evolution process" (also referred to as "a directed evolution process") refers to the mutagenesis and/or recombination of genes and selection or screening of a desired activity. A number of methods which can be utilized to effect in vitro evolution, are known in the art. One approach of executing the in-vitro evolution process is provided in the Examples section.

General outline of directed evolution is provided in Tracewell C A, Arnold F H "Directed enzyme evolution: climbing fitness peaks one amino acid at a time" Curr Opin Chem Biol. 2009 February; 13(1):3-9. Epub 2009 Feb. 25; Gerlt J A, Babbitt P C, Curr Opin Chem Biol. 2009 February; 13(1):10-8. Epub 2009 Feb. 23 and WO2004/078991 (either of which is hereby incorporated by reference in its entirety).

Methods of producing recombinant proteins are well known in the art and are further described herein below.

According to a specific embodiment, a mutation which may be employed to improve the hydrolytic efficiency of PTE to V-type nerve agent substrates comprises the mutation A203L where the coordinates corresponds to the PTE having the sequence (SEQ ID NO: 5) having the Uniprot number P0A434. Amino acid coordinates should be adapted easily to PTE variants of the same or other species by amino acid sequence alignments which may be done manually or using specific bioinformatic tools such as FASTA, L-ALIGN and protein Blast.

According to another specific embodiment, mutations which may be employed to improve the hydrolytic efficiency of PTE to V-type nerve agent substrates comprise the mutations F132E, T173N, H254G and A203L where the coordinates corresponds to the PTE having the sequence (SEQ ID NO: 5) having the Uniprot number P0A434.

According to another specific embodiment, mutations which may be employed to improve the hydrolytic efficiency of PTE to V-type nerve agent substrates comprise the mutations F132E, T173N, H254G and Y309W where the coordinates corresponds to the PTE having the sequence (SEQ ID NO: 5) having the Uniprot number P0A434.

According to another specific embodiment, mutations which may be employed to improve the hydrolytic efficiency of PTE to V-type nerve agent substrates comprise the mutations F132E, T173N, H254G, A203L, L271G and L272W where the coordinates corresponds to the PTE having the sequence (SEQ ID NO: 5) having the Uniprot number P0A434.

According to another specific embodiment, mutations which may be employed to improve the hydrolytic efficiency of PTE to V-type nerve agent substrates comprise the mutations F132E, T173N, H254G, A203L and L271R where the coordinates corresponds to the PTE having the sequence (SEQ ID NO: 5) having the Uniprot number P0A434.

According to another specific embodiment, mutations which may be employed to improve the hydrolytic efficiency of PTE to V-type nerve agent substrates comprise the mutations F132E, T173N, H254G, A270E and Y309W where the coordinates corresponds to the PTE having the sequence (SEQ ID NO: 5) having the Uniprot number P0A434.

According to another specific embodiment, mutations which may be employed to improve the hydrolytic efficiency of PTE to V-type nerve agent substrates comprise the mutations F132E, T173N, H254G, A203L and Y309W where the coordinates corresponds to the PTE having the sequence (SEQ ID NO: 5) having the Uniprot number P0A434.

Additional contemplated mutations in combinations with the contemplated mutations include K77A, A80V, G208D and I274N, where the coordinates corresponds to the PTE having the sequence (SEQ ID NO: 5) having the Uniprot number P0A434.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 203 is L and not replaceable where the coordinates corresponds to the PTE having the sequence (SEQ ID NO: 5) having the Uniprot number P0A434.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NOs: 5 or 11 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 309 is W and not replaceable where the coordinates corresponds to the PTE having the sequence (SEQ ID NO: 5) having the Uniprot number P0A434. This polypeptide is referred to herein as Y309W.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 13 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 203 is L and not replaceable, the amino acid at position 271 is G and not replaceable, the amino acid at position 272 is W and not replaceable, where the coordinates corresponds to the PTE having the sequence (SEQ ID NO: 5) having the Uniprot number P0A434. This polypeptide is referred to herein as A203 L/L271G/L272W.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 15 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 203 is L and not replaceable, the amino acid at position 271 is R and not replaceable where the coordinates corresponds to the PTE having the sequence (SEQ ID NO: 5) having the Uniprot number P0A434. This polypeptide is referred to herein as A203L/L271R.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 17 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 270 is E and not replaceable and the amino acid at position 309 is W and not replaceable where the coordinates corresponds to the PTE having the sequence (SEQ ID NO: 5) having the Uniprot number P0A434. This polypeptide is referred to herein as Y309W/A270E.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 19 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 203 is L and not replaceable and the amino acid at position 309 is W and not replaceable where the coordinates corresponds to the PTE having the sequence (SEQ ID NO: 5) having the Uniprot number P0A434. This polypeptide is referred to herein as Y309W/A203L.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 as determined using the Standard protein-protein BLAST [blastp] software of the NCBI, wherein the amino acid at position 77 is A and not replaceable, wherein the amino acid at position 80 is V and not replaceable, wherein the amino acid at position 132 is E and not replaceable, the amino acid at position 173 is N and not replaceable, the amino acid at position 254 is G and not replaceable and the amino acid at position 203 is L and not replaceable, wherein the amino acid at position 208 is D and not replaceable, wherein the amino acid at position 274 is N and not replaceable, where the coordinates corresponds to the PTE having the sequence (SEQ ID NO: 5) having the Uniprot number P0A434.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 as determined using the Standard protein-protein BLAST [blastp] software of the NCBI, wherein the amino acid at position 77 is A and not replaceable, wherein the amino acid at position 80 is V and not replaceable, wherein the amino acid at position 132 is E and not replaceable, the amino acid at position 173 is N and not replaceable, the amino acid at position 254 is G and not replaceable and the amino acid at position 203 is L and not replaceable, wherein the amino acid at position 208 is D and not replaceable, wherein the amino acid at position 274 is N and not replaceable, wherein the amino acid at position 342 is S and not replaceable, where the coordinates corresponds to the PTE having the sequence (SEQ ID NO: 5) having the Uniprot number P0A434.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 29 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 95 is E and not replaceable, the amino acid at position 180 is D and not replaceable, the amino acid at position 199 is D and not replaceable, the amino acid at position 215 is D and not replaceable, the amino acid at position 270 is V and not replaceable, the amino acid at position 325 is T and not replaceable, and the amino acid at position 329 is E and not replaceable, where the coordinates corresponds to the PTE having the sequence (SEQ ID NO: 5) having the Uniprot number P0A434. This sequence is referred to herein as m2p0.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 27 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 31 is M and not replaceable, the amino acid at position 88 is E and not replaceable, the amino acid at position 95 is E and not replaceable, the amino acid at position 159 is R and not replaceable, the amino acid at position 180 is D and not replaceable, the amino acid at position 191 is D and not replaceable, the amino acid at position 199 is D and not replaceable, the amino acid at position 215 is D and not replaceable, the amino acid at position 246 is A and not replaceable, the amino acid at position 270 is A and not replaceable, the amino acid at position 271 is D and not replaceable, the amino acid at position 320 is D and not replaceable, the amino acid at position 324 is E and not replaceable, the amino acid at position 325 is T and not replaceable, the amino acid at position 327 is M and not replaceable, and the amino acid at position 329 is D and not replaceable, where the coordinates corresponds to the PTE having the sequence (SEQ ID NO: 5) having the Uniprot number P0A434. This sequence is referred to herein as m0p95.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 25 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 26 is L and not replaceable, the amino acid at position 31 is M and not replaceable, the amino acid at position 73 is D and not replaceable, the amino acid at position 88 is E and not replaceable, the amino acid at position 94 is A and not replaceable, the amino acid at position 95 is E and not replaceable, the amino acid at position 159 is R and not replaceable, the amino acid at position 170 is E and not replaceable, the amino acid at position 180 is D and not replaceable, the amino acid at position 188 is E and not replaceable, the amino acid at position 191 is D and not replaceable, the amino acid at position 199 is D and not replaceable, the amino acid at position 208 is A and not replaceable, the amino acid at position 215 is D and not replaceable, the amino acid at position 219 is E and not replaceable, the amino acid at position 246 is A and not replaceable, the amino acid at position 270 is A and not replaceable, the amino acid at position 271 is D and not replaceable, the amino acid at position 304 is H and not replaceable, the amino acid at position 307 is E and not replaceable, the amino acid at position 320 is D and not replaceable, the amino acid at position 324 is D and not replaceable, the amino acid at position 325 is T and not replaceable, the amino acid at position 327 is M and not replaceable, and the amino acid at position 329 is E and not replaceable, where the coordinates corresponds to the PTE having the sequence (SEQ ID NO: 5) having the Uniprot number P0A434. This sequence is referred to herein as m0p45.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 33 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 95 is E and not replaceable, the amino acid at position 180 is D and not replaceable, the amino acid at position 199 is D and not replaceable, the amino acid at position 215 is D and not replaceable, the amino acid at position 270 is V and not replaceable, the amino acid at position 325 is T and not replaceable, the amino acid at position 329 is E and not replaceable, the amino acid at position 267 is R and not replaceable, the amino acid at position 270 is S and not replaceable, and the amino acid at position 271 is W and not replaceable where the coordinates corresponds to the PTE having the sequence (SEQ ID NO: 5) having the Uniprot number P0A434. This sequence is referred to herein as 3B11.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 35 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 95 is E and not replaceable, the amino acid at position 180 is D and not replaceable, the amino acid at position 199 is D and not replaceable, the amino acid at position 215 is D and not replaceable, the amino acid at position 270 is V and not replaceable, the amino acid at position 325 is T and not replaceable, the amino acid at position 329 is E and not replaceable, the amino acid at position 267 is R and not replaceable, the amino acid at position 270 is D and not replaceable, and the amino acid at position 271 is W and not replaceable where the coordinates corresponds to the PTE having the sequence (SEQ ID NO: 5) having the Uniprot number P0A434. This sequence is referred to herein as 6C12.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 31 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 95 is E and not replaceable, the amino acid at position 180 is D and not replaceable, the amino acid at position 199 is D and not replaceable, the amino acid at position 215 is D and not replaceable, the amino acid at position 270 is V and not replaceable, the amino acid at position 325 is T and not replaceable, the amino acid at position 329 is E and not replaceable, the amino acid at position 267 is M and not replaceable, the amino acid at position 270 is S and not replaceable, and the amino acid at position 271 is W and not replaceable where the coordinates corresponds to the PTE having the sequence (SEQ ID NO: 5) having the Uniprot number P0A434. This sequence is referred to herein as 4E11.

The polypeptides of this aspect of the present invention are preferably expressible in bacteria such as *E. coli* [e.g., BL21, BL21 (DE3), Origami B (DE3), available from Novagen (www(dot)calbiochem(dot)com) and RIL (DE3) available from Stratagene, (www(dot)stratagene(dot)com). Essentially, at least 2%, at least 5%, at least 10%, at least 20%, at least 30%, at least 40%, at least 50%, at least 60%, at least 70%, at least 80%, at least 90%, at least 95% or more, say 100%, of bacterially expressed protein remains soluble (i.e., does not precipitate into inclusion bodies).

The present inventors have found that removal of the first 29 amino acids of the PTE aided in the successful expression in bacteria.

Thus, the present inventors contemplate any of the polypeptides and homologues thereof described herein above devoid of the first 29 amino acids of PTE. Since the first 29 amino acids of SEQ ID NO: 5 have been removed in the polypeptide of SEQ ID NO: 6, the first amino acid of SEQ ID NO: 6 is numbered 30, the second amino acid of SEQ ID NO: 6 is numbered 31 etc. with respect to the numbering of the positions of the mutations.

For example, according to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 203 is L and not replaceable where the coordinates corresponds to the PTE having the sequence (SEQ ID NO: 5) having the Uniprot number P0A434. Since the first 29 amino acids of SEQ ID NO: 5 have been removed in the polypeptide of SEQ ID NO: 6, the first amino acid of SEQ ID NO: 6 is numbered 30, the second amino acid of SEQ ID NO: 6 is numbered 31 etc. with respect to the numbering of the positions of the mutations.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 77 is A and not replaceable, wherein the amino acid at position 80 is V and not replaceable, wherein the amino acid at position 132 is E and not replaceable, the amino acid at position 173 is N and not replaceable, the amino acid at position 254 is G and not replaceable and the amino acid at position 203 is L and not replaceable, wherein the amino acid at position 208 is D and not replaceable, wherein the amino acid at position 274 is N and not replaceable, where the coordinates corresponds to the PTE having the sequence (SEQ ID NO: 5) having the Uniprot number P0A434.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 77 is A and not replaceable, wherein the amino acid at position 80 is V and not replaceable, wherein the amino acid at position 132 is E and not replaceable, the amino acid at position 173 is N and not replaceable, the amino acid at position 254 is G and not replaceable and the amino acid at position 203 is L and not replaceable, wherein the amino acid at position 208 is D and not replaceable, wherein the amino acid at position 274 is N and not replaceable, wherein the amino acid at position 342 is S and not replaceable, where the coordinates corresponds to the PTE having the sequence (SEQ ID NO: 5) having the Uniprot number P0A434.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 309 is W and not replaceable where the coordinates corresponds to the PTE having the sequence (SEQ ID NO: 5) having the Uniprot number P0A434. This polypeptide is referred to herein as Y309W.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 203 is L and not replaceable, the amino acid at position 271 is G and not replaceable, the amino acid at position 272 is W and not replaceable, where the coordinates corresponds to the PTE having the sequence (SEQ ID NO: 5) having the Uniprot number P0A434. This polypeptide is referred to herein as A203 L/L271G/L272W.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 203 is L and not replaceable, the amino acid at position 271 is R and not replaceable where the coordinates corresponds to the PTE having the sequence (SEQ ID NO: 5) having the Uniprot number P0A434. This polypeptide is referred to herein as A203 L/L271R.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable and the amino acid at position 270 is E and not replaceable and the amino acid at position 309 is W and not replaceable where the coordinates corresponds to the PTE having the sequence (SEQ ID NO: 5) having the Uniprot number P0A434. This polypeptide is referred to herein as Y309W/A270E.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 203 is L and not replaceable and the amino acid at position 309 is W and not replaceable where the coordinates corresponds to the PTE having the sequence (SEQ ID NO: 5) having the Uniprot number P0A434. This polypeptide is referred to herein as Y309W/A203L.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 95 is E and not replaceable, the amino acid at position 180 is D and not replaceable, the amino acid at position 199 is D and not replaceable, the amino acid at position 215 is D and not replaceable, the amino acid at position 270 is V and not replaceable, the amino acid at position 325 is T and not replaceable, and the amino acid at position 329 is E and not replaceable, where the coordinates corresponds to the PTE having the sequence (SEQ ID NO: 5) having the Uniprot number P0A434. This sequence is referred to herein as m2p0.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 31 is M and not replaceable, the amino acid at position 88 is E and not replaceable, the amino acid at position 95 is E and not replaceable, the amino acid at position 159 is R and not replaceable, the amino acid at position 180 is D and not replaceable, the amino acid at position 191 is D and not replaceable, the amino acid at position 199 is D and not replaceable, the amino acid at position 215 is D and not replaceable, the amino acid at position 246 is A and not replaceable, the amino acid at position 270 is A and not replaceable, the amino acid at position 271 is D and not replaceable, the amino acid at position 320 is D and not replaceable, the amino acid at position 324 is E and not replaceable, the amino acid at position 325 is T and not replaceable, the amino acid at position 327 is M and not replaceable, and the amino acid at position 329 is D and not replaceable, where the coordinates corresponds to the PTE having the sequence (SEQ ID NO: 5) having the Uniprot number P0A434. This sequence is referred to herein as m0p95.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 26 is L and not replaceable, the amino acid at position 31 is M and not replaceable, the amino acid at position 73 is D and not replaceable, the amino acid at position 88 is E and not replaceable, the amino acid at position 94 is A and not replaceable, the amino acid at position 95 is E and not replaceable, the amino acid at position 159 is R and not replaceable, the amino acid at position 170 is E and not replaceable, the amino acid at position 180 is D and not replaceable, the amino acid at position 188 is E and not replaceable, the amino acid at position 191 is D and not replaceable, the amino acid at position 199 is D and not replaceable, the amino acid at position 208 is A and not replaceable, the amino acid at position 215 is D and not replaceable, the amino acid at position 219 is E and not replaceable, the amino acid at position 246 is A and not replaceable, the amino acid at position 270 is A and not replaceable, the amino acid at position 271 is D and not replaceable, the amino acid at position 304 is H and not replaceable, the amino acid at position 307 is E and not replaceable, the amino acid at position 320 is D and not replaceable, the amino acid at position 324 is D and not replaceable, the amino acid at position 325 is T and not replaceable, the amino acid at position 327 is M and not replaceable, and the amino acid at position 329 is E and not replaceable, where the coordinates corresponds to the PTE having the sequence (SEQ ID NO: 5) having the Uniprot number P0A434. This sequence is referred to herein as m0p45.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 95 is E and not replaceable, the amino acid at position 180 is D and not replaceable, the amino acid at position 199 is D and not replaceable, the amino acid at position 215 is D and not replaceable, the amino acid at position 270 is V and not replaceable, the amino acid at position 325 is T and not replaceable, the amino acid at position 329 is E and not replaceable, the amino acid at position 267 is R and not replaceable, the amino acid at position 270 is S and not replaceable, and the amino acid at position 271 is W and not replaceable where the coordinates corresponds to the PTE having the sequence (SEQ ID NO: 5) having the Uniprot number P0A434. This sequence is referred to herein as 3B11.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 95 is E and not replaceable, the amino acid at position 180 is D and not replaceable, the amino acid at position 199 is D and not replaceable, the amino acid at position 215 is D and not replaceable, the amino acid at position 270 is V and not replaceable, the amino acid at position 325 is T and not replaceable, the amino acid at position 329 is E and not replaceable, the amino acid at position 267 is R and not replaceable, the amino acid at position 270 is D and not replaceable, and the amino acid at position 271 is W and not replaceable where the coordinates corresponds to the PTE having the sequence (SEQ ID NO: 5) having the Uniprot number P0A434. This sequence is referred to herein as 6C12.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 6 as determined using the Standard protein-protein BLAST [blastp] software of the NCBI, wherein the amino acid at position 132 is E and not replaceable, the amino acid at position 173 is N and not replaceable, the amino acid at position 254 is G and not replaceable, the amino acid at position 309 is W and not replaceable, the amino acid at position 95 is E and not replaceable, the amino acid at position 180 is D and not replaceable, the amino acid at position 199 is D and not replaceable, the amino acid at position 215 is D and not replaceable, the amino acid at position 270 is V and not replaceable, the amino acid at position 325 is T and not replaceable, the amino acid at position 329 is E and not replaceable, the amino acid at position 267 is M and not replaceable, the amino acid at position 270 is S and not replaceable, and the amino acid at position 271 is W and not replaceable where the coordinates corresponds to the PTE having the sequence (SEQ ID NO: 5) having the Uniprot number P0A434. This sequence is referred to herein as 4E11.

According to another embodiment, the polypeptide comprises a sequence at least 99% or 100% homologous to any of the sequences as set forth in SEQ ID NO: 2, 3, 11, 13, 15, 17, 19, 25, 27, 29, 31, 33 or 35.

It will be appreciated that in order to aid in isolation of the protein, the protein may be expressed with additional amino acid sequences (i.e., tags) engineered to enhance stability, production, purification, yield or toxicity of the expressed polypeptide. Such a fusion protein can be designed so that the fusion protein can be readily isolated by affinity chromatography; e.g., by immobilization on a column specific for the heterologous protein.

Examples of affinity tags include, but are not limited to HIS, CBP, CYD (covalent yet dissociable NorpD peptide), Strep II, FLAG, HPC (heavy chain of protein C) peptide tags, and the GST and MBP protein fusion tag systems.

According to a particular embodiment, the affinity tag is maltose binding protein (MBP).

According to a particular embodiment, the affinity tag is MBP and the sequence is adapted for expression in *E. Coli* (e.g. devoid of the first 29 amino acids of SEQ ID NO: 5).

Thus, the polypeptide may comprise a sequence at least 90%, 91%, 92%, 93%, 94%, 95%, 96%, 97%, 98%, 99% or 100% homologous to SEQ ID NO: 3, wherein the amino acid at position 132 is E and not replaceable, the amino acid at position 173 is N and not replaceable, the amino acid at position 254 is G and not replaceable and the amino acid at position 203 is L and not replaceable where the coordinates corresponds to the PTE having the sequence (SEQ ID NO: 5) having the Uniprot number P0A434.

Thus, the polypeptide may comprise a sequence at least 90%, 91%, 92%, 93%, 94%, 95%, 96%, 97%, 98%, 99% or 100% homologous to SEQ ID NO: 3, wherein the amino acid at position 77 is A and not replaceable, wherein the amino acid at position 80 is V and not replaceable, wherein the amino acid at position 132 is E and not replaceable, the amino acid at position 173 is N and not replaceable, the amino acid at position 254 is G and not replaceable and the amino acid at position 203 is L and not replaceable, wherein the amino acid at position 208 is D and not replaceable, wherein the amino acid at position 274 is N and not replaceable, where the coordinates corresponds to the PTE having the sequence (SEQ ID NO: 5) having the Uniprot number P0A434.

Thus, the polypeptide may comprise a sequence at least 90%, 91%, 92%, 93%, 94%, 95%, 96%, 97%, 98%, 99% or 100% homologous to SEQ ID NO: 3, wherein the amino acid at position 77 is A and not replaceable, wherein the amino acid at position 80 is V and not replaceable, wherein the amino acid at position 132 is E and not replaceable, the amino acid at position 173 is N and not replaceable, the amino acid at position 254 is G and not replaceable and the amino acid at position 203 is L and not replaceable, wherein the amino acid at position 208 is D and not replaceable, wherein the amino acid at position 274 is N and not replaceable, wherein the amino acid at position 342 is S and not replaceable, where the coordinates corresponds to the PTE having the sequence (SEQ ID NO: 5) having the Uniprot number P0A434.

According to another aspect of the present invention there is provided a genetically modified polypeptide comprising an amino acid sequence of phosphotriesterase (PTE) having catalytic efficiency $k_{cat}/K_M$ greater than $3.10^6 M^{-1} min^{-1}$ for the Sp isomer of RVX, retaining at least 50% of its catalytic activity at 50° C. as its catalytic activity at 25° C. when in a lysate.

Preferably, the activity of the polypeptide of this aspect of the present invention (in the presence of 50 μM of the metal chelator 1,10 phenantroline) is at least 50% of its catalytic activity in the absence of the metal chelator.

According to one embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 as determined using the Standard protein-protein BLAST [blastp] software of the NCBI, wherein the amino acid at position 106 is A and not replaceable, the amino acid at position 132 is E and not replaceable, the amino acid at position 173 is N and not replaceable, the amino acid at position 203 is F and not replaceable, the amino acid at position 254 is G and not replaceable where the coordinates corresponds to the PTE having the sequence (SEQ ID NO: 5) having the Uniprot number P0A434.

According to one embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 21 as determined using the Standard protein-protein BLAST [blastp] software of the NCBI, wherein the amino acid at position 106 is A and not replaceable, the amino acid at position 132 is E and not replaceable, the amino acid at position 173 is N and not replaceable, the amino acid at position 203 is A and not replaceable, the amino acid at position 254 is G and not replaceable where the coordinates corresponds to the PTE having the sequence (SEQ ID NO: 5) having the Uniprot number P0A434.

According to one embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 or 23 as determined using the Standard protein-protein BLAST [blastp] software of the NCBI, wherein the amino acid at position 106 is A and not replaceable, the amino acid at position 132 is E and not replaceable, the amino acid at position 173 is N and not replaceable, the amino acid at position 203 is L and not replaceable, the amino acid at position 254 is G and not replaceable where the coordinates corresponds to the PTE having the sequence (SEQ ID NO: 5) having the Uniprot number P0A434.

According to one embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 5 as determined using the Standard protein-protein BLAST [blastp] software of the NCBI, wherein the amino acid at position 106 is A and not replaceable, the amino acid at position 132 is E and not replaceable, the amino acid at position 173 is N and not replaceable, the amino acid at position 203 is F and not replaceable, the amino acid at position 254 is G and not replaceable where the coordinates corresponds to the PTE having the sequence (SEQ ID NO: 5) having the Uniprot number P0A434.

According to this aspect of the present invention, the amino acid sequence of the PTE comprises asparagine at position 173, where the coordinates corresponds to the PTE having the sequence (SEQ ID NO: 5) having the Uniprot number P0A434. According to this aspect of the present invention the amino acid at position 203 of the polypeptide is alanine, where the coordinates corresponds to the PTE having the sequence (SEQ ID NO: 5) having the Uniprot number P0A434.

According to this aspect of the present invention the amino acid at position 203 of the polypeptide is phenylalanine, where the coordinates corresponds to the PTE having the sequence (SEQ ID NO: 5) having the Uniprot number P0A434.

According to this aspect of the present invention the amino acid at position 203 of the polypeptide is leucine, where the coordinates corresponds to the PTE having the sequence (SEQ ID NO: 3 or 5) having the Uniprot number P0A434.

According to this aspect of the present invention the amino acid sequence of PTE comprises the mutation T173N, I106A, F132E, A203F and H254G, where the coordinates corresponds to the PTE having the sequence (SEQ ID NO: 5) having the Uniprot number P0A434.

According to this aspect of the present invention the amino acid sequence of PTE comprises the mutation T173N, I106A, F132E and H254G, where the coordinates corresponds to the PTE having the sequence (SEQ ID NO: 5) having the Uniprot number P0A434.

According to this aspect of the present invention the amino acid sequence of PTE comprises the mutation T173N, I106A, F132E, A203L and H254G, where the coordinates corresponds to the PTE having the sequence (SEQ ID NO: 5) having the Uniprot number P0A434.

According to this aspect of the present invention the amino acid sequence of PTE comprises the mutation T173Q, I106A, F132E and H254G, and the amino acid at position 203 is A, where the coordinates corresponds to the PTE having the sequence (SEQ ID NO: 5) having the Uniprot number P0A434.

Additional contemplated mutations in combinations with any of the contemplated mutations include K77A, A80V, G208D and I274N.

According to one embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 3 as determined using the Standard protein-protein BLAST [blastp] software of the NCBI, wherein the amino acid at position 106 is A and not replaceable, the amino acid at position 132 is E and not replaceable, the amino acid at position 173 is N and not replaceable, the amino acid at position 203 is A and not replaceable, the amino acid at position 254 is G and not replaceable where the coordinates corresponds to the PTE having the sequence (SEQ ID NO: 5) having the Uniprot number P0A434.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 3 as determined using the Standard protein-protein BLAST [blastp] software of the NCBI, wherein the amino acid at position 77 is A and not replaceable, wherein the amino acid at position 80 is V and not replaceable, wherein the amino acid at position 106 is A and not replaceable wherein the amino acid at position 132 is E and not replaceable, the amino acid at position 173 is N and not replaceable, the amino acid at position 203 is A or F and not replaceable, the amino acid at position 254 is G and not replaceable, wherein the amino acid at position 208 is D and not replaceable, wherein the amino acid at position 274 is N and not replaceable, where the coordinates corresponds to the PTE having the sequence (SEQ ID NO: 5) having the Uniprot number P0A434.

The polypeptides of this aspect of the present invention are preferably expressible in bacteria such as *E. coli* [e.g., BL21, BL21 (DE3), Origami B (DE3), available from Novagen (www(dot)calbiochem(dot)com) and RIL (DE3) available from Stratagene, (www(dot)stratagene(dot)com). Essentially, at least 2%, at least 5%, at least 10%, at least 20%, at least 30%, at least 40%, at least 50%, at least 60%, at least 70%, at least 80%, at least 90%, at least 95% or more, say 100%, of bacterially expressed protein remains soluble (i.e., does not precipitate into inclusion bodies).

As mentioned previously, the present inventors have found that removal of the first 29 amino acids of the PTE aided in the successful expression in bacteria.

Thus, according to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 4 as determined using the Standard protein-protein BLAST [blastp] software of the NCBI, wherein the amino acid at position 106 is A and not replaceable, the amino acid at position 132 is E and not replaceable, the amino acid at position 173 is N and not replaceable, the amino acid at position 203 is F and not replaceable, the amino acid at position 254 is G and not replaceable where the coordinates corresponds to the PTE having the sequence (SEQ ID NO: 5) having the Uniprot number P0A434. Since the first 29 amino acids of SEQ ID NO: 4 have been removed in the polypeptide of SEQ ID NO: 6, the first amino acid of SEQ ID NO: 4 is numbered 30, the second amino acid of SEQ ID NO: 4 is numbered 31 etc with respect to the numbering of the positions of the mutations.

According to another embodiment, the polypeptide comprises a sequence as least 90% homologous, at least 91% homologous, at least 92% homologous, at least 93% homologous, at least 94% homologous, at least 95% homologous, at least 96% homologous, at least 97% homologous, at least 98% homologous, at least 99% homologous to the sequence as set forth in SEQ ID NO: 4 as determined using the Standard protein-protein BLAST [blastp] software of the NCBI, wherein the amino acid at position 77 is A and not replaceable, wherein the amino acid at position 80 is V and not replaceable, wherein the amino acid at position 106 is A and not replaceable wherein the amino acid at position 132 is E and not replaceable, the amino acid at position 173 is N and not replaceable, the amino acid at position 203 is A or F and not replaceable, the amino acid at position 254 is G and not replaceable, wherein the amino acid at position 208 is D and not replaceable, wherein the amino acid at position 274 is N and not replaceable, where the coordinates corresponds to the PTE having the sequence (SEQ ID NO: 5) having the Uniprot number P0A434.

According to another embodiment, the polypeptide comprises a sequence at least 99% or 100% homologous to SEQ ID NO: 4, 21 or 23.

It will be appreciated that in order to aid in isolation of the protein, the protein may be expressed with additional amino acid sequences (i.e., tags) engineered to enhance stability, production, purification, yield or toxicity of the expressed polypeptide. Such a fusion protein can be designed so that the fusion protein can be readily isolated by affinity chromatography; e.g., by immobilization on a column specific for the heterologous protein.

According to a particular embodiment, the affinity tag for the polypeptide of this aspect of the present invention is MBP.

According to a particular embodiment, the affinity tag is MBP and the sequence is adapted for expression in *E. Coli* (for example devoid of the first 29 amino acids of SEQ ID NO: 5).

Thus, the polypeptide may comprise a sequence at least 90%, 91%, 92%, 93%, 94%, 95%, 96%, 97%, 98%, 99% or 100% homologous to SEQ ID NO: 8, wherein the amino acid at position 106 is A and not replaceable wherein the amino acid at position 132 is E and not replaceable, the amino acid at position 173 is N and not replaceable, the amino acid at position 254 is G and not replaceable and the amino acid at position 203 is A or F and not replaceable where the coordinates corresponds to the PTE having the sequence (SEQ ID NO: 5) having the Uniprot number P0A434.

Thus, the polypeptide may comprise a sequence at least 90%, 91%, 92%, 93%, 94%, 95%, 96%, 97%, 98%, 99% or 100% homologous to SEQ ID NO: 8, wherein the amino acid at position 77 is A and not replaceable, wherein the amino acid at position 80 is V and not replaceable, wherein the amino acid at position 106 is I and not replaceable, wherein the amino acid at position 132 is E and not replaceable, the amino acid at position 173 is N and not replaceable, the amino acid at position 254 is G and not replaceable and the amino acid at position 203 is A or F and not replaceable, wherein the amino acid at position 208 is D and not replaceable, wherein the amino acid at position 274 is N and not replaceable, where the coordinates corresponds to the PTE having the sequence (SEQ ID NO: 5) having the Uniprot number P0A434.

In particular embodiments, the polypeptide of embodiments of the present invention is at least 99% homologous to any of the sequences as set forth in SEQ ID NO: 2, 3, 4, 8, 11, 13, 15, 17, 19, 21, 23, 25, 27, 29, 31, 33, or 35.

In other embodiments, the polypeptide of embodiments of the present invention comprises the sequence as set forth in SEQ ID NO: 2, 3, 4, 8, 11, 13, 15, 17, 19, 21, 23, 25, 27, 29, 31, 33, or 35.

The term "polypeptide" as used herein encompasses native polypeptides (synthetically synthesized polypeptides or recombinant polypeptides) and peptidomimetics, as well as peptoids and semipeptoids which are peptide analogs, which may have, for example, modifications rendering the polypeptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

Synthetic amino acid substitutions may be employed to improve stability and bioavailability.

Table 1A below lists non-conventional or modified amino acids e.g., synthetic, which can be used with the present invention.

TABLE 1A

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |

TABLE 1A-continued

| Non-conventional amino acid | Code | Non-conventional amino acid | Code |
|---|---|---|---|
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) | | N-(N-(3,3-diphenylpropyl) | |
| carbamylmethyl-glycine | Nnbhm | carbamylmethyl(1)glycine | Nnbhe |
| 1-carboxy-1-(2,2-diphenyl ethylamino)cyclopropane | Nmbc | | |

For any of the polypeptides described herein above, the present inventors contemplate all, 1-10, 1-5 or at least one, two, three, four, five, six, seven, eight, nine or ten or more of the additional modifications which will aid in their stabilization.

The additional modifications are summarized in Table 1B. It should be noted that the numbering of the modifications correspond to the numbering of the amino acids according to pdb code 1hzy, as set forth in SEQ ID NO: 5.

TABLE 1B

| Position (numbering according to pdb code 1hzy/SEQ ID NO: 5) | WT aa | Modification |
|---|---|---|
| 38 | N | M |
| 49 | A | L |
| 54 | T | M |
| 73 | F | W |
| 77 | K | D |
| 80 | A | I |
| 82 | K | R |
| 96 | R | D |
| 99 | V | I |
| 111 | S | E/Q |
| 113 | L | I |
| 116 | V | I |
| 117 | S | A |
| 118 | R | E |
| 147 | T | I/V |
| 166 | G | A |
| 180 | Q | E |
| 182 | L | K/R |
| 184 | L | F |
| 185 | K | R |
| 193 | A | E |
| 198 | V | I |
| 203 | A | C/D/E/H/N |
| 211 | Q | E |
| 214 | A | D/E/K/Q/R |

TABLE 1B-continued

| Position (numbering according to pdb code 1hzy/SEQ ID NO: 5) | WT aa | Modification |
|---|---|---|
| 222 | S | D/N/P |
| 231 | S | A |
| 238 | S | D/E |
| 242 | A | E |
| 269 | S | A |
| 274 | I | L/T |
| 293 | M | A/E/I/T/V |
| 294 | K | D/E |
| 327 | F | H |
| 330 | L | E |
| 343 | Q | D/E |
| 347 | A | D/E/T/R |
| 348 | G | A/M/N/Q/T |
| 350 | T | M |
| 352 | T | D/E |

The present teachings also provide for nucleic acid sequences encoding such PTE polypeptides.

Thus, according to an aspect of the present invention there is provided an isolated polynucleotide including a nucleic acid sequence, which encodes the isolated polypeptide of the present invention.

As used herein the phrase "an isolated polynucleotide" refers to a single or a double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase.

Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Polypeptides of the present invention can be synthesized using recombinant DNA technology or solid phase technology.

Recombinant techniques are preferably used to generate the polypeptides of the present invention. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce a polypeptide of the present invention using recombinant technology, a polynucleotide encoding a polypeptide of the present invention is ligated into a nucleic acid expression construct, which includes the polynucleotide sequence under the transcriptional control of a cis-regulatory (e.g., promoter) sequence suitable for directing constitutive or inducible transcription in the host cells, as further described hereinbelow.

Exemplary polynucleotide sequences for expressing the polypeptides of the present invention are set forth in SEQ ID NOs: 9 and 10.

Other than containing the necessary elements for the transcription and translation of the inserted coding sequence, the expression construct of the present invention can also include sequences (i.e., tags) engineered to enhance stability, production, purification, yield or toxicity of the expressed polypeptide. Such a fusion protein can be designed so that the fusion protein can be readily isolated by affinity chromatography; e.g., by immobilization on a column specific for the heterologous protein. Where a cleavage site is engineered between the peptide moiety and the heterologous protein, the peptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

A variety of prokaryotic or eukaryotic cells can be used as host-expression systems to express the polypeptide coding sequence. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence. Mammalian expression systems can also be used to express the polypeptides of the present invention. Bacterial systems are preferably used to produce recombinant polypeptides, according to the present invention, thereby enabling a high production volume at low cost.

Other expression systems such as insects and mammalian host cell systems, which are well known in the art can also be used by the present invention.

In any case, transformed cells are cultured under effective conditions, which allow for the expression of high amounts of recombinant polypeptides. Effective culture conditions include, but are not limited to, effective media, bioreactor, temperature, pH and oxygen conditions that permit protein production. An effective medium refers to any medium in which a cell is cultured to produce the recombinant polypeptides of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

Following a certain time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Polypeptides of the present invention can be used for treating an organophosphate exposure associated damage.

Thus according to an aspect of the invention there is provided a method of treating or preventing organophosphate exposure associated damage in a subject in need thereof, the method comprising providing the subject with a therapeutically effective amount of the isolated polypeptide described above to thereby treat the organophosphate exposure associated damage in the subject.

As used herein the term "treating" refers to preventing, curing, reversing, attenuating, alleviating, minimizing, suppressing or halting the deleterious effects of the immediate life-threatening effects of organophosphate intoxication and its long-term debilitating consequences.

As used herein the phrase "organophosphate exposure associated damage" refers to short term (e.g., minutes to several hours post-exposure) and long term damage (e.g., one week up to several years post-exposure) to physiological function (e.g., motor and cognitive functions). Organophosphate exposure associated damage may be manifested by the following clinical symptoms including, but not limited to, headache, diffuse muscle cramping, weakness, excessive secretions, nausea, vomiting and diarrhea. The condition may progress to seizure, coma, paralysis, respiratory failure, delayed neuropathy, muscle weakness, tremor, convulsions, permanent brain dismorphology, social/behavioral deficits and general cholinergic crisis (which may be manifested for instance by exacerbated inflammation and low blood count. Extreme cases may lead to death of the poisoned subjects.

As used herein the term "organophosphate compound" refers to a V-type organophosphate, as described herein above.

As used herein the phrase "a subject in need thereof" refers to a human or animal subject who is sensitive to OP toxic effects. Thus, the subject may be exposed or at a risk of exposure to OP. Examples include civilians contaminated by a terrorist attack at a public event, accidental spills in industry and during transportation, field workers subjected to pesticide/insecticide OP poisoning, truckers who transport pesticides, pesticide manufacturers, dog groomers who are overexposed to flea dip, pest control workers and various domestic and custodial workers who use these compounds, military personnel exposed to nerve gases.

As mentioned, in some embodiments of the invention the method is effected by providing the subject with a therapeutically effective amount of the PTE polypeptide of the invention.

As OP can be rapidly absorbed from lungs, skin, gastrointestinal (GI) tract and mucous membranes, PTE may be provided by various administration routes or direct application on the skin.

For example, the PTE may be immobilized on a solid support e.g., a porous support which may be a flexible sponge-like substance or like material, wherein the PTE is secured by immobilization. The support may be formed into various shapes, sizes and densities, depending on need and the shape of the mold. For example, the porous support may be formed into a typical household sponge, wipe or tissue paper.

For example, such articles may be used to clean and decontaminate wounds, while the immobilized PTE will not leach into a wound. Therefore, the sponges can be used to decontaminate civilians contaminated by a terrorist attack at a public event.

Alternatively or additionally, PTE may be administered to the subject per se or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the PTE accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, dermal, transmucosal, especially transnasal, intestinal or parenteral delivery, including intramuscular, subcutaneous and intramedullary injections as well as intrathecal, direct intraventricular, intravenous, intraperitoneal, intranasal, intrabone or intraocular injections.

Alternately, one may administer the pharmaceutical composition in a local rather than systemic manner, for example, via injection of the pharmaceutical composition directly into a tissue region (e.g., skin) of a patient. Topical administration is also contemplated according to the present teachings.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (nucleic acid construct) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer (see the Examples section which follows). Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

PTE may be administered prior to the OP exposure (prophylactically, e.g., 10 or 8 hours before exposure), and alternatively or additionally administered post exposure, even days after (e.g., 7 days) in a single or multiple-doses.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The ability of PTE to sequester OP molecules, suggests use of same in the decontamination of OP contaminated surfaces and detoxification of airborne OP.

Thus, an aspect of the invention further provides for a method of detoxifying a surface contaminated with an OP molecule; or preventing contamination of the surface with OP. The method is effected by contacting the surface with PDE.

Thus, synthetic and biological surfaces contemplated according to embodiments of the invention include, but are not limited to, equipment, laboratory hardware, devices, fabrics (clothes), skin (as described above) and delicate membranes (e.g., biological). The mode of application will very much depend on the target surface. Thus, for example, the surface may be coated with foam especially when the surface comprises cracks, crevices, porous or uneven surfaces. Application of small quantities may be done with a spray-bottle equipped with an appropriate nozzle. If a large area is contaminated, an apparatus that dispenses a large quantity of foam may be utilized.

Coatings, linings, paints, adhesives sealants, waxes, sponges, wipes, fabrics which may comprise the PTE may be applied to the surface (e.g., in case of a skin surface for topical administration). Exemplary embodiments for such are provided in U.S. Pat. Application No. 20040109853.

Surface decontamination may be further assisted by contacting the surface with a caustic agent; a decontaminating foam, a combination of baking condition heat and carbon dioxide, or a combination thereof. Sensitive surfaces and equipments may require non corrosive decontaminants such as neutral aqueous solutions with active ingredient (e.g., paraoxonases).

In addition to the above described coating compositions, OP contamination may be prevented or detoxified using an article of manufacture which comprise the PTE immobilized to a solid support in the form of a sponge (as described above), a wipe, a fabric and a filter (for the decontamination of airborne particles). Chemistries for immobilization are provided in U.S. Pat. Application 20040005681, which is hereby incorporated in its entirety.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are

Example 1

Materials and Methods

Generation of Mutants:

The mutants were generated by site directed mutagenesis of specific positions in variants C23 and A53 and screened for improved VX and RVX hydrolysis activity in cell lysates as described in Cherny et al.

Metal Stability Assay:

Purified enzymes (4 µM, in 50 mM Tris pH 8.0, 50 mM NaCl) were incubated for 90 min at ambient temperature with different concentrations of the metal chelator phenanthroline (0-1000 µM). All samples contained the same concentration of ethanol (0.3% during incubation with phenanthroline). The samples were subsequently diluted 1:1000 in 50 mM Tris buffer pH 8.0, incubated for 30 min at room temperature and assayed with paraoxon (0.25 mM). The residual paraoxonase activity was plotted as the fraction of activity of the untreated sample.

Enzyme Kinetics: Determining Hydrolysis Rates of Racemates (DTNB Assay).

Hydrolysis rates of OPs racemates were monitored by following the release of the thiol leaving group using the Ellman's reagent (DTNB). To a cuvette containing 1 ml of 50 mM Tris, 50 mM NaCl, 0.7 mM DTNB, pH 8.0, the specified enzyme concentration was added and the mixture was allowed to pre-incubate at 25° C. for 4 min. The enzymatic reaction was initiated by substrate (1-3 mM stock solution of the V-agents or the corresponding surrogates) addition to the reaction mixture (diluted 100-fold). The increase in Ellman's chromophore concentration as function of the reaction time was monitored continuously at 412 nm up to ≥95% of the expected maximal absorbance. The absorbance relating to 100% release of the substrates thiols was determined by repeating the above procedure in 0.5 M NaF in 50 mM phosphate buffer, pH 8.0, and with no enzyme. The kinetic parameters were determined by fitting the data directly to bi-exponential reaction (as described in Cherney et al, incorporated herein by reference) using GraphPad Prism version 5.00 for Windows.

Enzyme Kinetics: Determining Hydrolysis Rates of SP Isomer (AChE Assay).

Hydrolysis rates of the toxic, SP isomers of OPs were determined by measuring the rate of loss of AChE inhibition upon incubation of racemic OPs with individual PTE variants. Reactions were initiated by diluting in situ generated OP stock solutions (protocols for in situ preparation are known in the art) with the PTE variant in 1 ml of AB buffer (50 mM Tris pH 8.0, 50 mM NaCl) at 25° C. The final OP concentrations ranged between 0.1 to 0.5 µM. At various time points, aliquots were removed, and diluted 10-50-fold into 0.2 ml of 10 mM phosphate buffer pH 8.0 containing ~7 nM Torpedo californica acetylcholinesterase (TcAChE). The unhydrolyzed OPs in the removed reaction aliquots were allowed to inhibit the TcAChE for 60 min. The residual AChE activity was subsequently determined at 412 nm by 100-fold dilution in 50 mM phosphate buffer containing 0.7 mM DTNB and 1 mM acetylthiocholine (ATC) as substrate. Initial rates were inferred from the slope of the linear regression product versus time plots. The spontaneous hydrolysis rate of ATC was subtracted to give the net enzymatic rates. The residual %-activity of TcAChE at the various time points was determined relative to the initial rates measured in the absence of OP (100% activity) and with no PTE (0% activity). In the case of tabun, TcAChE was replaced by human AChE to shorten the inhibition reaction time (20 min). The %-activity values were plotted to derive the kcat/KM from the slope of the resulting single exponential curve, by fitting the data directly to a single exponential curve using GraphPad Prism version 5.00.

Results

Figure 2:
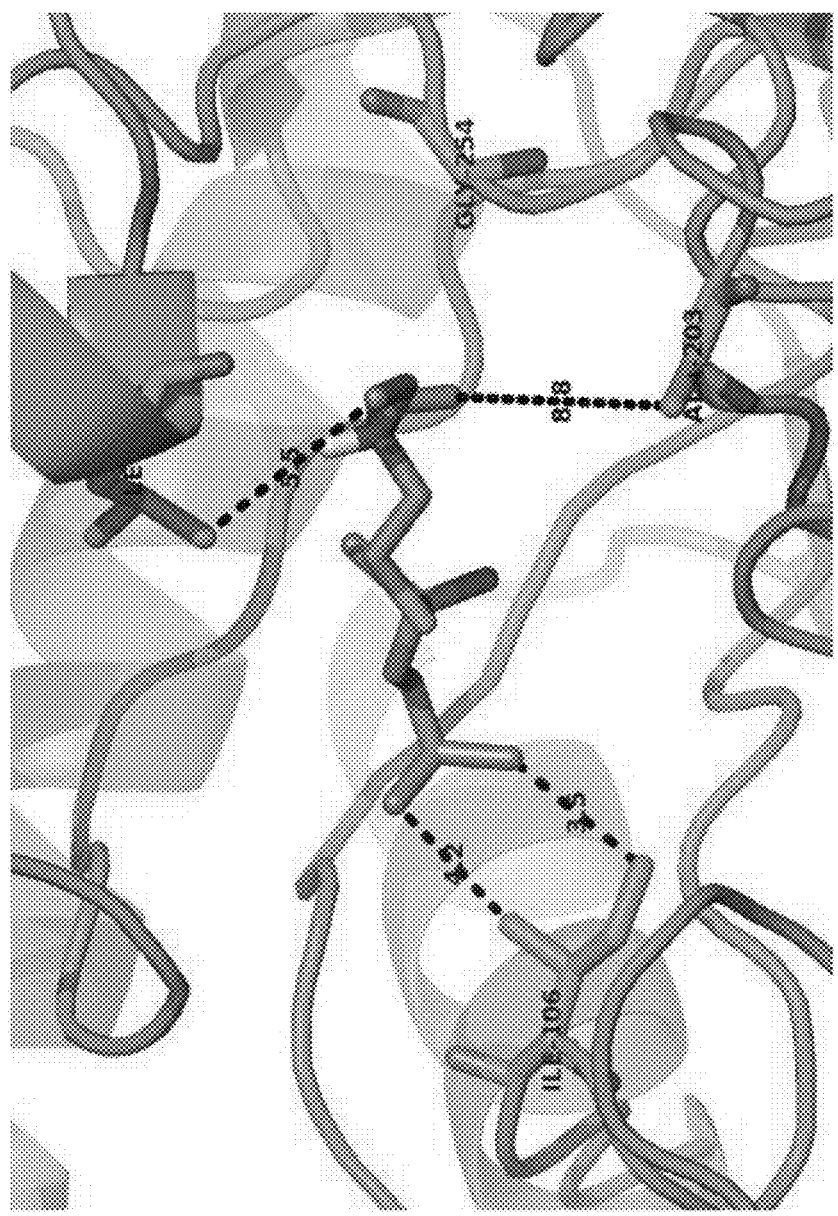

In order to increase the activity of PTE variant C23, the protein was crystallized and its structure resolved. Docking models of C23 with VX (FIG. 1) and RVX (FIG. 2) were then created and used to rationally design additional substitutions that would improve substrate binding and catalysis.

VX docked with C23 (FIG. 1) shows I106 in proximity to the O-ethyl moiety of VX (distances up to 4.9 Å) while the N,N-diisopropyl moiety is surrounded by A203 and L271 (distances up to 8Å). Similarly, RVX docked into C23 (FIG. 2) shows I106 in proximity with 0-isobutyl of RVX (distances up to 4.2 Å) while the N,N-diethyl moiety to be projected at a pocket bordered by residues A203, and L271 (distances up to 9Å). Since, C23 and A53 vary in sequence in only 4 amino acids (positions: 106, 173, 203, and 342) but have large differences in their activities towards VX and RVX (Cherny et al, 2013), the present inventors focused on mutating these 4 amino acids and among these, the amino acids that are in close proximity to the substrate, i.e., positions 106 and 203. These mutations were introduced into the C23 template.

The kinetic studies of the purified variants with the toxic enantiomer of VX revealed a 2.5-fold increase for A203L, over the lead variant of C23 (Table 1). Thus, the catalytic efficiency ($k_{cat}/K_M$) of variant C23-A203L is now ~1×10$^7$ M$^{-1}$ min$^{-1}$ making it a potential variant for treating VX intoxications.

TABLE 1

Activity of best C23 variants against VX and RVX
($k_{cat}/K_M \times 10^6$ M$^{-1}$min$^{-1}$)

| | DTNB protocol[a,b] | | | | Detoxification Protocol[c] | |
|---|---|---|---|---|---|---|
| Variant | (−) VX | (+) VX | (+) RVX (fast component) | (−) RVX (slow component) | (−) VX | (−) RVX |
| C23[d] | 3.70 ± 0.36 | 0.35 ± 0.008 | 2.89 ± 0.007 | 0.74 ± 0.44 | 2.74 ± 0.15 | 0.66 ± 0.02 |
| C23-A203L | 8.91 ± 0.41 | 0.68 ± 0.049 | 2.06 ± 0.049 | 0.51 ± 0.15 | 7.37 ± 0.69 | 0.30 ± 0.028 |
| C23-A203V | 5.21 ± 0.16 | 0.42 ± 0.007 | 1.58 ± 0.35 | 0.27 ± 0.08 | ND[f] | ND |
| C23-A203I | 5.40 ± 0.43 | 0.47 ± 0.027 | 1.72 ± 0.52 | 0.29 ± 0.053 | ND | ND |
| C23-I106L[e] | 5.72 ± 0.57 | 2.84 ± 0.27 | 8.75 ± 0.49 | ND (too slow) | ND | <0.06 |

TABLE 1-continued

Activity of best C23 variants against VX and RVX
($k_{cat}/K_M \times 10^6$ M$^{-1}$min$^{-1}$)

| | | | DTNB protocol[a,b] | | Detoxification Protocol[c] | |
|---|---|---|---|---|---|---|
| | | | (+) RVX (fast component) | (−) RVX (slow component) | | |
| Variant | (−) VX | (+) VX | | | (−) VX | (−) RVX |
| C23-I106L + A203L | 4.98 ± 0.36 | 1.98 ± 0.13 | 5.92 ± 0.46 | ND (too slow) | ND | <0.03 |

[a](−) and (+) VX are the individual pure enantiomers.
[b](−) and (+) RVX were assigned in accordance with the detoxification results.
[c]Detoxification protocol - catalytic activity determined from a protection assay of AChE (Ashani et al, 2011; Gupta et al, 2011).
[d](Cherny et al, 2013).
[e]The ILE106 mutations affected in opposite direction significantly the stereo-preference towards VX (decreased) and RVX (increased), supporting the modeling that suggests I106 to interact closely with the O-alkoxy moiety of the V agent.
[f]ND—not determined.

Improving the Thermal Stability and Metal Affinity of PTE-A53:

One of the most important properties required from an efficacious and safe drug is long-term stability. Protein drug stability needs to be maintained in order to ensure both long-term activity during storage and in-vivo use and also to prevent misfolding and aggregation that can compromise patient safety (e.g. by eliciting pathological processes such as amyloid deposition). The procedures of enhancing enzymatic activity by directed evolution or protein engineering require the introduction of amino-acid substitutions into the evolving protein that result in structural changes. These also effect protein folding and may act to reduce both its thermal and kinetic stabilities. The greater the number of mutations introduced into a protein, the greater the chances are that it will lose stability.

Figure 3:
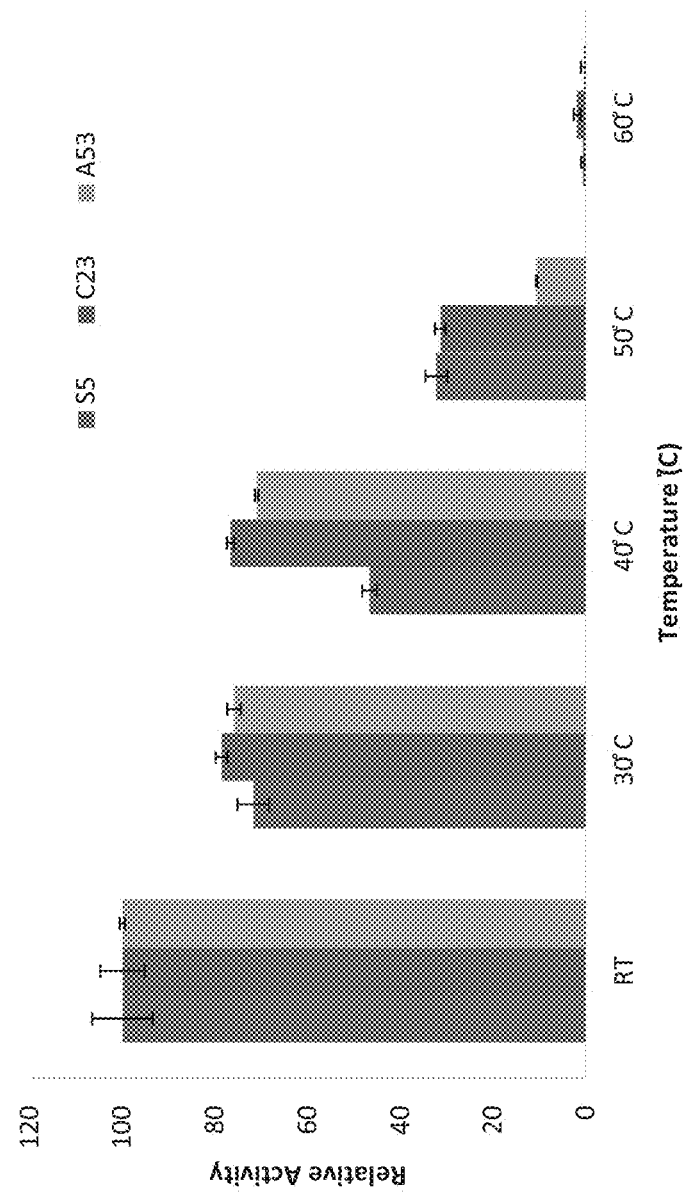
Figure 4:
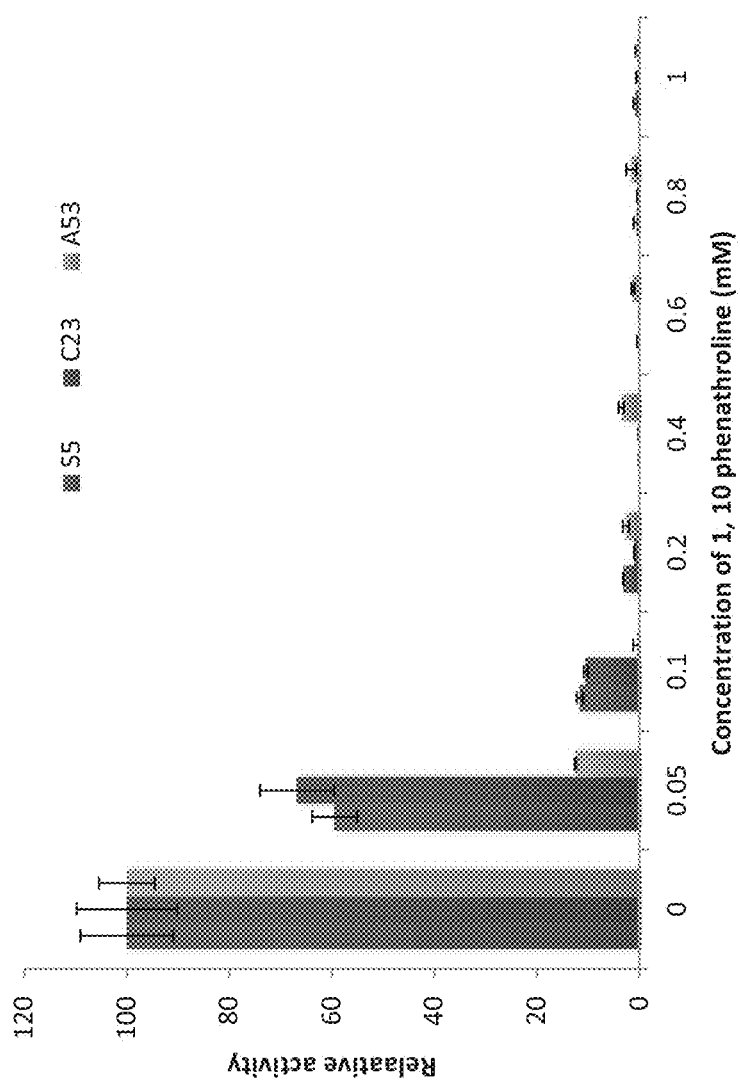

Indeed, the most active PTE variant evolved against the nerve agent RVX (i.e. A53) (Cherny et al, 2013) was later found to have both low thermal stability and metal binding affinity (FIGS. 3 and 4). As shown in FIG. 3, after 30 min at 50° C., A53 retains ~10% of its activity while the wild-type like PTE-S5 that served as the starting point for engineering, and C23, retain approximately 30% of their initial activities, suggesting that A53 is less thermostable. As for the metal binding affinity: at 50 µM concentration of 1,10-phenanthroline, A53 retains only 12% of its initial activity in contrast to PTE S5 and C23 which retain >50% activity, suggesting low metal ion affinity of A53 (FIG. 4).

Figure 5:
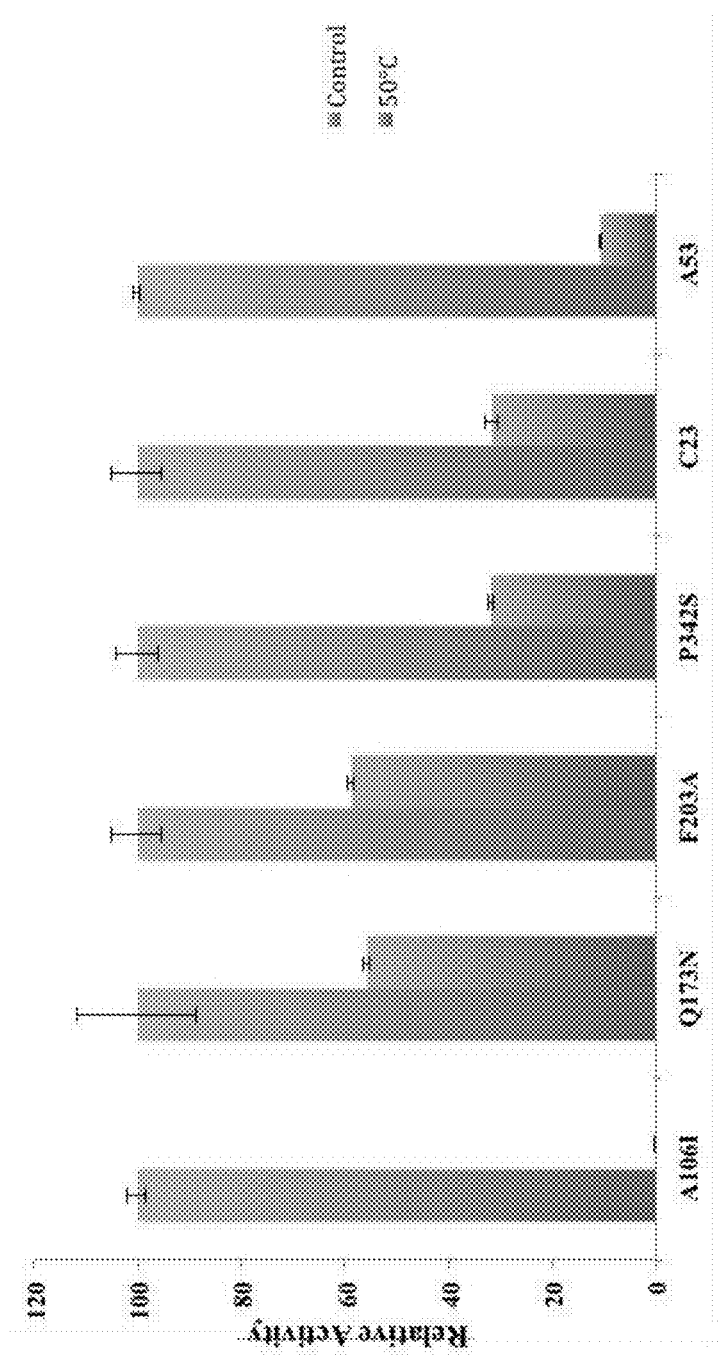
Figure 6:
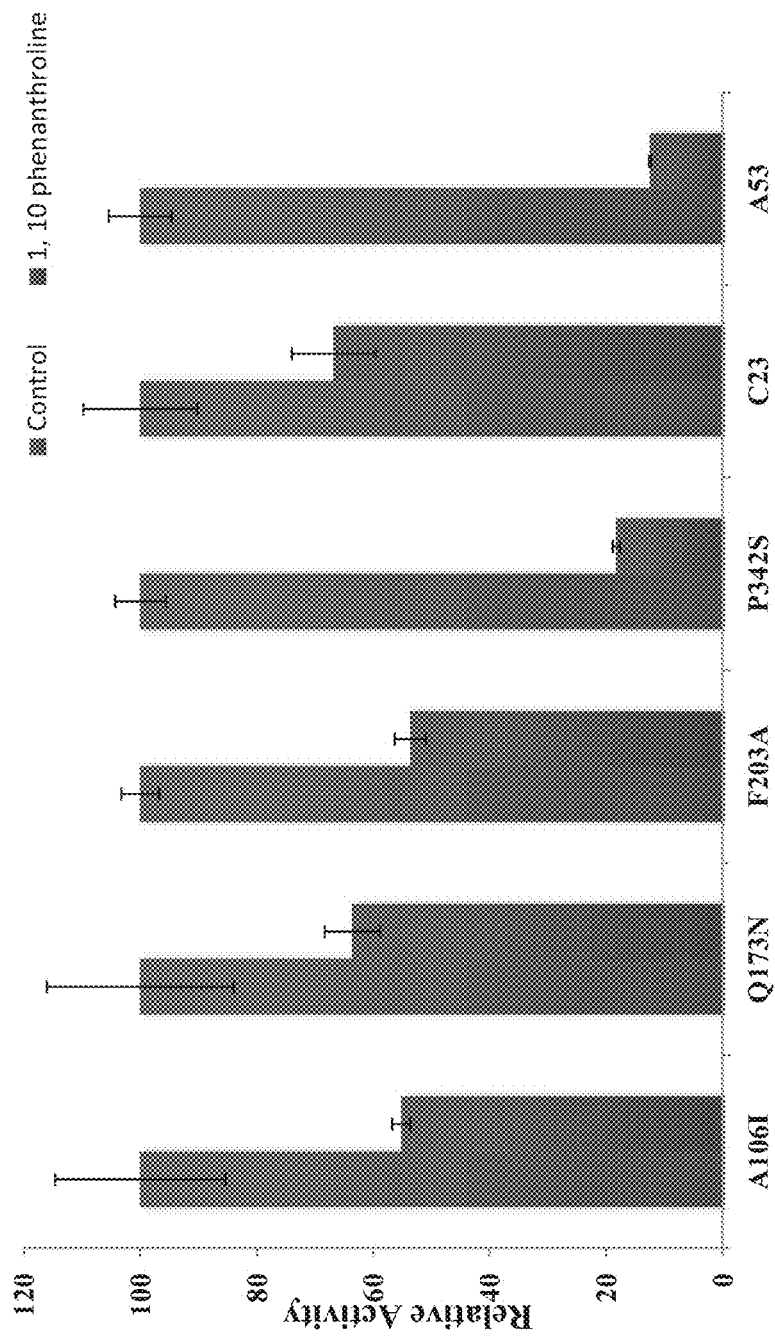

The lower thermal stability of A53 was manifested in low long-term stability of the purified enzyme during storage. Since variant A53 displayed high catalytic activity towards RVX, the present inventors decided to improve its thermal stability by systematically reverting the mutations in A53 to residues found at the same positions in variant C23 (a more stable variant). These would provide more stable A53 variants without hampering its catalytic efficiency with RVX. FIGS. 5 and 6 summarize the results of thermal stability and metal chelation studies with 4 such variants in lysates.

The data in FIG. 5 shows that the substitution A106I in A53 resulted in complete loss of thermal stability at 50° C., indicating the involvement of the amino acid at 106 position in the stability of the enzyme. In contrast, mutating residues in positions 173, 203 and 342 of A53 to the respective amino acids of the homologous PTE variant C23 had a stabilizing effect. These mutants exhibited improved thermal stability at 50° C. relative to A53 and both Q173N and F203A were even more stable than C23 at that temperature.

The metal affinity studies (FIG. 6) showed that C23 binds its active-site metal ions significantly tighter than A53 (e.g. its residual activity after chelator addition was ~5 fold greater than that of A53). However, all the introduced mutations except for P342S increased the metal binding affinity of A53 up to the level of C23. Thus, introducing the substitutions Q173N or F203A were able to increase both thermostability and metal binding affinity in A53, and to a lesser extent also P342S.

When the catalytic efficiency of the stabilized A53 variants A53-Q173N, A53-F203A and a combined mutant A53-Q173N+F203L were studied, it was found that they had retained 80-100% of the activity of A53 against RVX. Thus, the currently most active and stable PTE variant against RVX is A53-Q173N.

TABLE 2

Activity of best A53 variants against VX and RVX
($k_{cat}/K_M \times 10^6$ M$^{-1}$min$^{-1}$)

| | DTNB protocol[a,b] | | | | Detoxification Protocol[c] | |
|---|---|---|---|---|---|---|
| Variant | (−) VX | (+) VX | (+) RVX | (−) RVX | (−) VX | (−) RVX |
| A53[d] | 1.75 ± 0.008 | ND[e] | 0.68 ± 0.007 | 3.47 ± 0.007 | 3.00 ± 0.45 | 3.43 ± 0.54 |
| A53-Q173N | 1.64 ± 0.07 | ND | 1.05 ± 0.056 | 4.35 ± 0.35 | ND | 3.0 |
| A53-F203A | 2.20 ± 0.27 | ND | 0.66 ± 0.056 | 3.05 ± 0.13 | ND | 2.38 |
| A53-Q173N + F203L | 1.71 ± 0.04 | ND | 1.03 ± 0.04 | 4.0 ± 0.25 | ND | 2.66 |

[a]Comments; (−) and(+) VX are the individual pure enantiomers.
[b](−) and (+) RVX were assigned in accordance with the detoxification results.
[c]Detoxification protocol - catalytic activity determined from a protection assay of AChE (Ashani et al, 2011; Gupta et al, 2011).
[d](Cherny et al, 2013).
[e]ND—not determined.

Example 2

Additional PTE Variants Based on C23

Generation of Mutants and Screening Thereof:

The mutants were generated by site directed mutagenesis of specific positions in C23 variants and screened as described in Example 1.

Results

The rate of hydrolysis of VX by variants is summarized in Table 3A, herein below.

TABLE 3

| Mutant | $k_{cat}/K_M$ ($10^6$ M$^{-1}$min$^{-1}$) at 25° C. |
|---|---|
| C23 (the original variant) | 3.70 ± 0.36 |
| A203L | 8.91 ± 0.41 |
| A203I | 5.40 ± 0.43 |
| A203V | 5.21 ± 0.16 |
| I106L | 5.72 ± 0.57 |
| I106C | 3.20 ± 0.055 |
| L271F | 6.08 ± 0.32 |
| I106L/L271F | 4.12 ± 0.10 |
| H257W | 1.62 ± 0.042 |
| H257Y | 1.21 ± 0.021 |
| H257F | 2.92 ± 0.028 |
| S308T | 0.75 ± 0.005 |
| Y309W | 8.84 ± 0.67 |
| W131L | inactive |
| G60L | inactive |
| L303F | inactive |
| L271F/Y309W | 4.59 ± 0.79 |
| N173E | 2.44 ± 0.87 |
| A270E | 5.68 ± 0.90 |
| A203L/Y309W | 8.82 ± 1.26 |
| M317L | 3.89 ± 0.04 |
| M317K | 0.53 ± 0.04 |
| F306W | 0.24 ± 0.0032 |
| S308E | inactive |
| Y309R | inactive |
| W131Y | inactive |
| G60E | inactive |

The effect of the metal chelator (50 μM 1,10 phenanthroline) and temperature on relative activity of protein variants obtained by site-directed mutagenesis using C23 as a template is summarized in Table 3B herein below.

*$V_{max}$ obtained at R.T was taken as 100% and the $V_{max}$ at 50° C. was expressed relative to the values obtained at R.T. $^\$V_{max}$ obtained in absence of 1,10 phenanthroline was taken as 100% and the $V_{max}$ at 50 μM 1,10 phenanthroline was expressed relative to the values obtained in absence of 1,10 phenanthroline. Activity was determined using 1 mM paraoxon. The purified MBP-tagged proteins were used to determine thermal stability and metal chelation.

TABLE 3B

| Protein name | *Relative $V_{max}$ at 50° C. | $^\$$Relative $V_{max}$ at 50 μM 1,10 phenanthroline |
|---|---|---|
| C23 | 87.4 ± 0.6 | 91.4 ± 2.8 |
| A203L | 112.2 ± 14.9 | 98.1 ± 5.1 |
| A203I | 4.0 ± 0.1 | 4.9 ± 0.04 |
| A203V | 42.6 ± 1.5 | 109.7 ± 3.1 |
| A203L/L271F | 57.0 ± 4.2 | 68.8 ± 1.0 |
| I106L | 73.3 ± 3.0 | 119.9 ± 7.2 |
| L271F | 95.2 ± 3.4 | 101.1 ± 0.8 |
| I106L/L271F | 83.5 ± 2.0 | 86.1 ± 13.1 |
| H257W | 80.8 ± 3.3 | 105.9 ± 5.2 |
| H257Y | 79.9 ± 1.5 | 113.4 ± 5.5 |
| W131V | 93.8 ± 1.4 | 93.9 ± 8.2 |
| G60L | ND | 67.3 ± 1.6 |
| L303F | ND | 89.8 ± 1.9 |

The rate of hydrolysis of VX by mutants based on A203L based variants with mutations at 272, 270, and 271 are summarized in Table 4, herein below.

TABLE 4

| Name of Mutant | Amino acid mutations | $K_{cat}/K_m$ ($10^6$ M$^{-1}$min$^{-1}$) at 25° C. |
|---|---|---|
| A203L | | 8.6 ± 1.14 |
| Y309W | | 8.8 ± 0.7 |
| A203L/Y309W | | 8.8 ± 1.3 |

TABLE 7

| Mutant | $k_{cat}/K_M$ (10⁻⁶ M⁻¹min⁻¹) at 25° C. (−) RVX | $k_{cat}/K_M$ (10⁻⁶ M⁻¹min⁻¹) at 25° C. (+) RVX |
|---|---|---|
| A53 | 4.26 | 0.68 |
| Q173N | 4.90 | 0.80 |
| F203A | 5.57 | 1.23 |
| Q173N/F203A | 4.36 ± 0.01 | 1.29 ± 0.0028 |
| Q173N/F203L | 4.27 ± 0.38 | 1.01 ± 0.06 |

The effect of metal chelator (50 μM 1,10 phenanthroline) and temperature on relative activity of protein variants based of A53 is presented in Table 8 herein below. *$V_{max}$ obtained at R.T was taken as 100% and the $V_{max}$ at 50° C. was expressed relative to the values obtained at R.T. $^$V_{max}$ obtained in absence of 1,10 phenanthroline was taken as 100% and the $V_{max}$ at 50 μM 1,10 phenanthroline was expressed relative to the values obtained in absence of 1,10 phenanthroline. Activity was determined using 1 mM paraoxon. The purified MBP-tagged proteins were used to determine thermal stability and metal chelation.

TABLE 8

| Protein name | *Relative $V_{max}$ at 50° C. | $^$Relative $V_{max}$ at 50 μM 1,10 phenanthroline |
|---|---|---|
| A53 | 49.5 ± 3.9 | 67.9 ± 2.2 |
| Q173N | 36.5 ± 1.1 | 90.7 ± 3.3 |
| F203A | 58.1 ± 1.2 | ND |
| Q173N/F203A | 93.3 ± 14.7 | 102.2 ± 1.7 |
| Q173N/F203L | 66.3 ± 0.5 | 89.0 ± 1.3 |

Example 4

Design for Stabilization of Phosphotriesterase

The method presented herein was implemented on the C23-Y309W variant of PTE (SEQ ID NO: 11).

The BLAST analysis against a non-redundant protein database yielded a minimal sequence identity cutoff of 34% yielded a relatively small and redundant multiple sequence alignment (MS A). This was an expected result for a recently evolved enzyme that has only a few similar homologous proteins. Hence, to enrich the sequence data the identity cutoff was reduced to 28%, which significantly improved diversity yielding an MSA that was derived from qualifying 95 homologous sequences with varying diversities from one another.

Residues surrounding the catalytic active site pocket and the zinc atoms, as well as residues within the homodimer interface, were identified as key restudies (fixed).

The method was used to select 3 designed sequences (stabilized PTE variants) using the PTE variant C23-Y309W as an original protein. Three acceptance thresholds were used in the single-position scanning step, −0.45 r.e.u, −0.95 r.e.u and −2.0 r.e.u. Combinatorial design under these acceptance thresholds yielded designed sequences denoted C23_m0p45 (SEQ ID NO. 25), C23_m0p95 (SEQ ID NO. 27) and C23_m2p0 (SEQ ID NO. 29), each having 25, 16 and 7 amino acid substitutions, respectively.

The three designs of the PTE variant C23-Y309W, C23_m0p45, C23_m0p95 and C23_m2p0, were cloned, fused to an maltose-binding protein tag, expressed in GG48 E. coli cells to maintain a high internal zinc concentration, and purified as previously described [Cherny, I. et al., ACS Chem Biol, 2013, 8(10):2394-403]. Thermostabilization and metal binding affinity of these designs were compared to those of the original protein, and the results are presented in Table 9, presenting residual catalytic activity at different temperatures, and Table 10, presenting residual catalytic activity following metal chelation using 50 μM 1,10 phenanthroline.

Vmax is the maximal velocity of paraoxon hydrolysis examined at 405 nm using purified protein samples. Vmax obtained at room temperature was taken as "100%" and the Vmax at 50° C. was expressed relative to the values obtained at room temperature.

TABLE 9

| Protein | Relative Vmax at 50° C.* | Relative Vmax at 60° C.* |
|---|---|---|
| C23-Y309W (parent) | 90.75 ± 13.02 | 1.83 ± 0.12 |
| C23_m0p45 (variant) | 16.82 ± 0.50 | 0.71 |
| C23_m0p95 (variant) | 97.56 ± 9.85 | 27.36 ± 2.67 |
| C23_m2p0 (variant) | 97.02 ± 3.04 | 31.53 ± 5.64 |

TABLE 10

| Protein | Relative Vmax at 50 μM 1,10 phenanthroline |
|---|---|
| C23-Y309W (parent) | 84.71 ± 3.60 |
| C23_m0p45 (variant) | 2.04 ± 0.38 |
| C23_m0p95 (variant) | 78.94 ± 3.88 |
| C23_m2p0 (variant) | 98.95 ± 4.10 |

As can be seen in Tables 9 and 10, two designs, C23_m2p0 and C23_m0p95, displayed 15-fold higher residual catalytic activity at 60 C.° relative to C23-Y309W. Variant C23_m0p45 was found to be less stable than the original protein. In the presence of 50 μM 1,10 phenanthroline, a metal chelating compound that inactivates the enzyme PTE by removing its catalytic $Zn^{2+}$ ions, C23_m2p0 displayed higher residual activity than the C23-Y309W, while C23_m0p95 and C23_m0p45 displayed similar or less residual activity respectively.

Table 11 presents the catalytic efficiency (kcat/KM) of the C23-Y309W and other designed variants of PTE in hydrolysis of the chemical warfare agent VX.

TABLE 11

| Protein | kcat/KM × 10⁶ M⁻¹min⁻¹ Room Temp | kcat/KM × 10⁶ M⁻¹min⁻¹ 37° C. | Activity enhancement |
|---|---|---|---|
| C23-Y309W (parent) | 12.8 | 21.8 | 1.7 |
| C23_m0p45 (variant) | 7.15 | — | — |
| C23_m2p0 (variant) | 19.45 | 33.8 | 1.7 |
| C23_m0P95 (variant) | 19.3 | 30.9 | 1.6 |

As can be seen in Table 11, both C23_m2p0 and C23_m0p95 variants displayed higher activity than C23-Y309W, while the variant C23_m0p45 displayed reduced activity compared to C23-Y309W, at room temperature.

Table 12 summarizes the rate of hydrolysis of Vx by M2p0-based mutants.

TABLE 12

| Name of Mutant | Amino acid mutations | $K_{cat}/K_m$ (10⁶ M⁻¹min⁻¹) at 25° C. | $K_{cat}/K_m$ (10⁻⁶ M⁻¹min⁻¹) at 37° C. |
|---|---|---|---|
| 3B11/2A7 | S267R/A270S/L271W | 13.9 ± 2.0 | 21.2 ± 2.6 |
| 6C12 | S267R/A270D/L271W | 14.3 ± 1.5 | 26.0 ± 2.1 |

TABLE 12-continued

| Name of Mutant | Amino acid mutations | $K_{cat}/K_m$ $(10^6 M^{-1}min^{-1})$ at 25° C. | $K_{cat}/K_m$ $(10^6 M^{-1}min^{-1})$ at 37° C. |
|---|---|---|---|
| 4E11 | S267M/A270S/L271W | 30.6 ± 3.3 | 41.6 ± 6.6 |
| m2p0 (parent) | S267/A270/L271 | 19.45 ± 0.77 | 33.8 ± 4.3 |

Table 13 summarizes the effect of metal chelator (50 µM 1,10 phenanthroline) and temperature on relative activity of m2p0 based mutants.

TABLE 13

| Name of Mutant | Amino acid mutations | *Relative $V_{max}$ at 50° C. | $Relative $V_{max}$ at 50 µM 1, 10 phenanthroline |
|---|---|---|---|
| 3B11 | S267R/A270S/L271W | 75.38 ± 1.89 | 98.53 ± 2.42 |
| 6C12 | S267R/A270D/L271W | 77.01 ± 4.29 | 37.48 ± 1.27 |
| 4E11 | S267M/A270S/L271W | 78.02 ± 1.36 | 79.24 ± 11.03 |

*$V_{max}$ obtained at R.T was taken as 100% and the $V_{max}$ at 50° C. was expressed relative to the values obtained at R.T.
$$V_{max}$ obtained in absence of 1,10 phenanthroline was taken as 100% and the Vmax at 50 µM 1,10 phenanthroline was expressed relative to the values obtained in absence of 1,10 phenanthroline. Activity was determined using 1 mM paraoxon. The purified MBP-tagged proteins were used to determine thermal stability and metal chelation. Incubation was performed in 100 mM NaCl/50 mM Tris, pH 8.0 containing 1-10 µM ZnCl$_2$ after dilution of the stock.

Example 5

Experiments Performed on Cell Lysates Comprising Stabilized Variants

Figure 7:
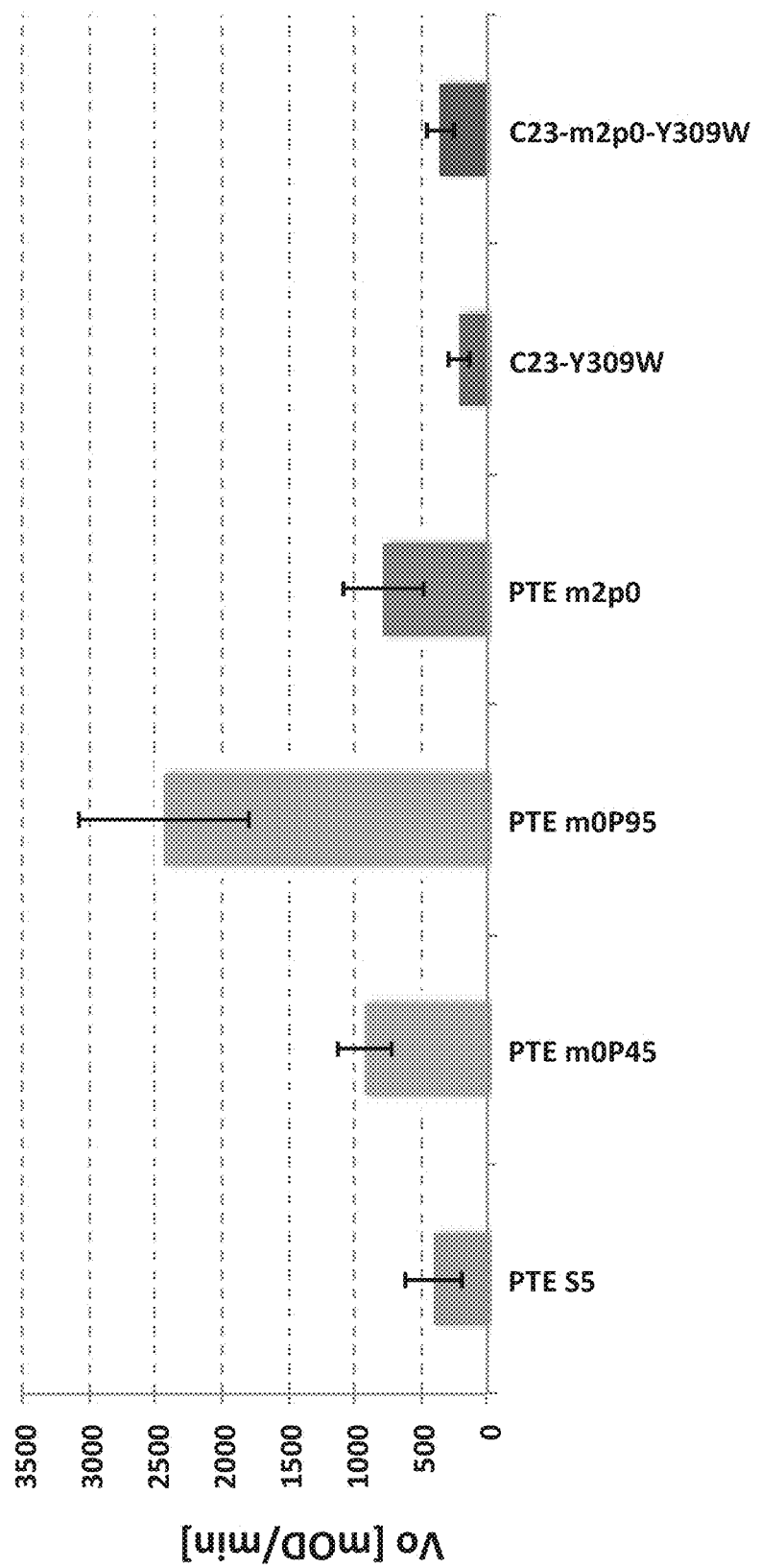
Figure 8:
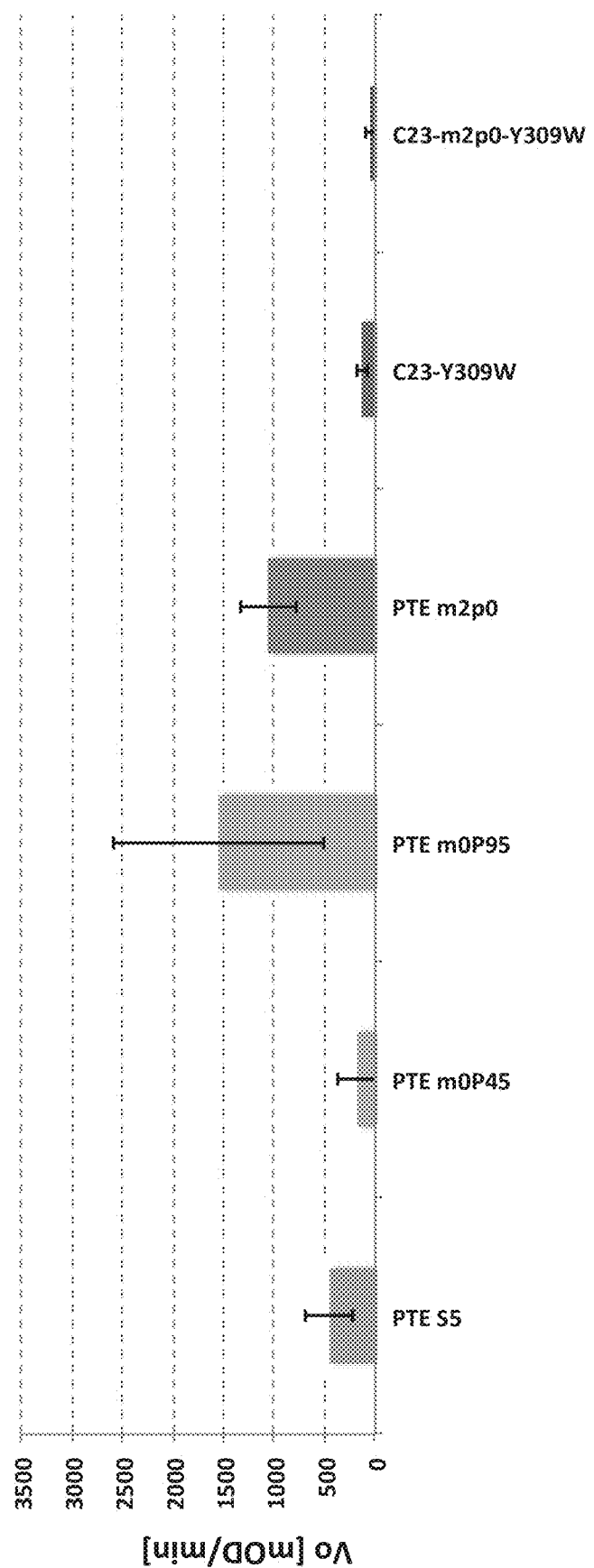
Figure 9:
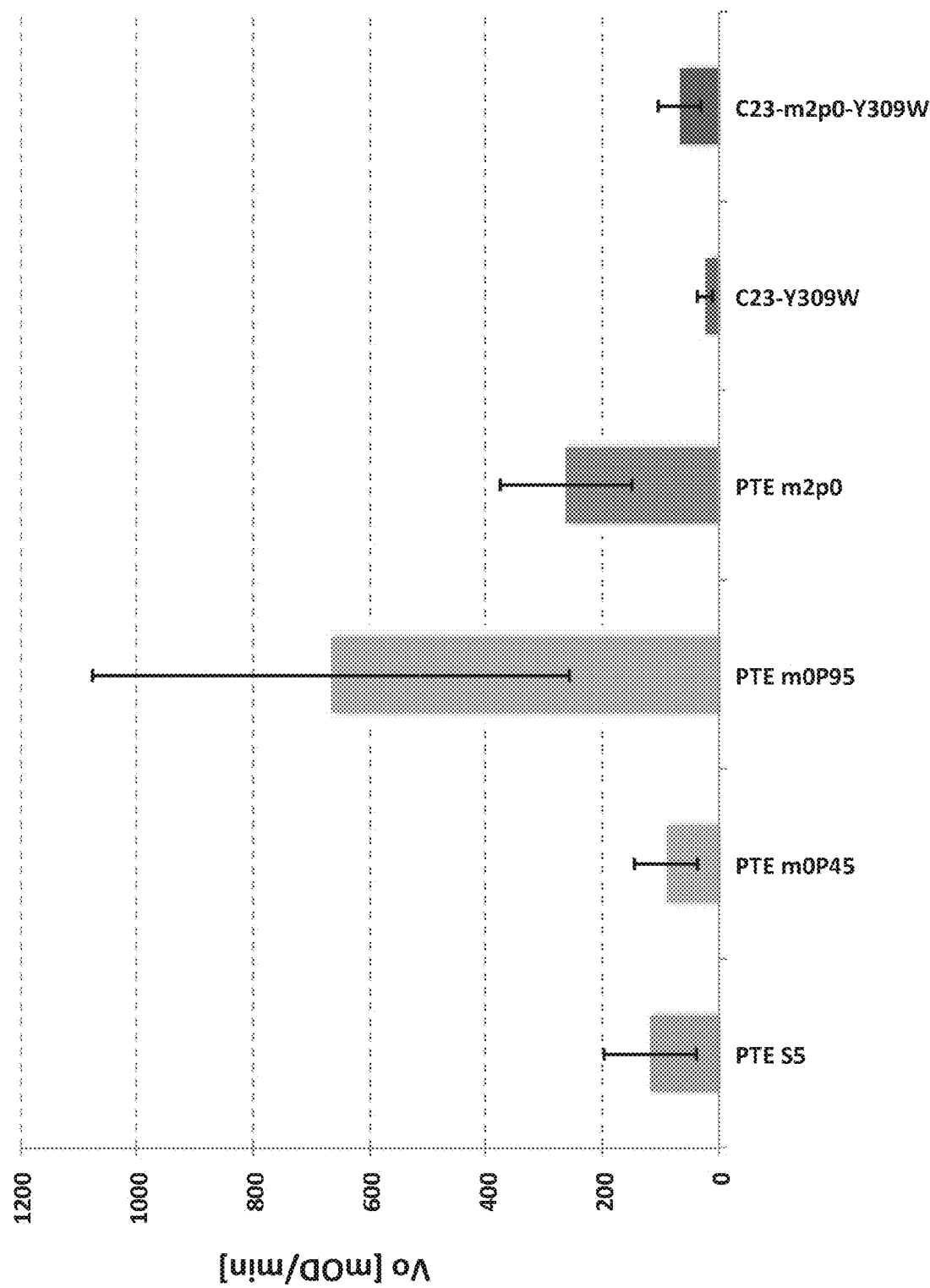
Figure 10:
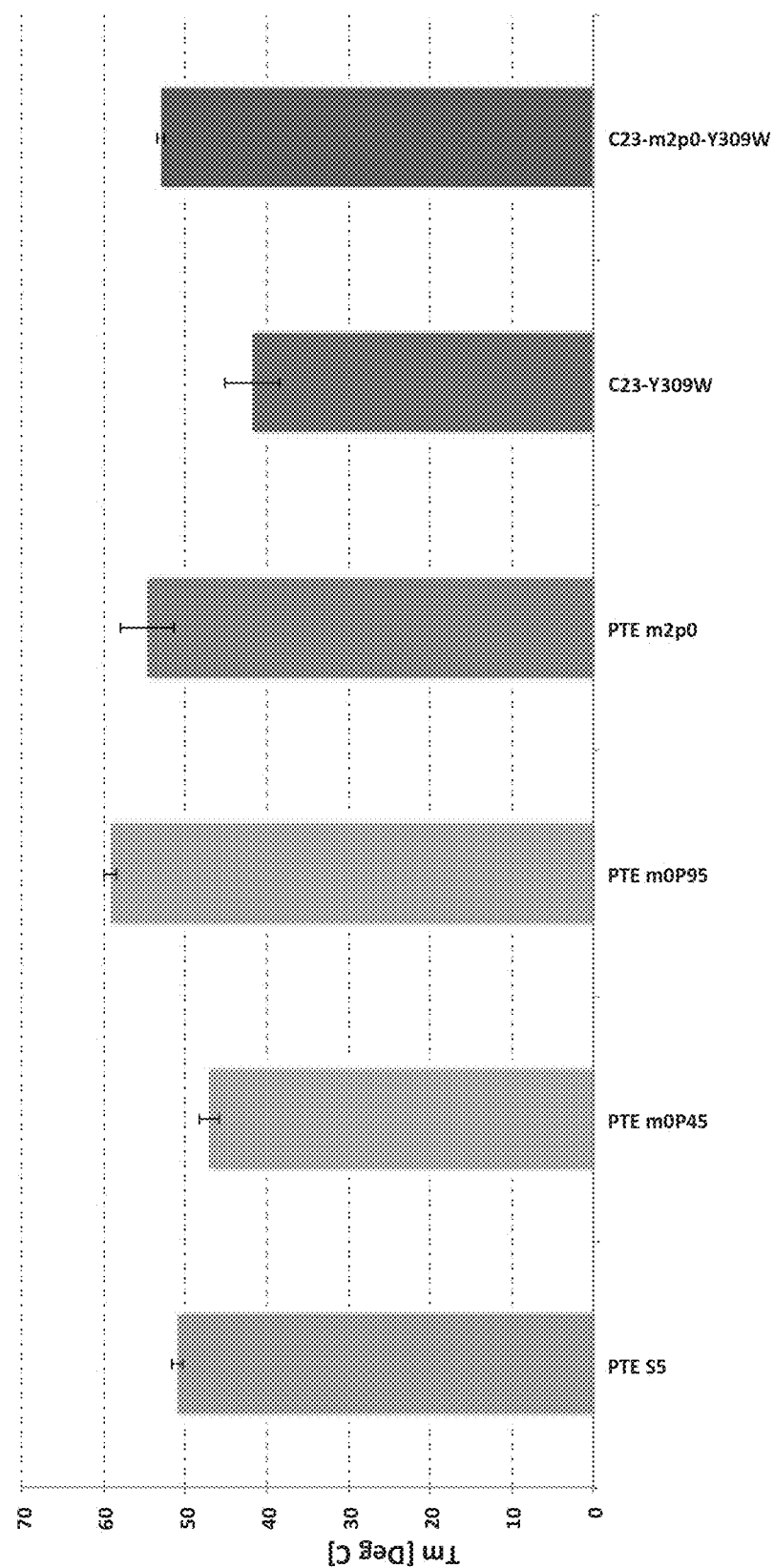

Materials and Methods
Preparation of Cell Lysates:
PTE expressing plasmids were transformed to GG48 (Zn$^{2+}$ internal cell concentration enhancing strain), grown on plates O/N.
Single colonies were picked from each variant into 96-Deep well plates and grown in 12 replicates up to OD=0.5.
IPTG 0.5 mM induction at 20° C. for 26 hours.
Cells were pelleted, dried and frozen −80° C.
Cell pellets were lysed (300 ml buffer, 37 Deg C., 60', 1200 RPM).
Lysates was pelleted for clarification (30', 4 Deg C., 4000 RPM).
20 ml clear lysate aliquots were taken to a 96 well PCR plate from each lysate (using precision 2000 liquid handling robot)×2.
Thermostability Assay:
A 96-well PCR plate was placed in a PCR machine (OPTRA).
Cell lysates were incubated for 30 min in a gradient of temperatures from 45° C.-70° C.
Cell lysates were then cooled to 4° C. for 10 min, and remained at 4° C. until completion of the assay.
Samples were diluted 1:200 in PTE AB (5 ul+995 ul Activity buffer no zinc).
Experiments were performed on one plate, sampled for activity assay twice.
Metal Binding Affinity Assay:
20 ml of 1,10-phenanthroline (100 mM) were added to each of well of a 96-PCR well plate containing 20 ml clear cell lysate (final 50 mM 1,10-phenanthrolin)—using the precision 2000 robot.
The plate was incubated for 30 min at 37° C.
Samples were dilute 1:200 in PTE AB (5 ul+995 ul Activity buffer no zinc.)
5 ml samples were taken to a 96-well ELISA plate for measuring paraoxonase activity with 195 ml Paraoxon 0.2 mM in PTE AB (no Zinc). Final dilution 1:8000.
Experiments were performed on two independent plates each sampled once.
Room Temperature Activity Assay:
Samples were diluted 1:200 in PTE AB (5 ul+995 ul Activity buffer no zinc).
5 ml samples were taken to a 96-well ELISA plate for measuring paraoxonase activity with 195 ml Paraoxon 0.2 mM in PTE AB (no Zinc). Final concentration 1:8000.
Experiments were performed on one plate, sampled for activity assay twice.
Results
FIG. 7 is a bar graph illustrating the cell lysate paraoxonase activity of particular variants performed at room temperature.
FIG. 8 is a bar graph illustrating the room temperature activities measured following a 5-6 hour incubation in the absence of Zinc.
FIG. 9 represents the average residual activity after 30 minute incubation with 50 µM 1,10-orthophenanthroline of particular variants. Error bars denote the S.D. for all replicas of each clone from two individual experiments.
FIG. 10 is a bar graph illustrating the thermal activity of particular variants.

Example 6

Figure 11:
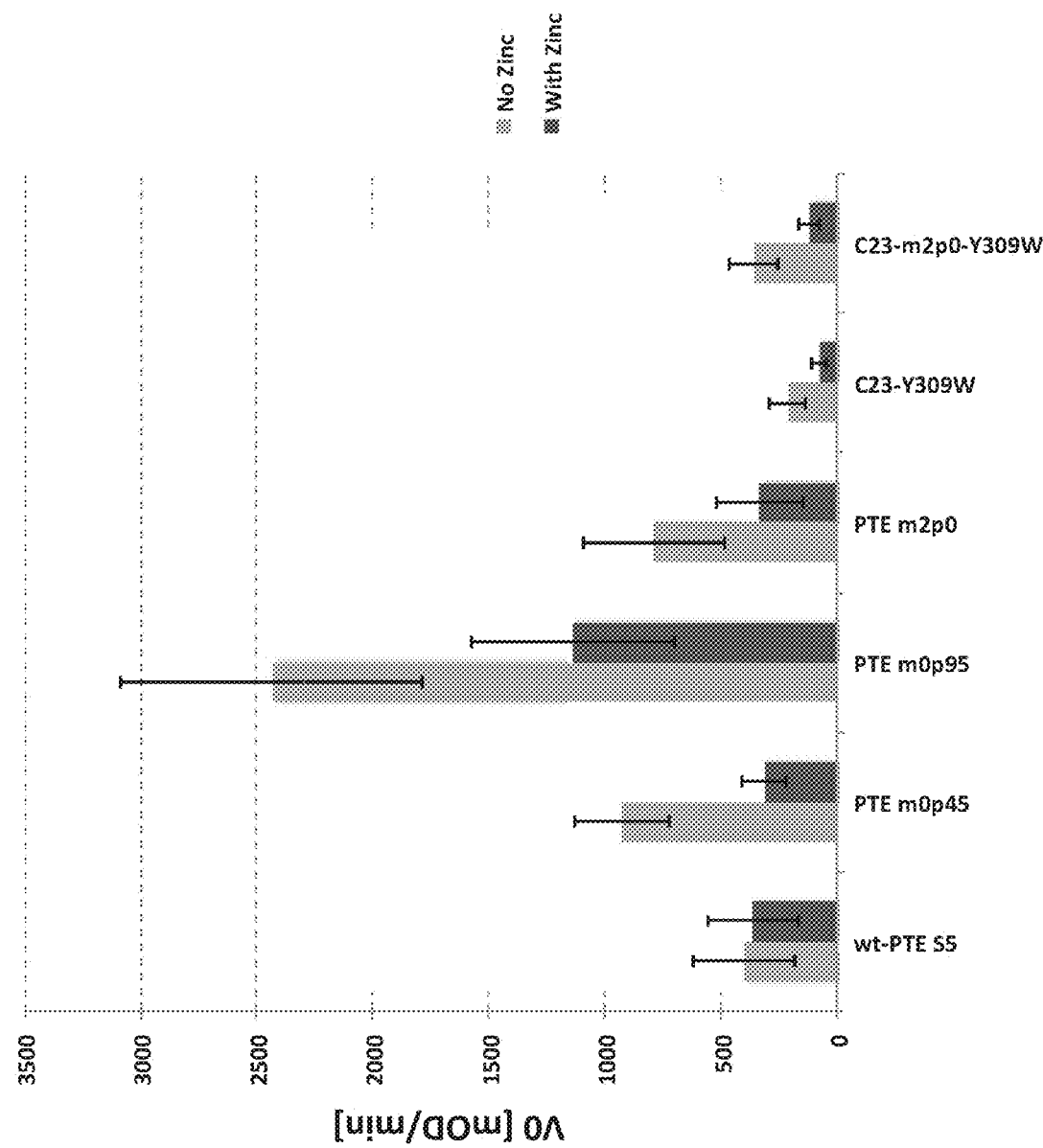

Thermostability Experiments Performed on Cell Lysates Comprising Stabilized Variants These experiments were performed to compare between the apparent Tm measured using residual RT paraoxonase activity in cell lysates with Zinc in the lysis buffer, to the apparent Tm measured in lysates with no Zinc in the lysis buffer.
In addition, the experiments were performed in order to compare the effect of buffer zinc conc' on RT paraoxonase activity.
Materials and Methods
The experiments were performed as described for Example 5 except for the addition of zinc ions into the lysate buffer (40 mM Zn$^{2+}$ final concentration).
The paraoxon assay was performed in a final 1 mM Zinc buffer concentration to avoid inhibition by high zinc concentration.
Tm was evaluated using a low (30-55° C.) and high (45-70° C.) temperature gradients.
Results
FIG. 11 is a bar graph illustrating the cell lysate paraoxonase activity of particular variants performed at room temperature in the presence and absence of zinc.
FIG. 12 is a bar graph illustrating the thermal activity of particular variants in the presence and absence of zinc.
Table 14 summarizes the stability of M2p0, M0p95 and m0p45 with respect to C23, both as a cell lysate and as purified proteins.

TABLE 14

| Protein | Mutations[1] | Expression[2] | $T_m^{app}$ Lysate [°C.] | $T_m^{app}$ Purified [°C.] | $T_{1/2}$ Chelator [min] | $K_M$[3] (μM) | $k_{cat}$[3] (sec$^{-1}$) | $k_{cat}/K_M$[3] × 10$^7$ (M$^{-1}$sec$^{-1}$) |
|---|---|---|---|---|---|---|---|---|
| C23 | 3 | 1 | 50.9 ± 0.7 | 52 ± 0.2 | 7.2 ± 0.1 | 101 ± 23 | 1615 ± 126 | 1.6 ± 0.4 |
| PTE m2p0 | 9 | 2.0 | 54.7 ± 3.2 | nd | nd | nd | nd | nd |
| PTE m0P95 | 19 | 6.1 | 59.2 ± 0.7 | 62 ± 0.15 | 46 ± 2.6 | 60 ± 14 | 1167 ± 82 | 1.9 ± 0.5 |
| PTE m0P45 | 28 | 2.3 | 47.0 ± 1.3 | nd | nd | nd | nd | nd |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

What is claimed is:

1. A genetically modified phosphotriesterase (PTE) polypeptide:
   (a) comprising an amino acid sequence at least 95% identical to SEQ ID NO: 6;
   (b) comprising a Leucine residue at position 203, where the coordinates correspond to the PTE having the sequence (SEQ ID NO: 5), and
   (c) having at least twice the catalytic efficiency for a V-type nerve agent as a PTE polypeptide which consists of the sequence as set forth in SEQ ID NO: 1, when assayed at 25° C. under identical conditions, wherein said modified PTE polypeptide is devoid of the first 29 amino acids of SEQ ID NO: 5.

2. The genetically modified PTE polypeptide of claim 1, wherein said V-type nerve agent comprises an Sp isomer.

3. The genetically modified PTE polypeptide of claim 1, wherein said V-type nerve agent is selected from the group consisting of VX, RVX and CVX.

4. The genetically modified PTE polypeptide of claim 1, wherein said V-type nerve agent is the Sp isomer of VX.

5. A genetically modified phosphotriesterase (PTE) polypeptide:
   (a) comprising an amino acid sequence at least 95% identical to SEQ ID NO: 6;
   (b) comprising an Asparagine residue at position 173 where the coordinates correspond to the PTE having the sequence (SEQ ID NO: 5), and
   (c) having catalytic efficiency $k_{cat}/K_M$ greater than $3 \times 10^6$ $M^{-1} min^{-1}$ for the Sp isomer of RVX, retaining at least 50% of its catalytic activity at 50° C. as its catalytic activity at 25° C., when measured in a cell lysate, wherein said modified PTE polypeptide is devoid of the first 29 amino acids of SEQ ID NO: 5.

6. The genetically modified PTE polypeptide of claim 5, having a catalytic activity in the presence of 50 μM of the metal chelator 1,10 phenanthroline at least 50% of its catalytic activity in the absence of said metal chelator.

7. A genetically modified PTE polypeptide:
   (a) comprising an amino acid sequence at least 95% identical to SEQ ID NO: 6;
   (b) comprising the mutation Y309W, where the coordinates correspond to the PTE having the sequence (SEQ ID NO: 5), and
   (c) having at least twice the catalytic efficiency for a V-type nerve agent as a PTE polypeptide which consists of the sequence as set forth in SEQ ID NO: 1, when assayed at 25° C. under identical conditions, wherein said modified PTE polypeptide is devoid of the first 29 amino acids of SEQ ID NO: 5.

8. The genetically modified PTE polypeptide of claim 1, wherein the amino acid of PTE at position 271 is glycine or arginine, where the coordinates correspond to the PTE having the sequence (SEQ ID NO: 5).

9. The genetically modified PTE polypeptide of claim 8, wherein said amino acid sequence of PTE further comprises the mutation L272W, where the coordinates correspond to the PTE having the sequence (SEQ ID NO: 5).

10. The genetically modified PTE polypeptide of claim 7, wherein said amino acid sequence of PTE further comprises the mutation A270S and/or A203L, where the coordinates correspond to the PTE having the sequence (SEQ ID NO: 5).

11. The genetically modified PTE polypeptide of claim 1, wherein said amino acid sequence of PTE further comprises the mutations F132E, T173N and H254G, where the coordinates correspond to the PTE having the sequence (SEQ ID NO: 5).

12. The genetically modified PTE polypeptide of claim 5, wherein the amino acid at position 203 of said polypeptide is alanine, where the coordinates correspond to the PTE having the sequence (SEQ ID NO: 5).

13. The genetically modified PTE polypeptide of claim 5, wherein the amino acid at position 203 of said polypeptide is phenylalanine where the coordinates correspond to the PTE having the sequence (SEQ ID NO: 5).

14. The genetically modified PTE polypeptide of claim 5, wherein said amino acid sequence of PTE comprises the mutation T173N, I106A, F132E and H254G, where the coordinates correspond to the PTE having the sequence (SEQ ID NO: 5).

15. The genetically modified PTE polypeptide of claim 5, further comprising the mutation A203F or A203L, where the coordinates correspond to the PTE having the sequence (SEQ ID NO: 5).

16. The genetically modified PTE polypeptide of claim 1, comprising an amino acid sequence at least 99% homologous to the sequence as set forth in SEQ ID NO: 2, 13, 15, 19 and 23.

17. The genetically modified PTE polypeptide of claim 5, comprising an amino acid sequence at least 99% homologous to the sequence as set forth in SEQ ID NO: 4, 8, 21 or 23.

18. An isolated polynucleotide comprising a nucleic acid sequence encoding the PTE polypeptide of claim 1.

19. A pharmaceutical composition comprising as an active ingredient the isolated PTE polypeptide of claim 1 and a pharmaceutically acceptable carrier.

20. A method of treating an organophosphate exposure associated damage in a subject, comprising administering to the subject a therapeutically effective amount of the isolated PTE polypeptide of claim 1.

21. An article of manufacture for treating or preventing organophosphate exposure associated damage, the article of manufacture comprising the isolated PTE polypeptide of claim 1 immobilized on to a solid support.

22. A method of detoxifying a surface, the method comprising contacting the surface with the isolated PTE polypeptide of claim 1, thereby detoxifying the surface.

23. A genetically modified PTE polypeptide comprising an amino acid sequence at least 99% homologous to the sequence as set forth in SEQ ID NO: 2, 3, 11, 13, 15, 17, 19, 25, 27, 29, 31, 33 or 35, wherein said modified PTE polypeptide has catalytic efficiency $k_{cat}/K_M$ greater than $3\times10^6$ $M^{-1}min^{-1}$ for the Sp isomer of RVX, retaining at least 50% of its catalytic activity at 50° C. as its catalytic activity at 25° C., when measured in a cell lysate, wherein said modified PTE polypeptide is devoid of the first 29 amino acids of SEQ ID NO: 5.

24. The PTE polypeptide of claim 23, wherein said amino acid sequence is as set forth in any one of SEQ ID NO: 2, 3, 11, 13, 15, 17, 19, 25, 27, 29, 31, 33 or 35.

25. A pharmaceutical composition comprising as an active ingredient the isolated PTE polypeptide of claim 23 and a pharmaceutically acceptable carrier.

26. A method of treating an organophosphate exposure associated damage in a subject, comprising administering to the subject a therapeutically effective amount of the isolated PTE polypeptide of claim 23.

27. An article of manufacture for treating or preventing organophosphate exposure associated damage, the article of manufacture comprising the isolated PTE polypeptide of claim 23 immobilized on to a solid support.

28. A method of detoxifying a surface, the method comprising contacting the surface with the isolated PTE polypeptide of claim 23, thereby detoxifying the surface.

29. A genetically modified PTE polypeptide, comprising an amino acid sequence at least 99% homologous to the sequence as set forth in SEQ ID NO: 4, 8, 21 or 23 and having catalytic efficiency $k_{cat}/K_M$ greater than $3\times10^6$ $M^{-1}min^{-1}$ for the Sp isomer of RVX, retaining at least 50% of its catalytic activity at 50° C. as its catalytic activity at 25° C., when measured in a cell lysate.

30. The PTE polypeptide of claim 29, wherein said amino acid sequence is as set forth in any one of the sequences SEQ ID NO: 4, 8, 21 or 23.

* * * * *